US009534993B2

(12) United States Patent
Bond et al.

(10) Patent No.: US 9,534,993 B2
(45) Date of Patent: Jan. 3, 2017

(54) ENTROPY-BASED IMPACT LOAD IDENTIFICATION

(75) Inventors: Ray Bond, Lafayette, IN (US); Douglas E. Adams, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 234 days.

(21) Appl. No.: 13/882,891

(22) PCT Filed: Nov. 1, 2011

(86) PCT No.: PCT/US2011/058841
§ 371 (c)(1),
(2), (4) Date: May 1, 2013

(87) PCT Pub. No.: WO2012/061431
PCT Pub. Date: May 10, 2012

(65) Prior Publication Data
US 2013/0298690 A1  Nov. 14, 2013

Related U.S. Application Data

(60) Provisional application No. 61/408,915, filed on Nov. 1, 2010.

(51) Int. Cl.
*G01N 3/00* (2006.01)
*G01L 5/00* (2006.01)
*G01M 5/00* (2006.01)

(52) U.S. Cl.
CPC ............... *G01N 3/00* (2013.01); *G01L 5/0052* (2013.01); *G01M 5/0033* (2013.01); *G01M 5/0066* (2013.01)

(58) Field of Classification Search
CPC ......... G01L 5/0052; G01L 1/255; G01N 3/00; G01M 5/0066; G01M 5/0033; G01M 7/00; A63B 69/20; A63B 69/34; A63B 69/3632; A63B 24/0075; A63B 69/3635; A63B 2071/063; A63B 2220/53; A63B 69/32; A63B 69/0024; A63B 2071/0625; A63B 2220/40; G09B 19/0038
USPC .................................................. 73/766, 788
See application file for complete search history.

(56) References Cited

U.S. PATENT DOCUMENTS

| | | |
|---|---|---|
| 7,228,240 B2 | 6/2007 | Duron et al. |
| 2003/0015038 A1 | 1/2003 | Rodger et al. |
| 2003/0060903 A1 | 3/2003 | MacMartin et al. |
| 2005/0072234 A1 | 4/2005 | Zhu et al. |
| 2005/0247132 A1 | 11/2005 | Hamidieh et al. |
| 2008/0011091 A1 | 1/2008 | Weldon |
| 2008/0098797 A1 | 5/2008 | Considine et al. |

OTHER PUBLICATIONS

International Search Report and Written Opinion issued in PCT/US2011/058841 May 10, 2012.
International Preliminary Report on Patentability issued in PCT/US2011/058841 May 16, 2013.

*Primary Examiner* — Lisa Caputo
*Assistant Examiner* — Brandi Hopkins
(74) *Attorney, Agent, or Firm* — John V. Daniluck; Bingham Greenebaum Doll LLP

(57) ABSTRACT

Methods and apparatus for identifying the location of the load on a structure. Various embodiments include calculating a plurality of potential loading sites, assessing the statistical order of each of those predictions, and selecting regions of the structure where the load most likely occurred based on the orderliness (or randomness) of the assessments.

27 Claims, 44 Drawing Sheets

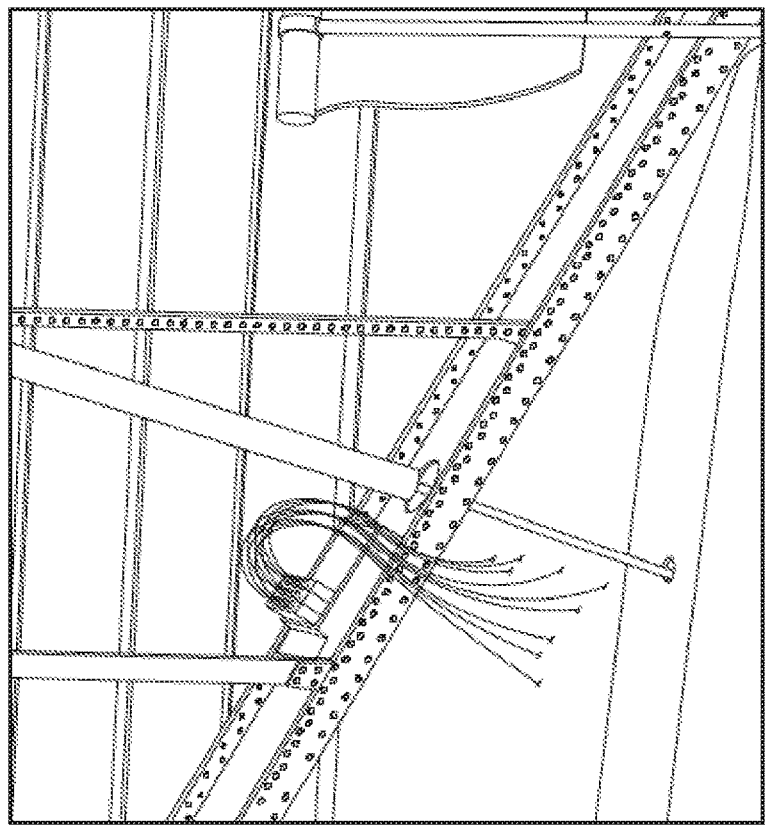
FIG. 2A
FIG. 2B
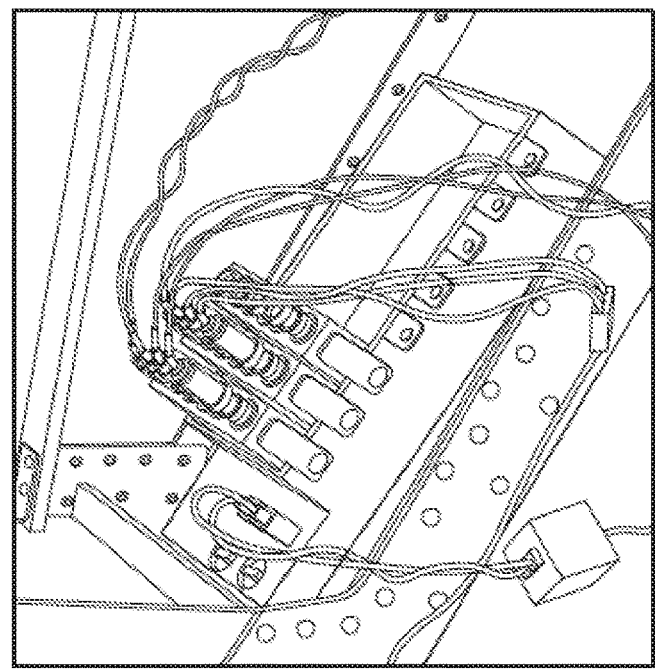

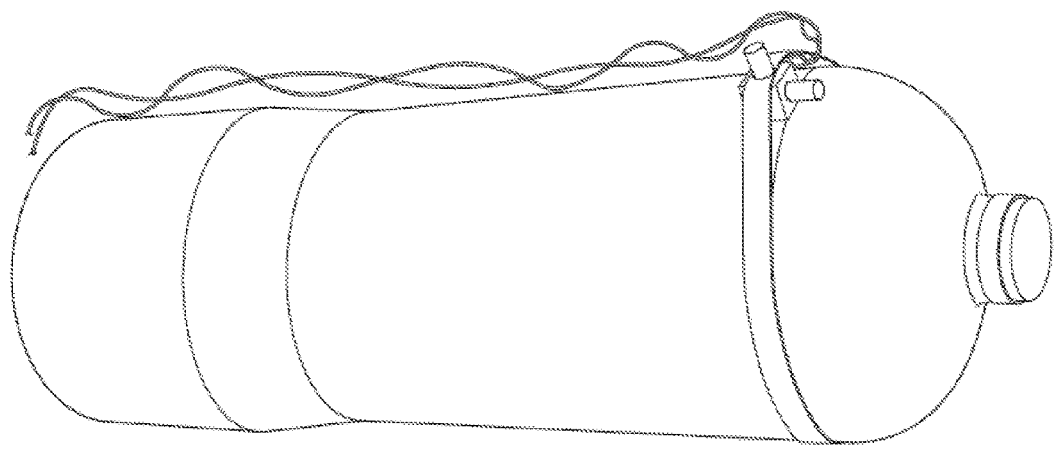
FIG. 12.1
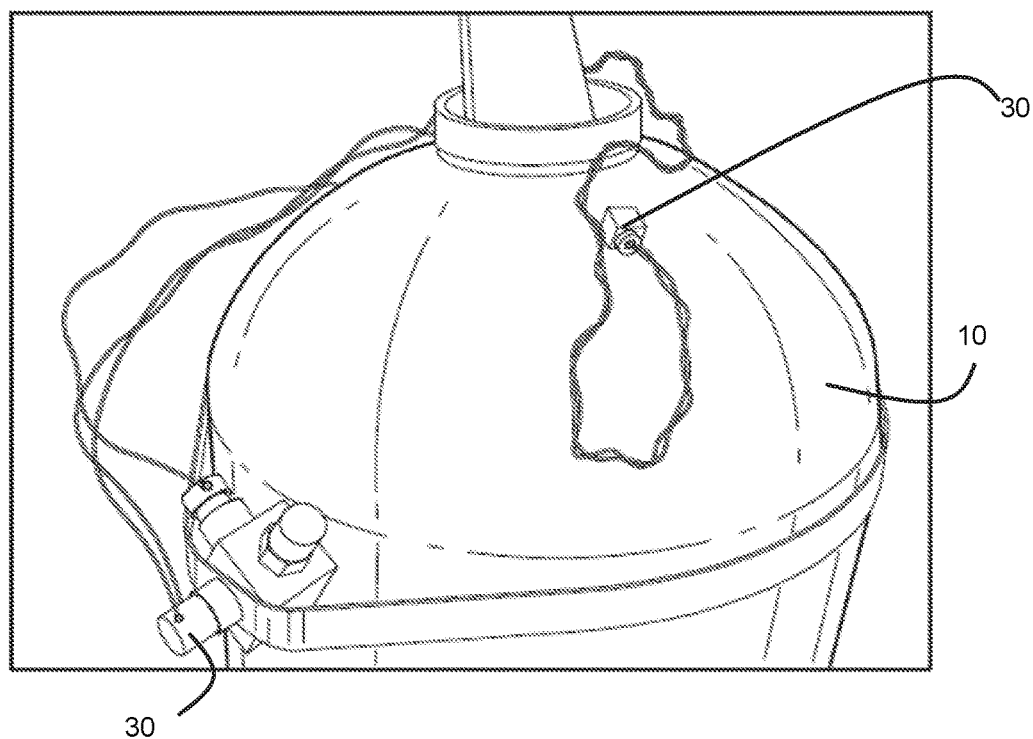
FIG. 12.2

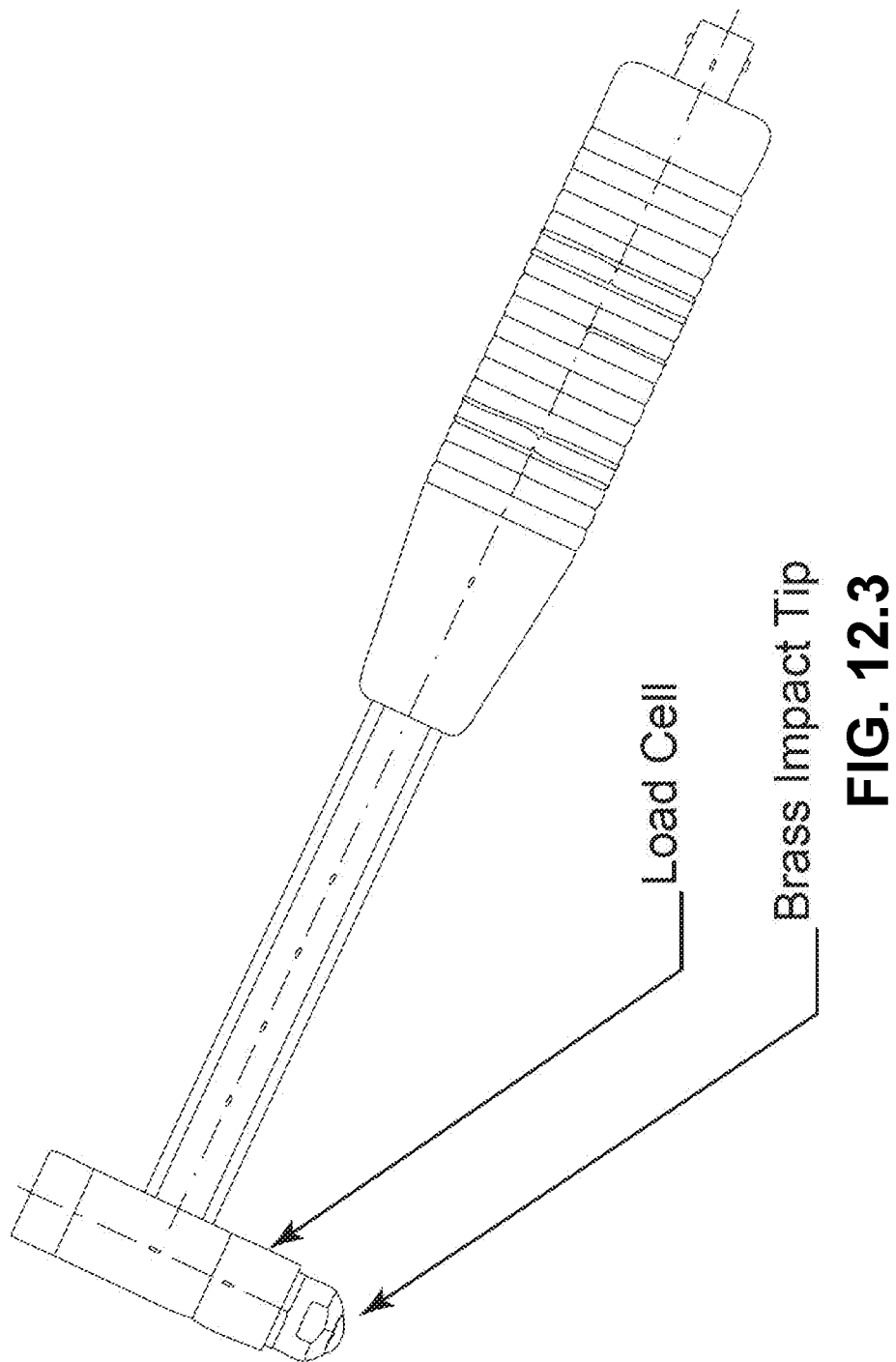

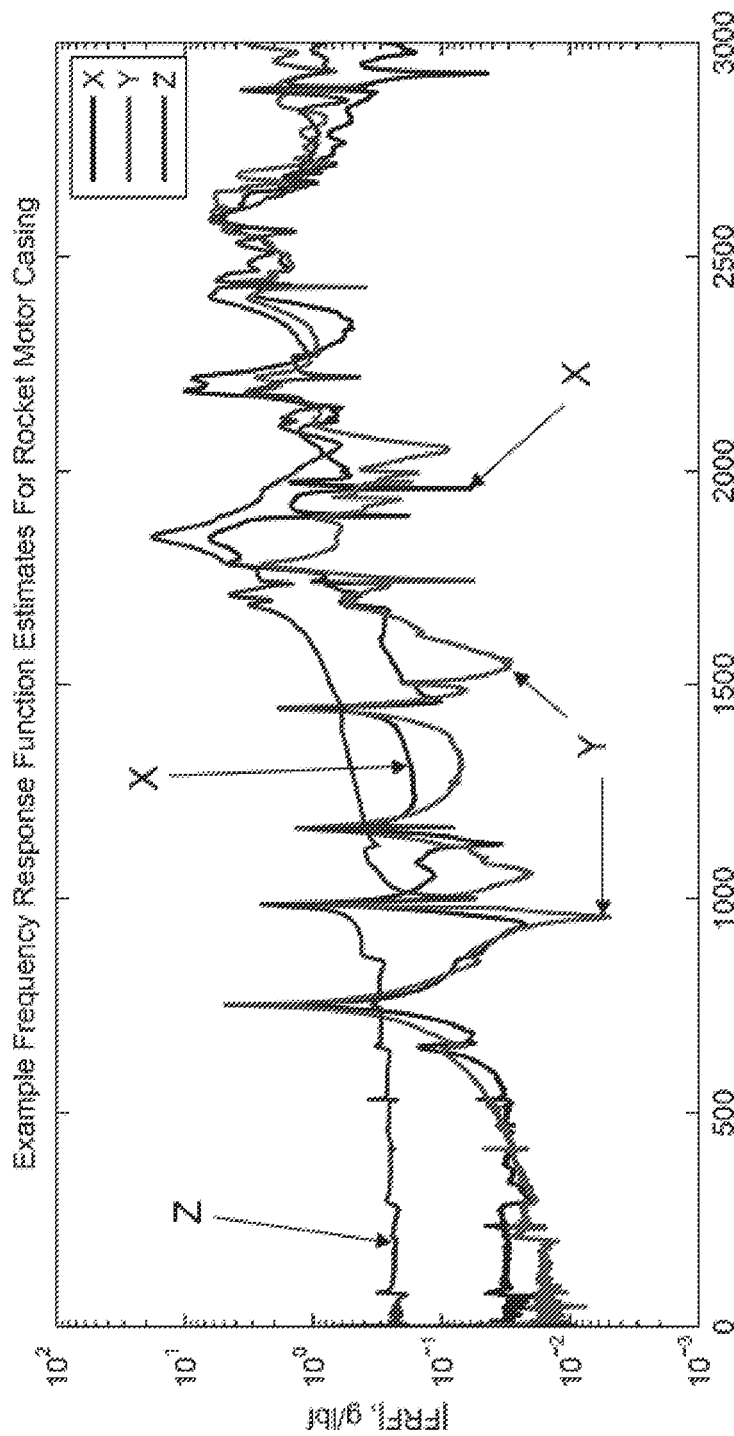
FIG. 12.4A

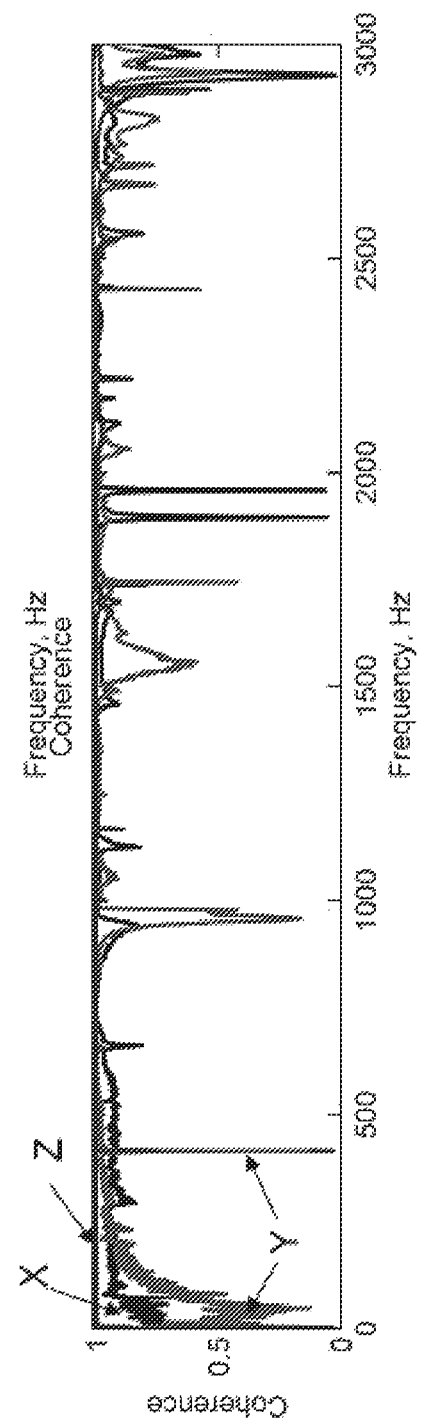
FIG. 12.4B

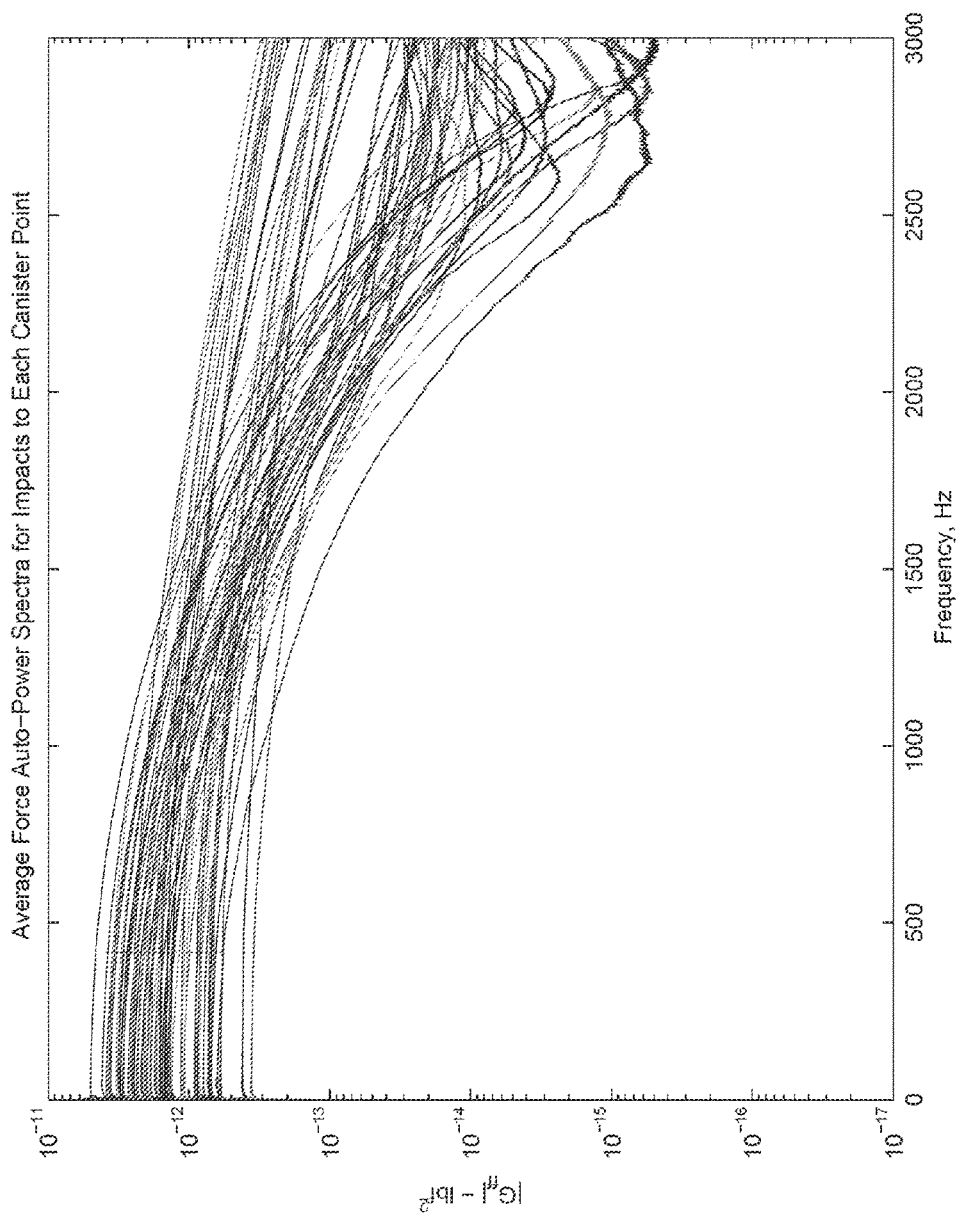
FIG. 12.5

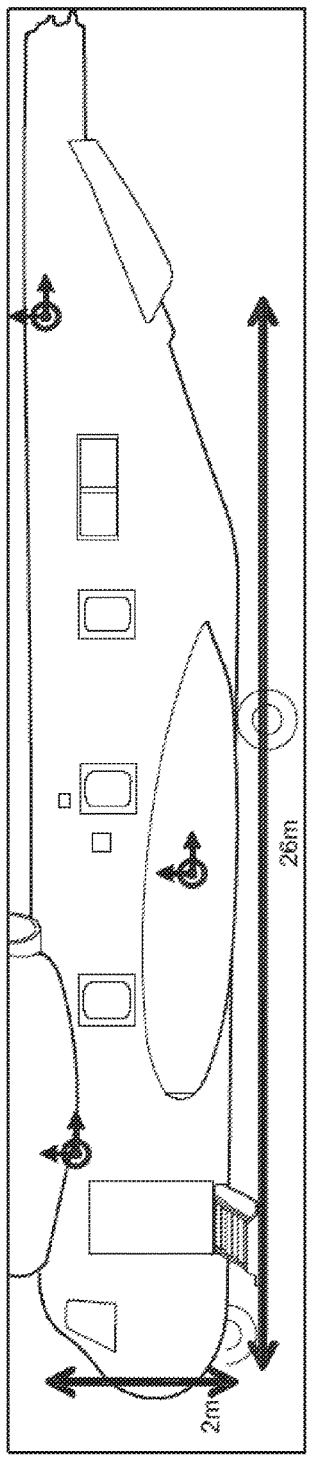
FIG. 12.6
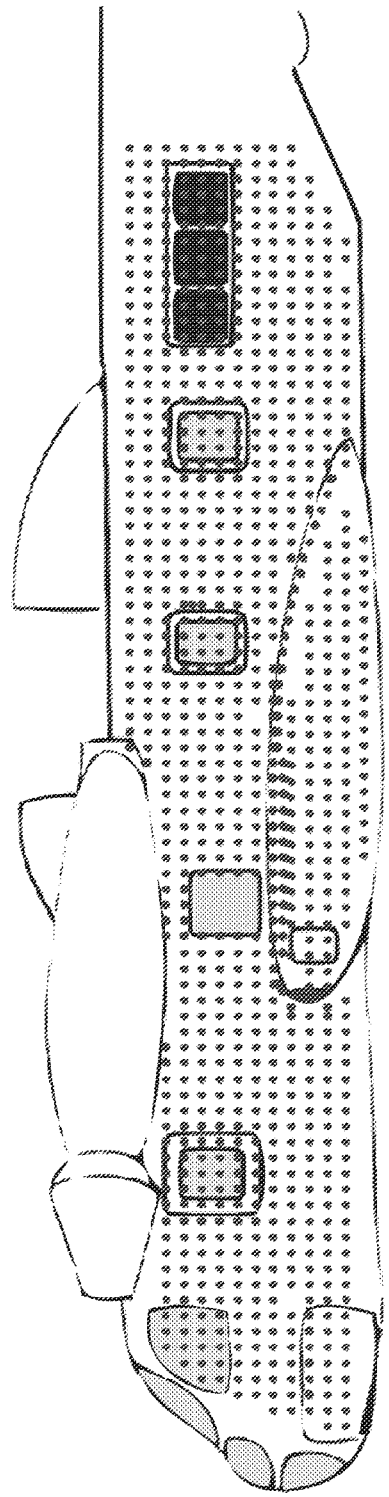
FIG. 12.7

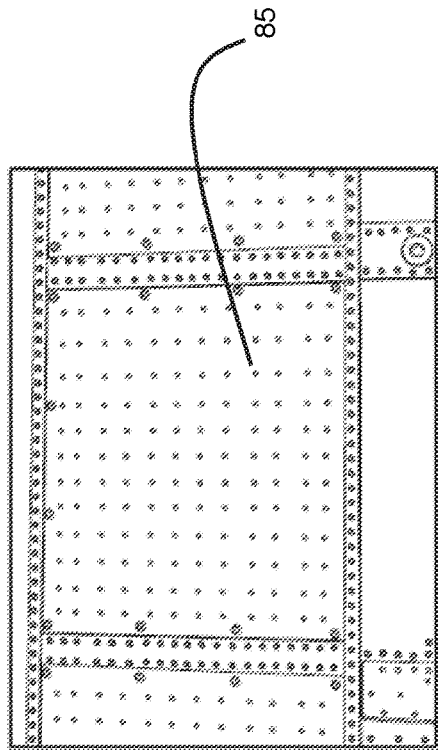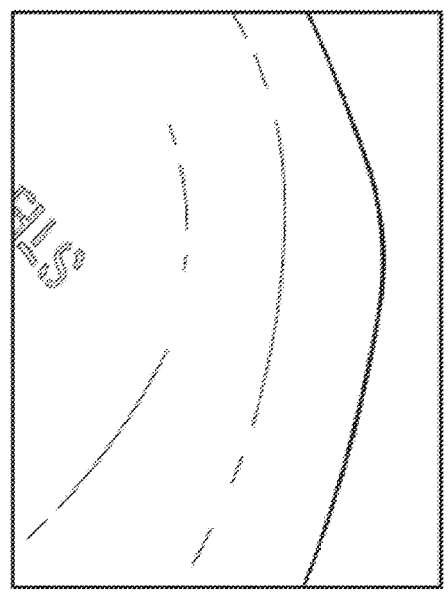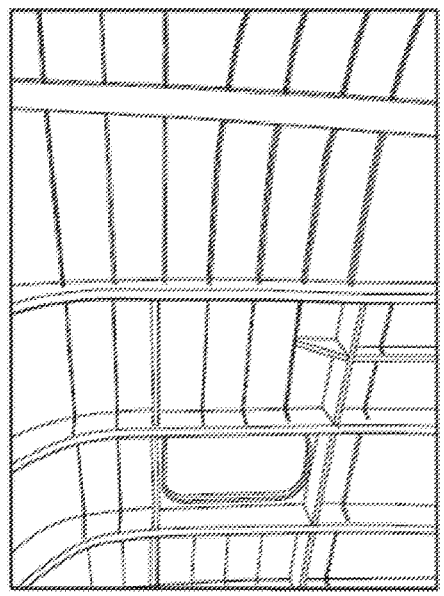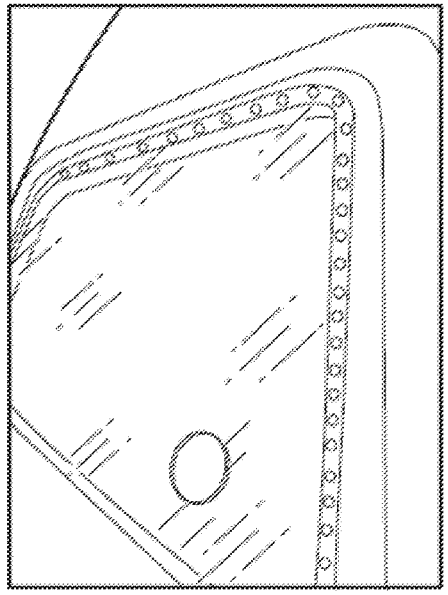
FIG. 12.8A  FIG. 12.8B  FIG. 12.8C  FIG. 12.8D

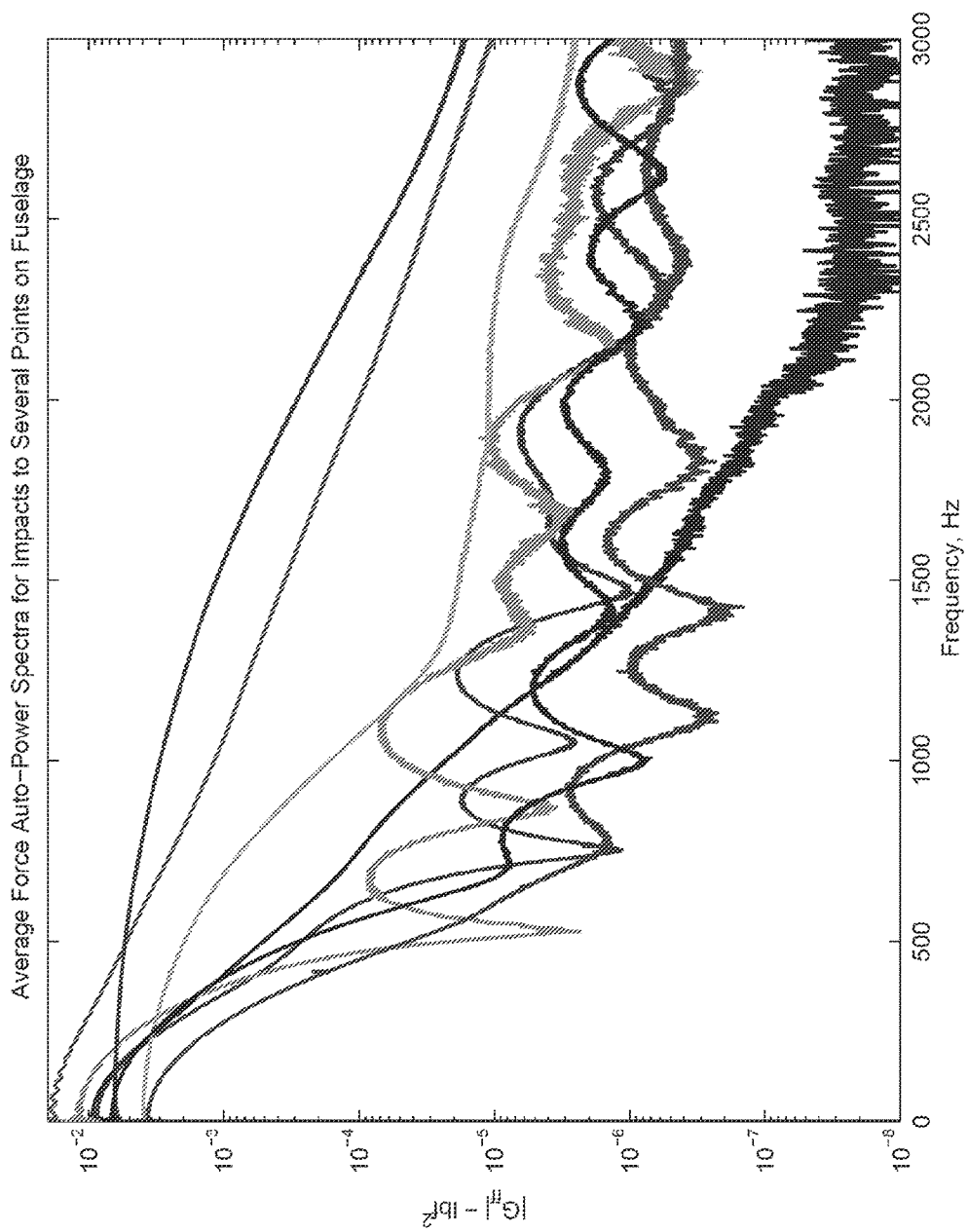
FIG. 12.9

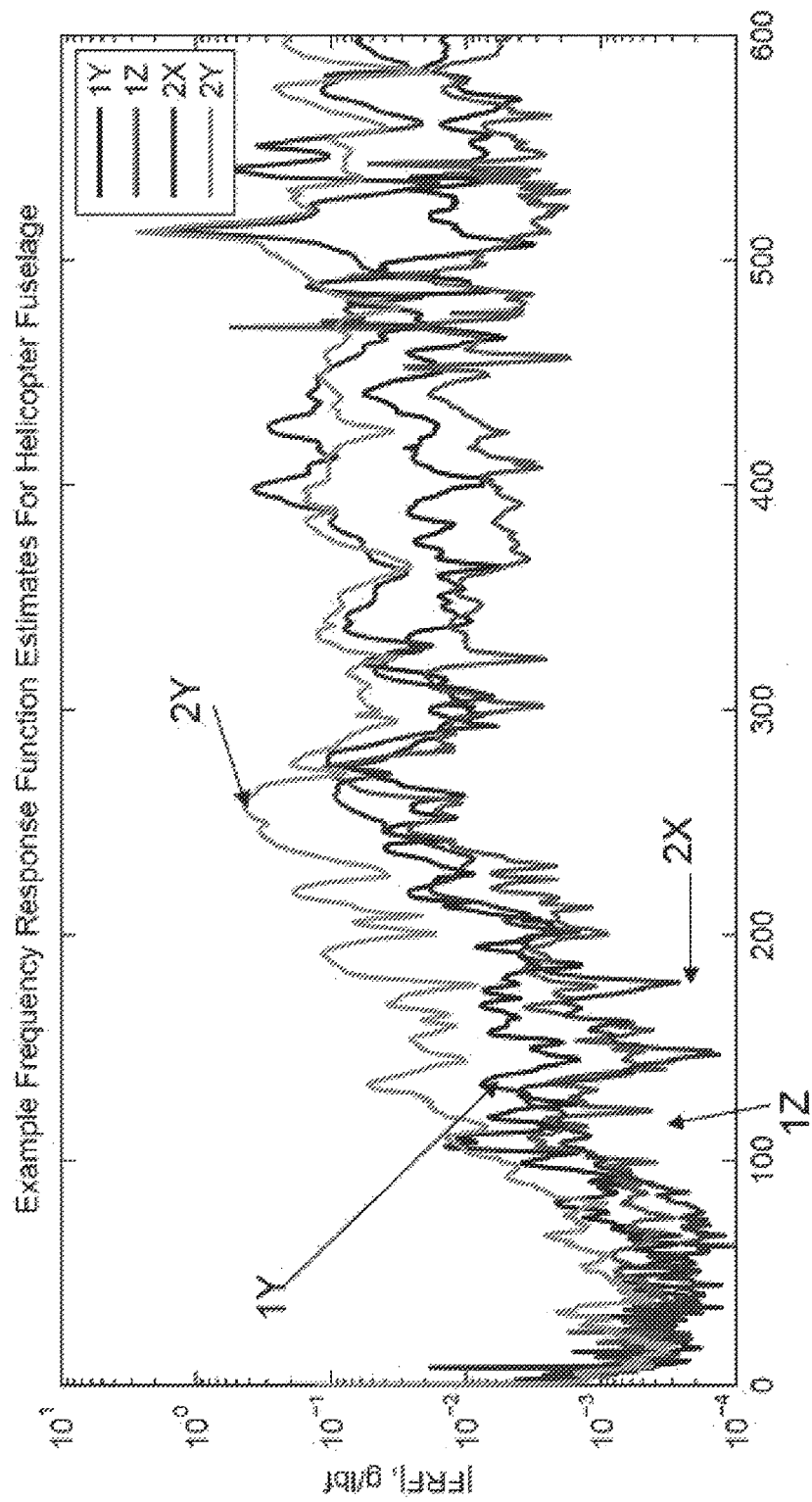
FIG. 12.10A

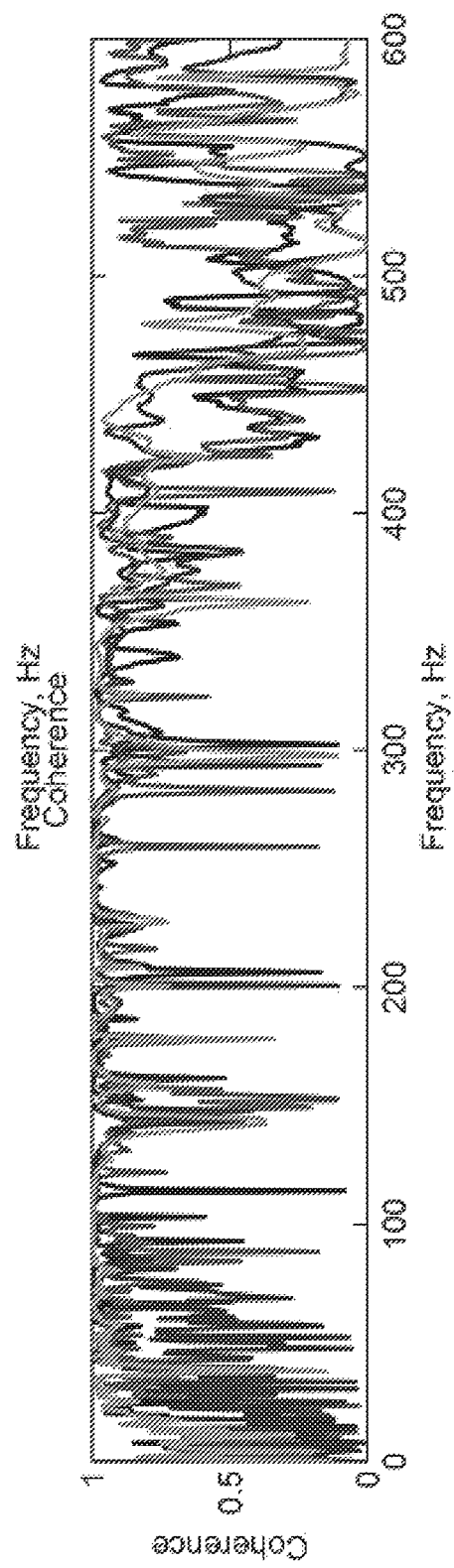
FIG. 12.10B

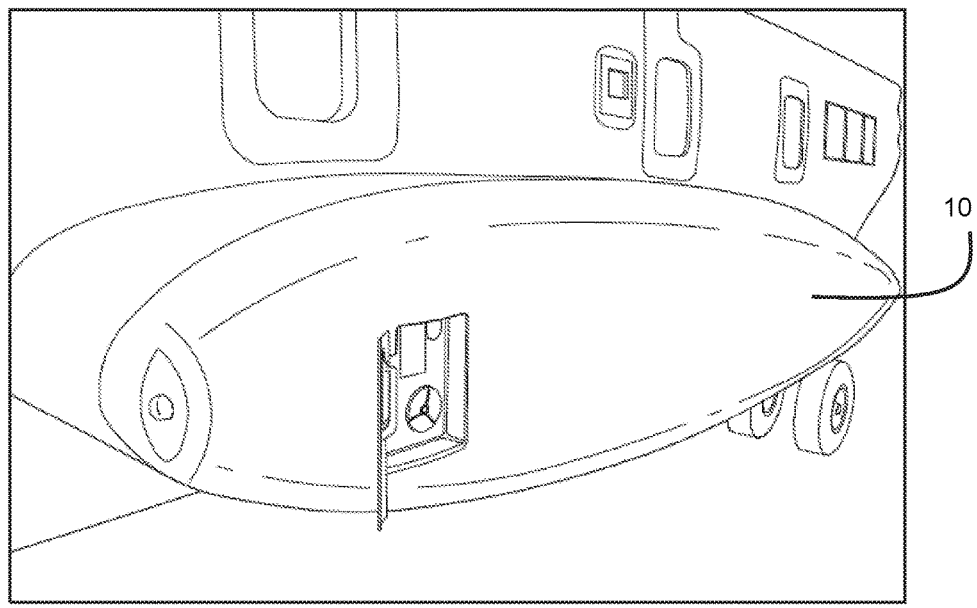
FIG. 12.11
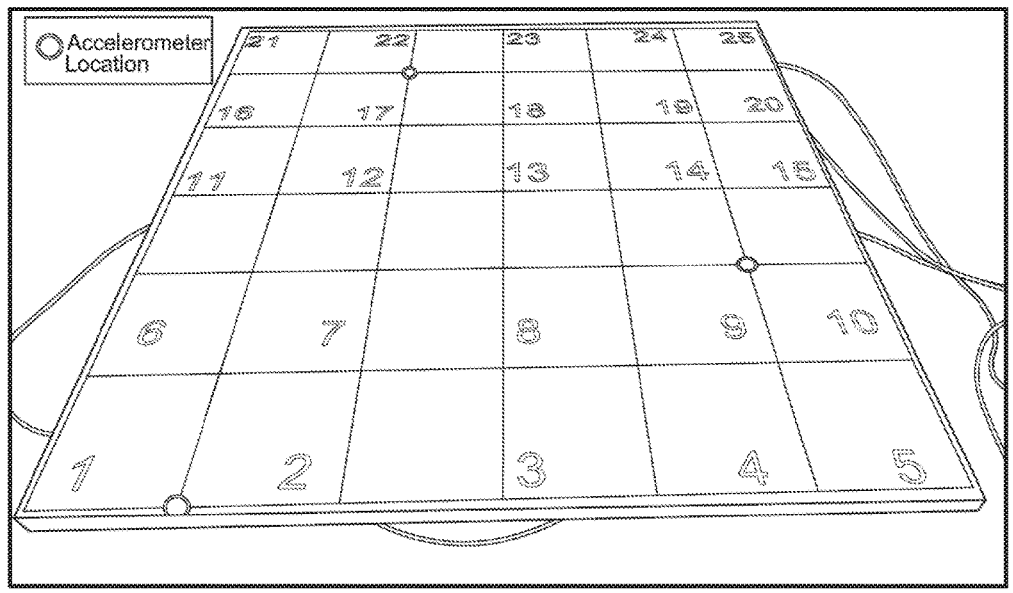
FIG. 12.12

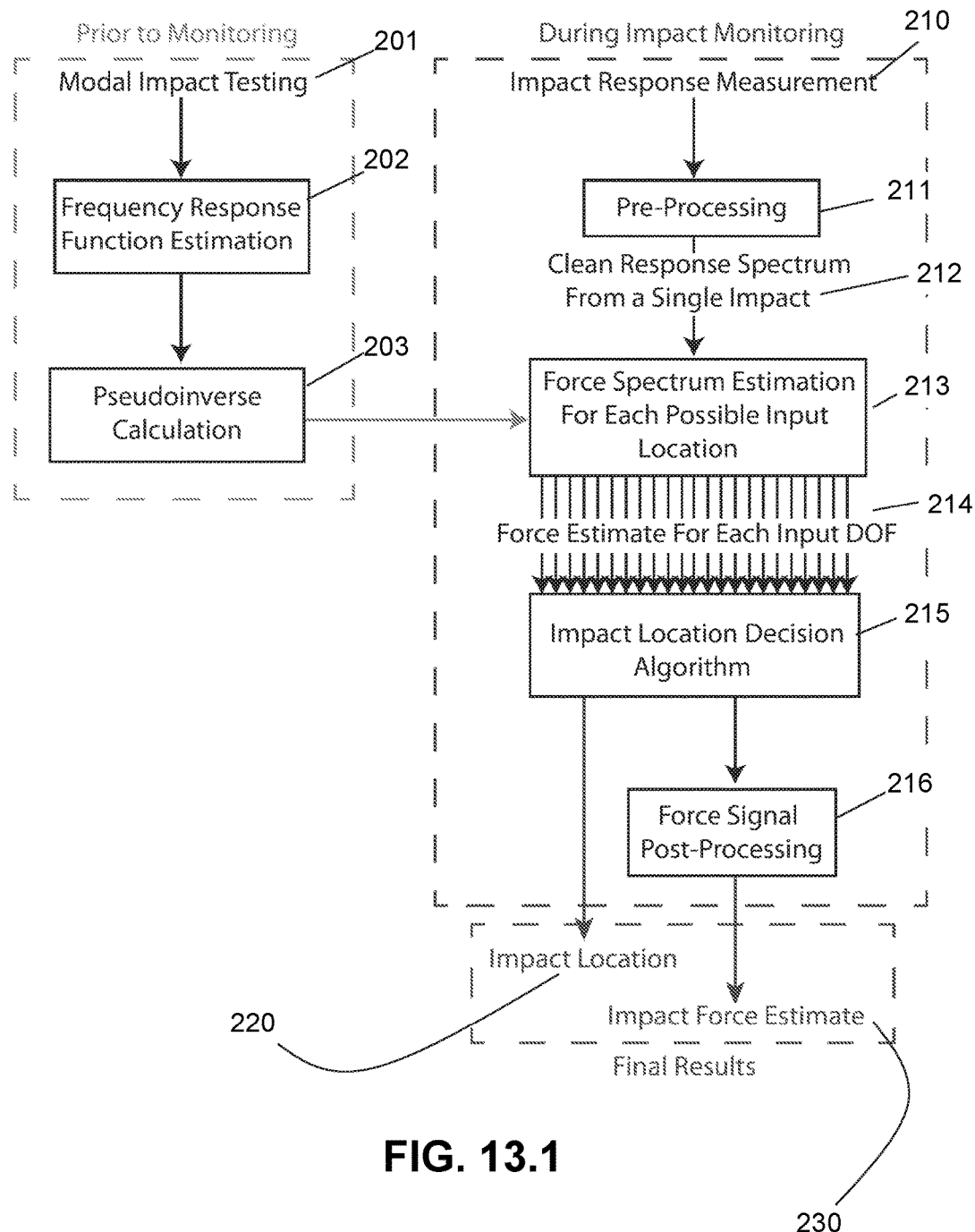
FIG. 13.1

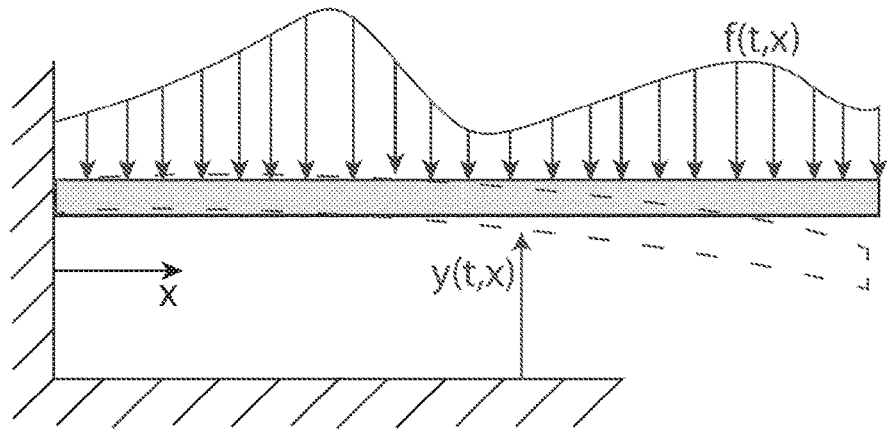
FIG. 13.2
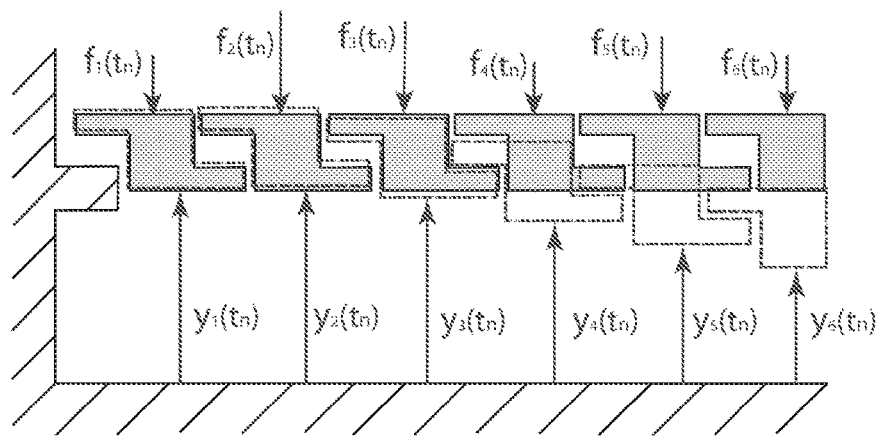
FIG. 13.3
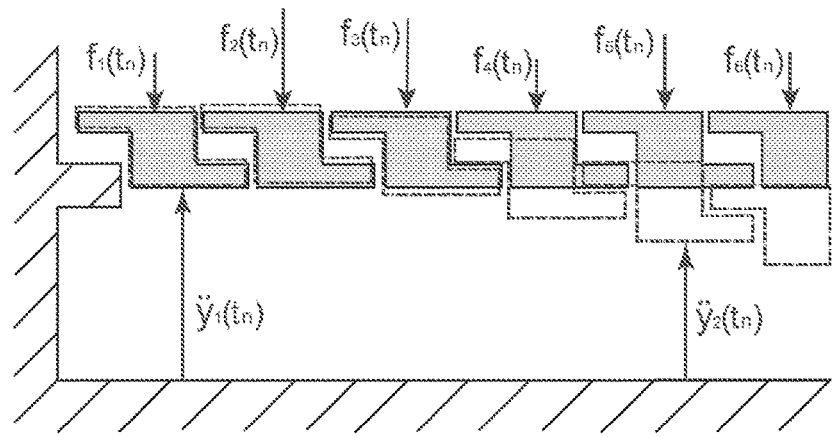
FIG. 13.4

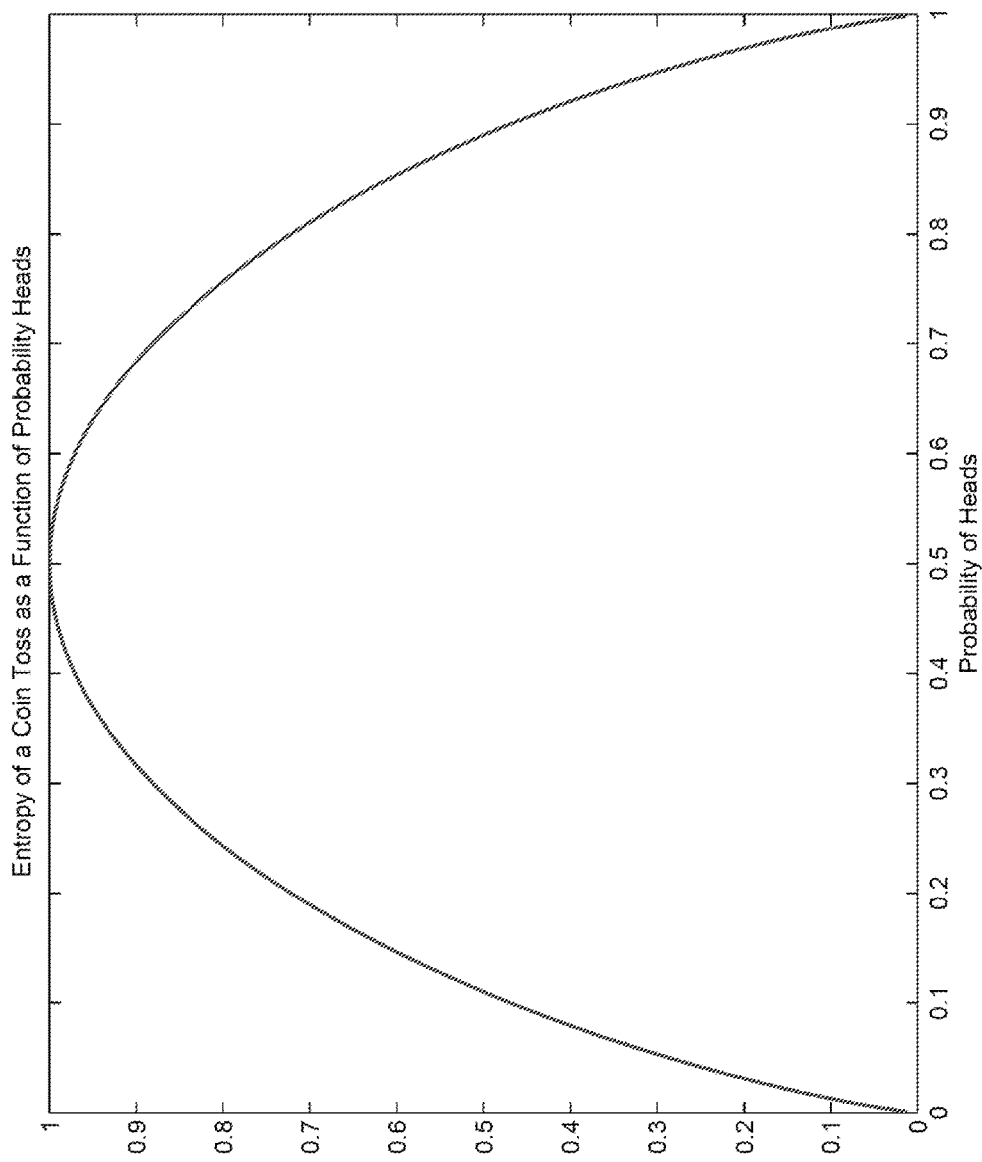
FIG. 13.5

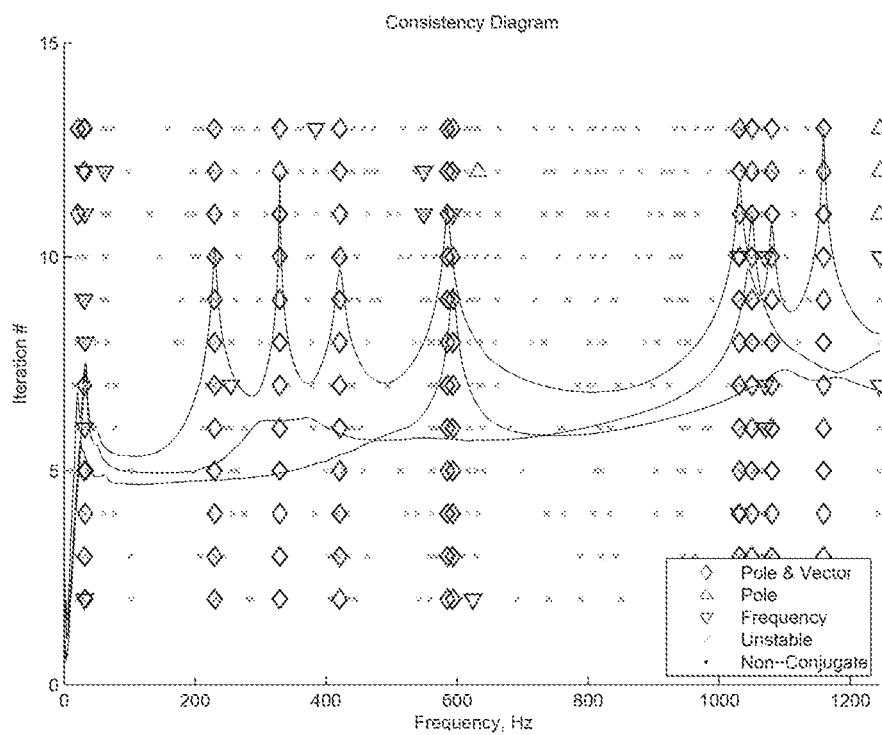
FIG. 13.6
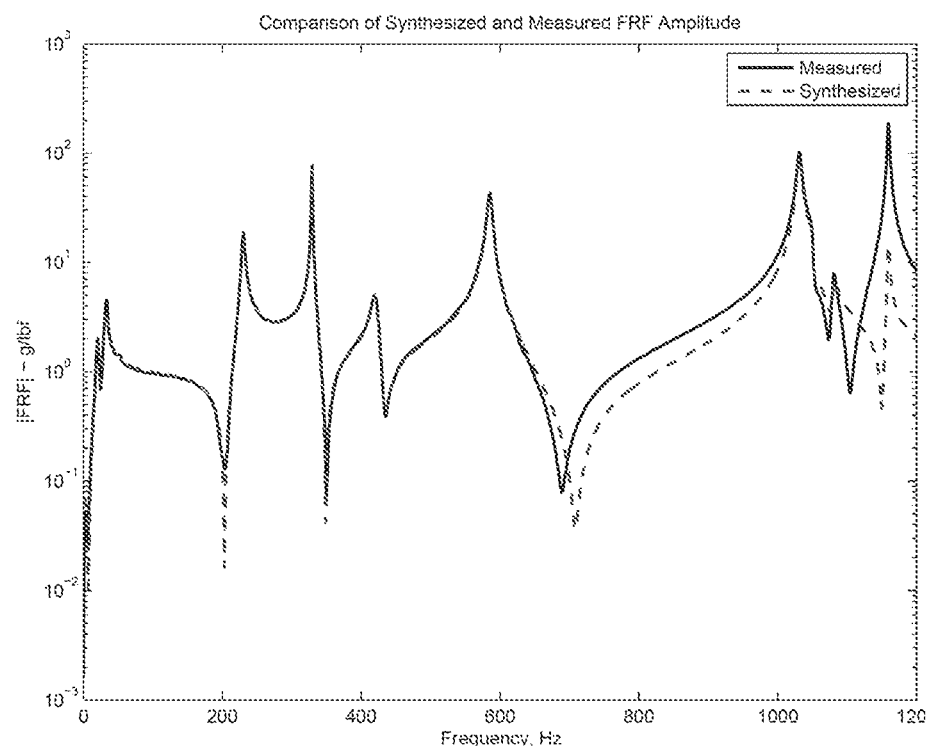
FIG. 13.7

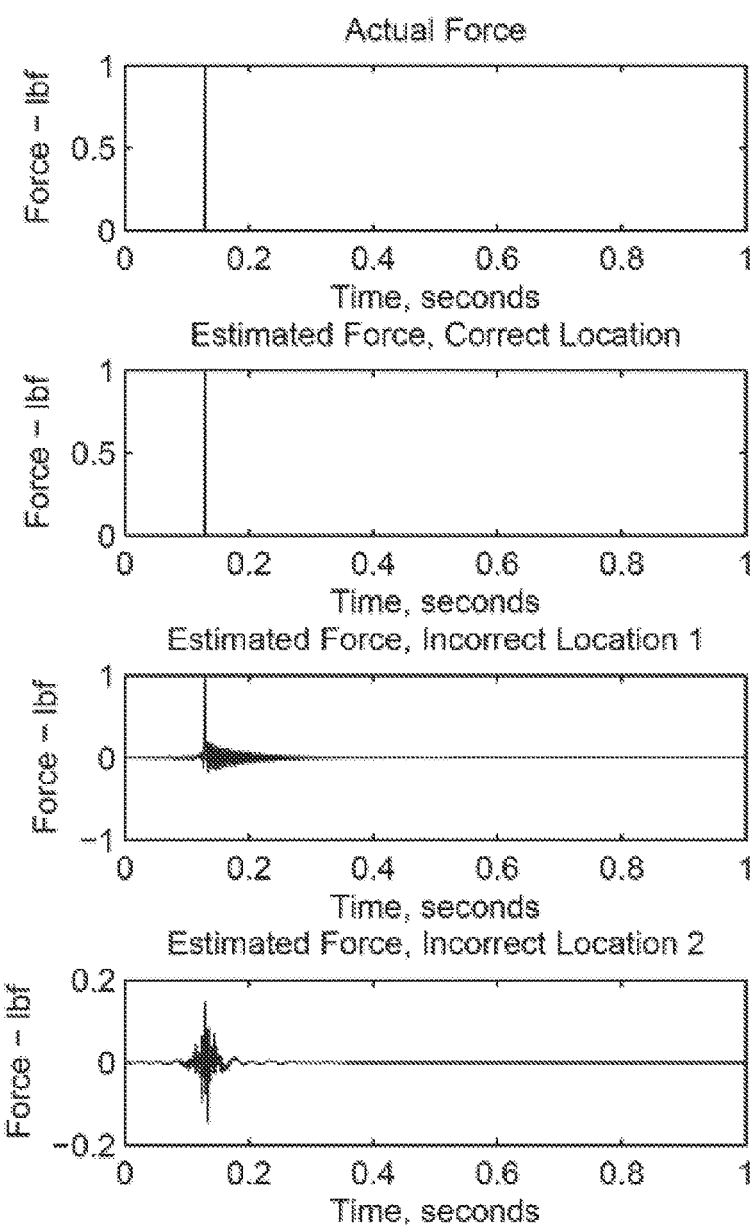
FIG. 13.8A
FIG. 13.8B
FIG. 13.8C
FIG. 13.8D

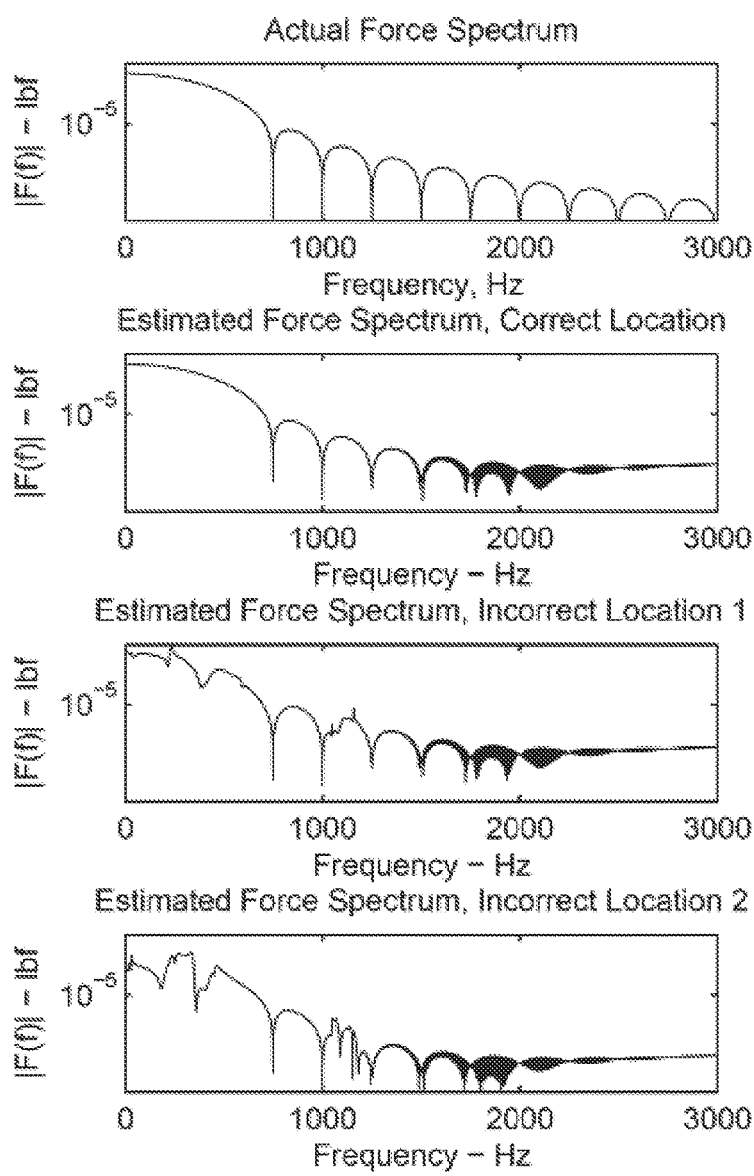
FIG. 13.8E
FIG. 13.8F
FIG. 13.8G
FIG. 13.8H

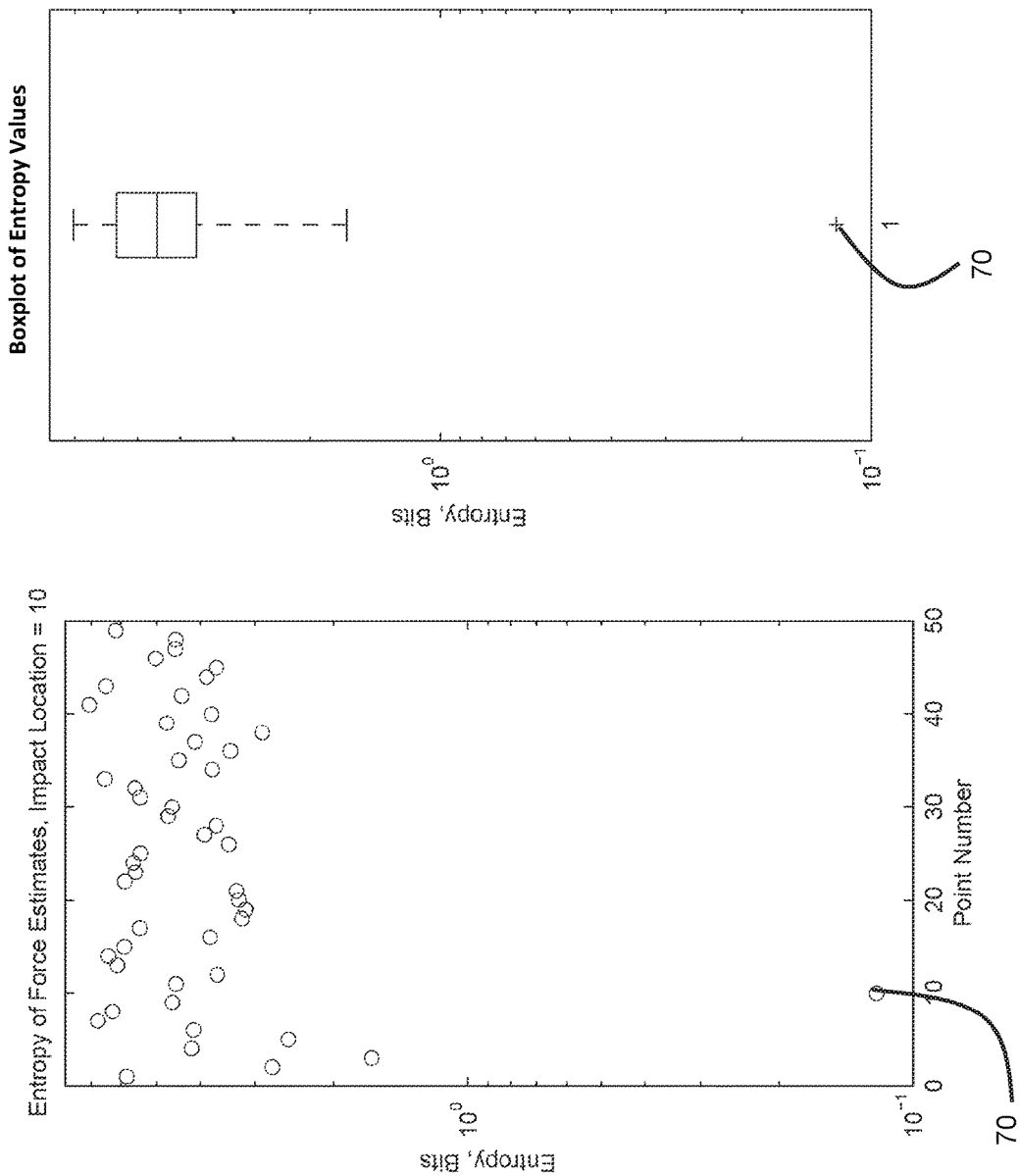
FIG. 13.9B
FIG. 13.9A

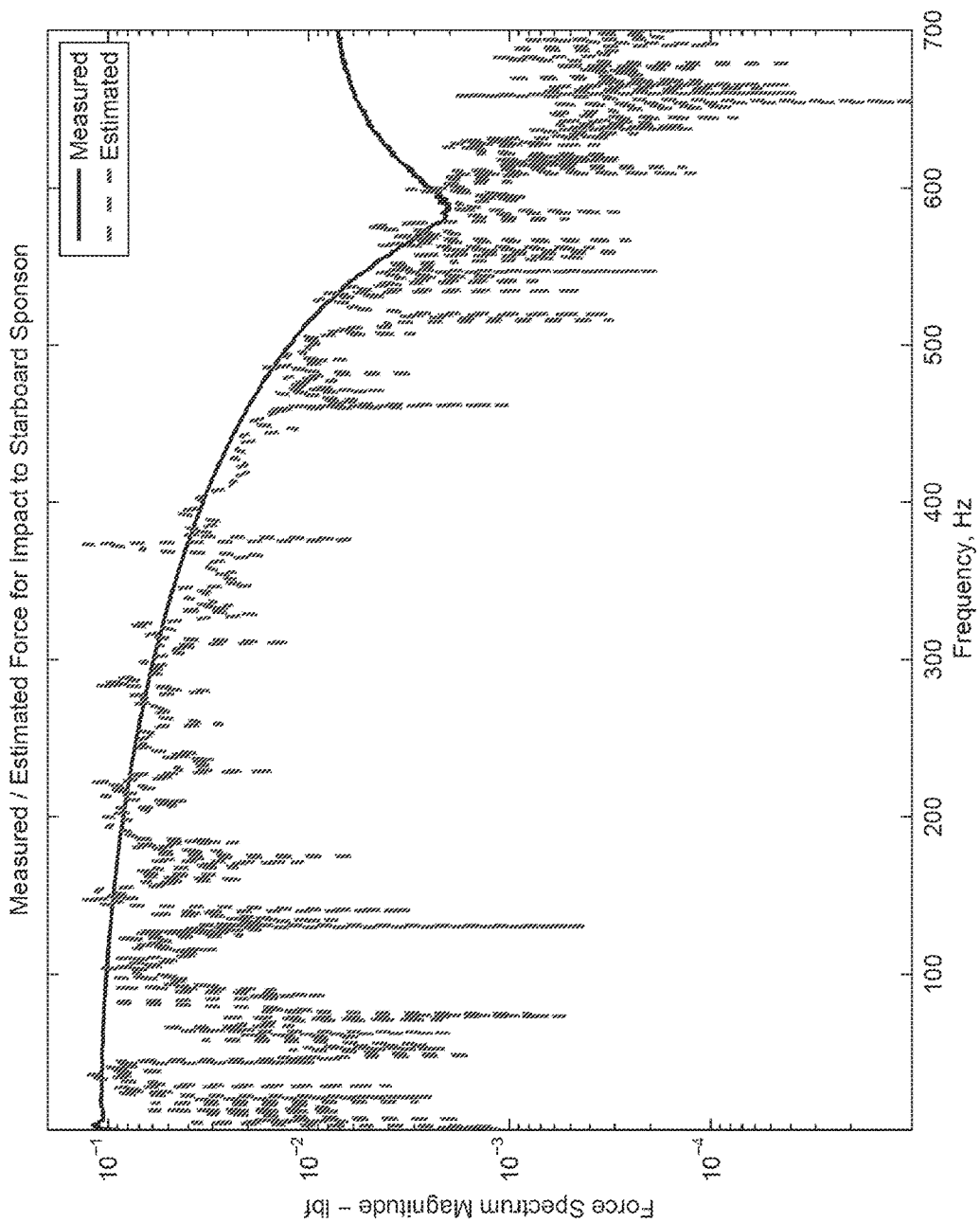
FIG. 14.1

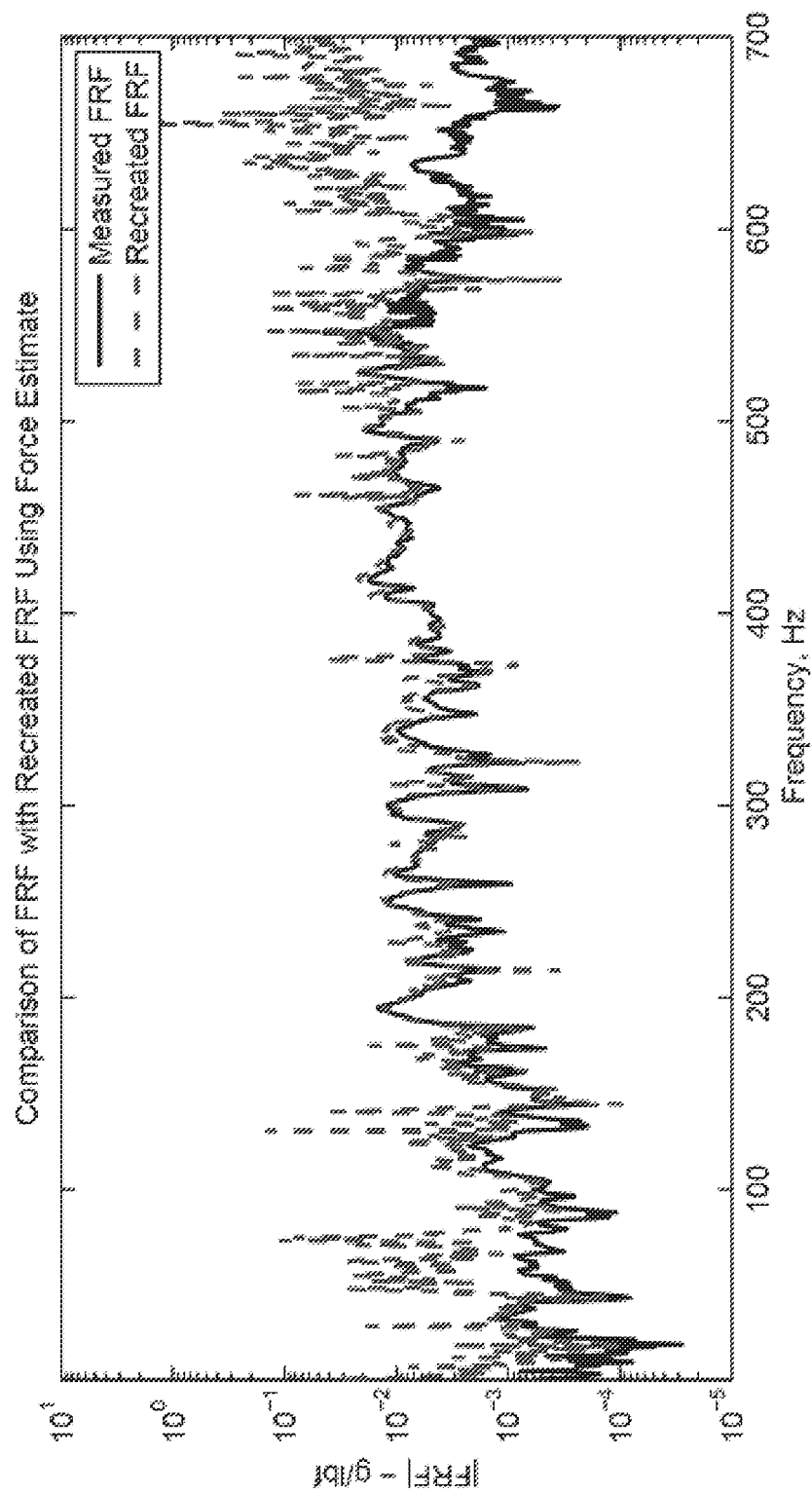
FIG. 14.2A

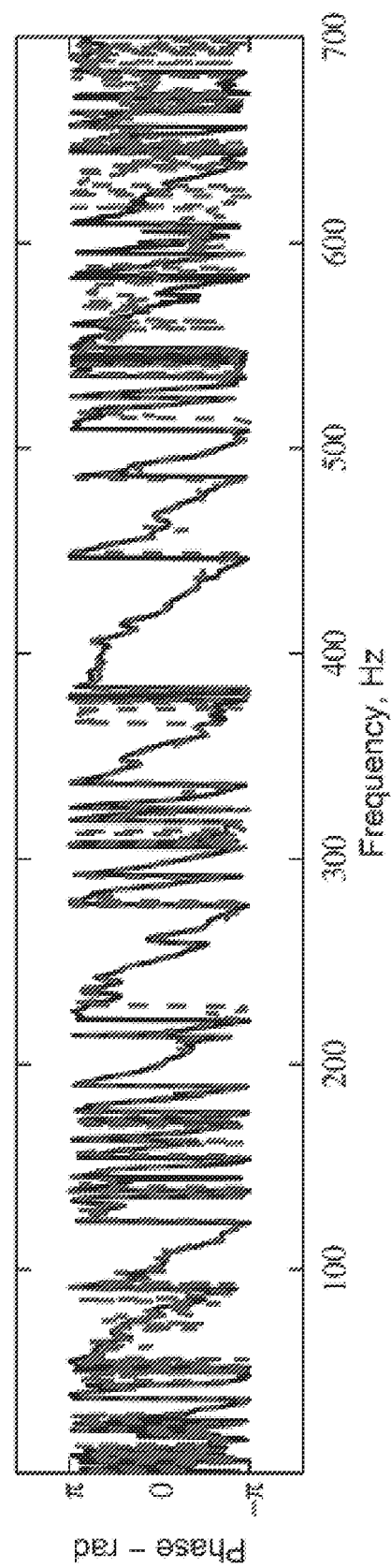
FIG. 14.2B

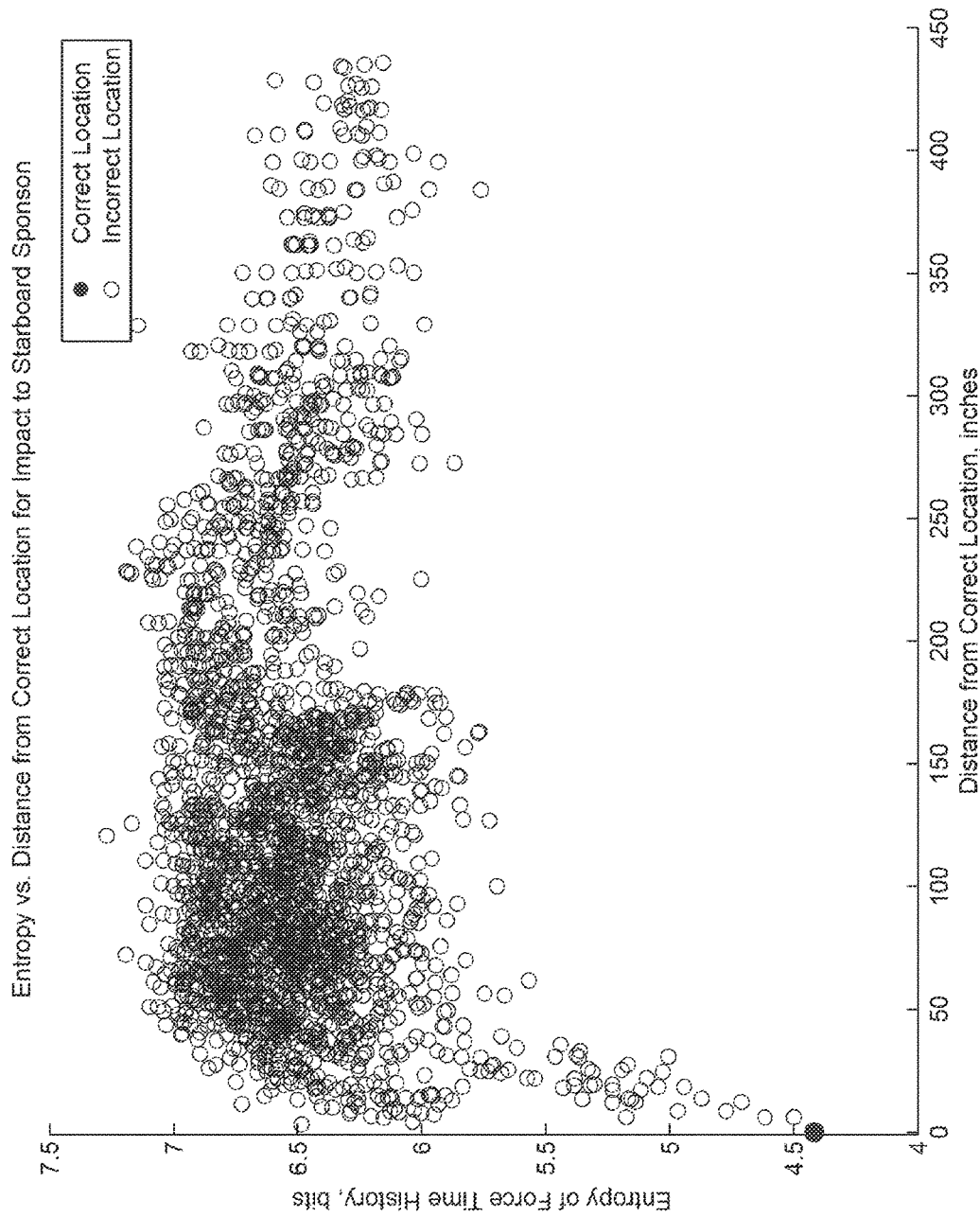
FIG. 14.3

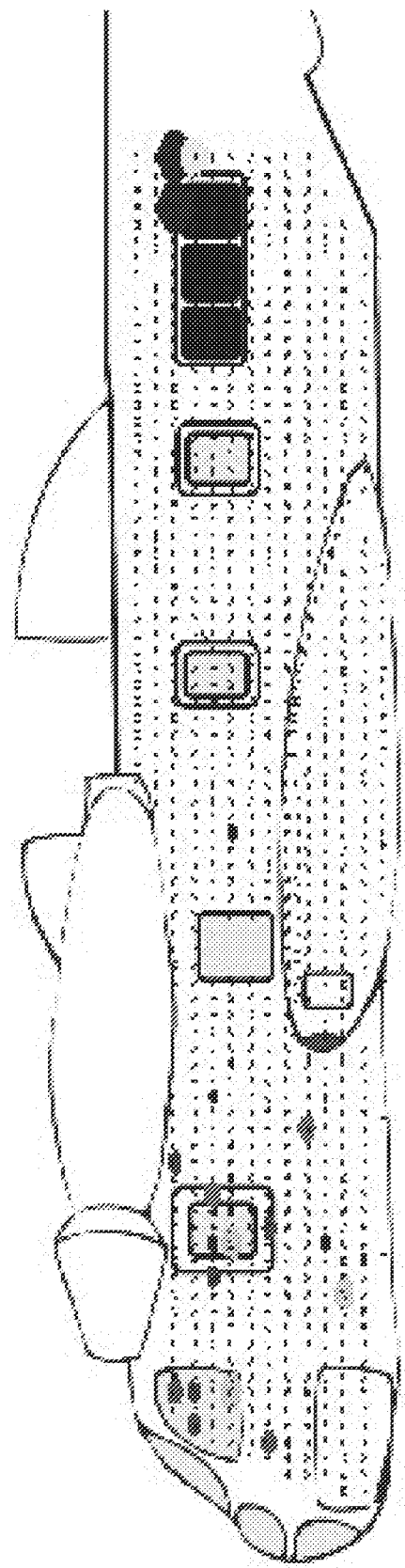
FIG. 14.4

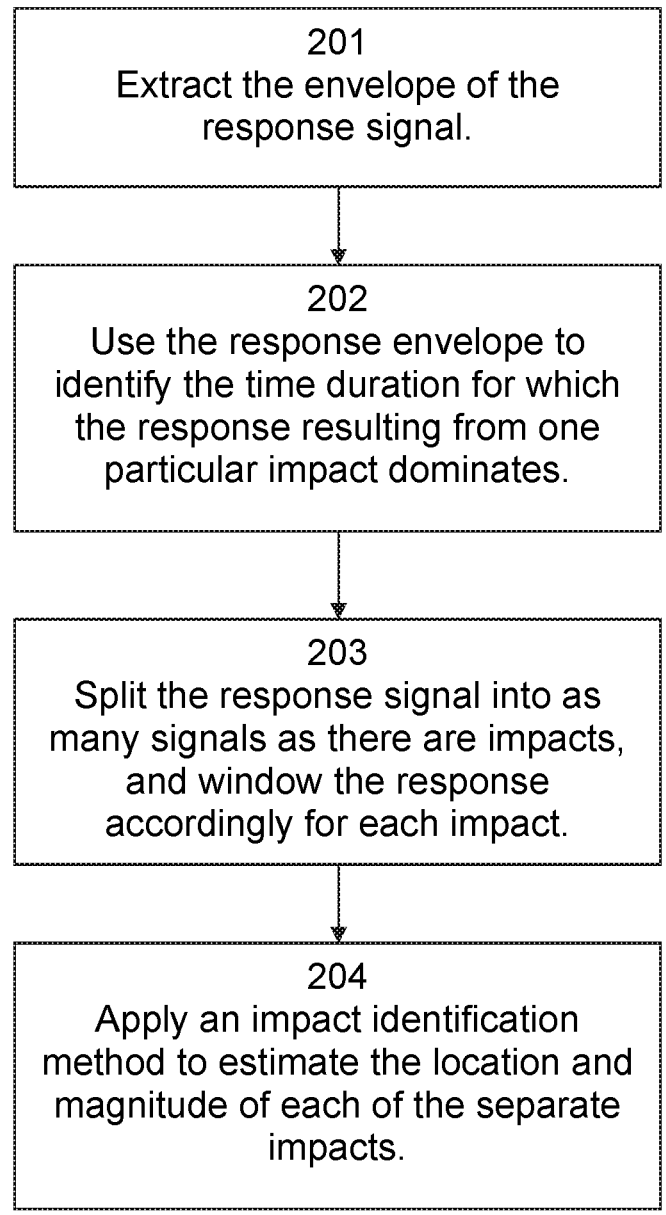
FIG. 14.5A

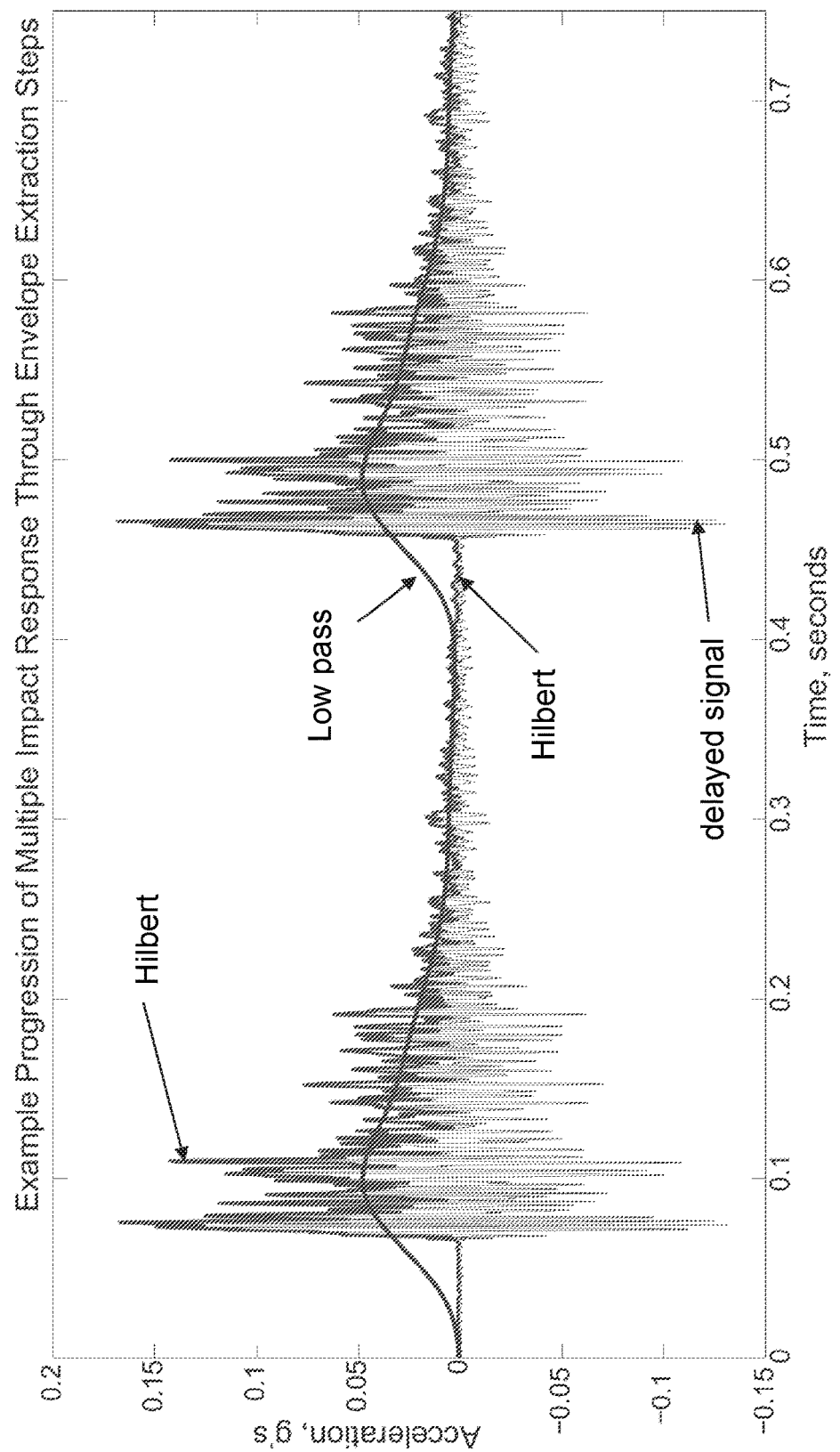
FIG. 14.5B

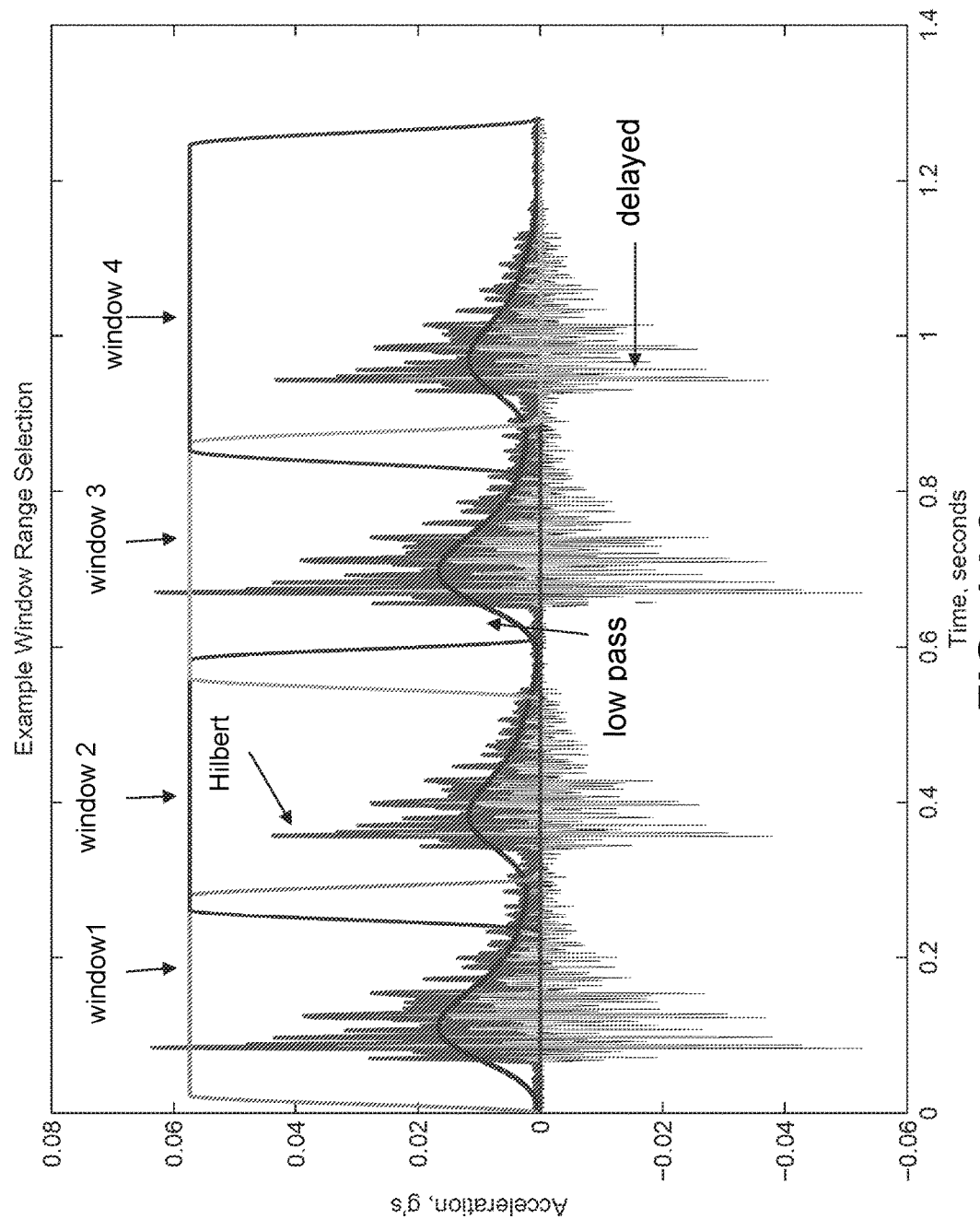
FIG. 14.6

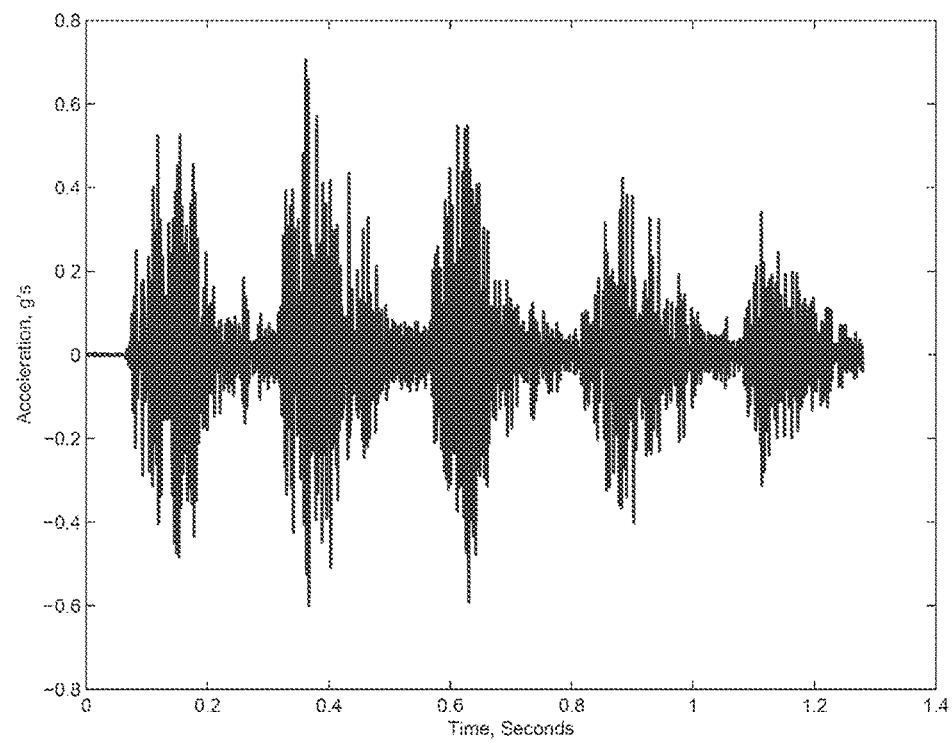
FIG. 14.7
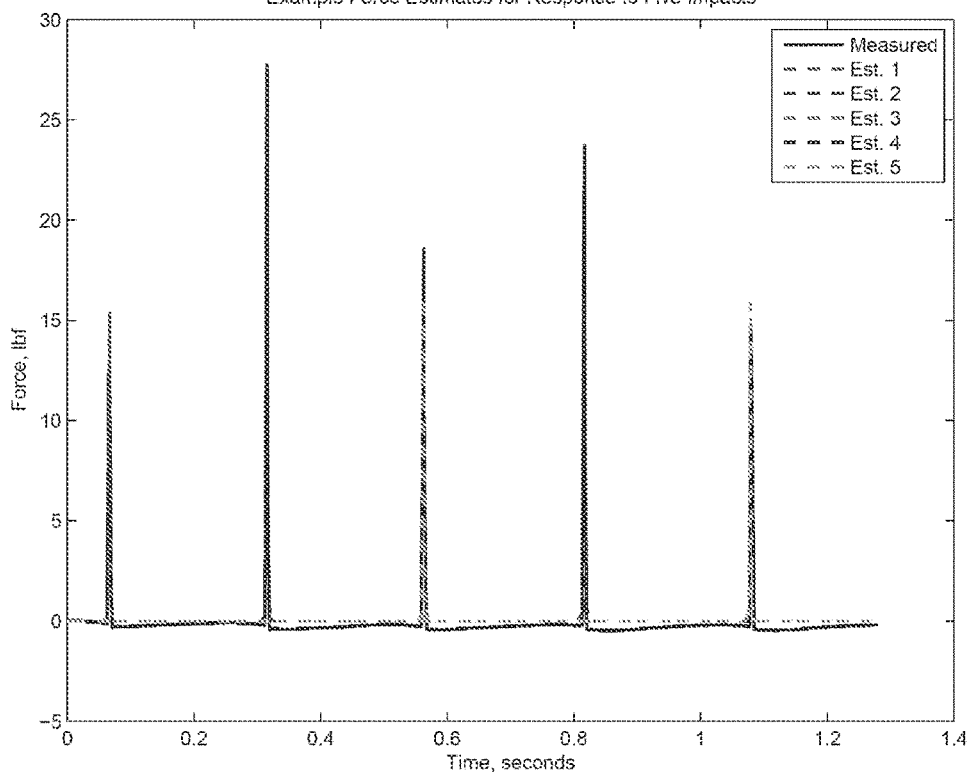
FIG. 14.8

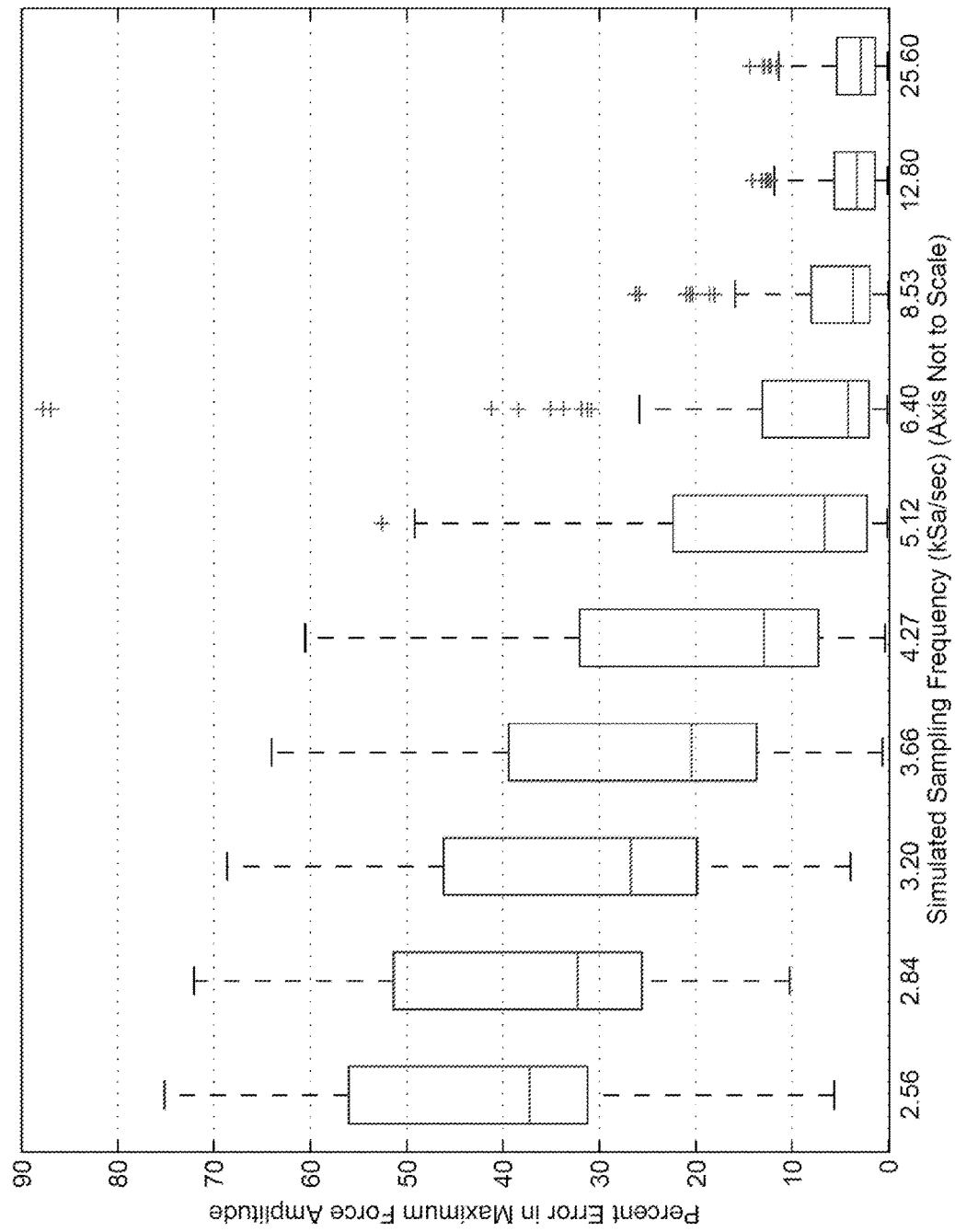
FIG. 15.1

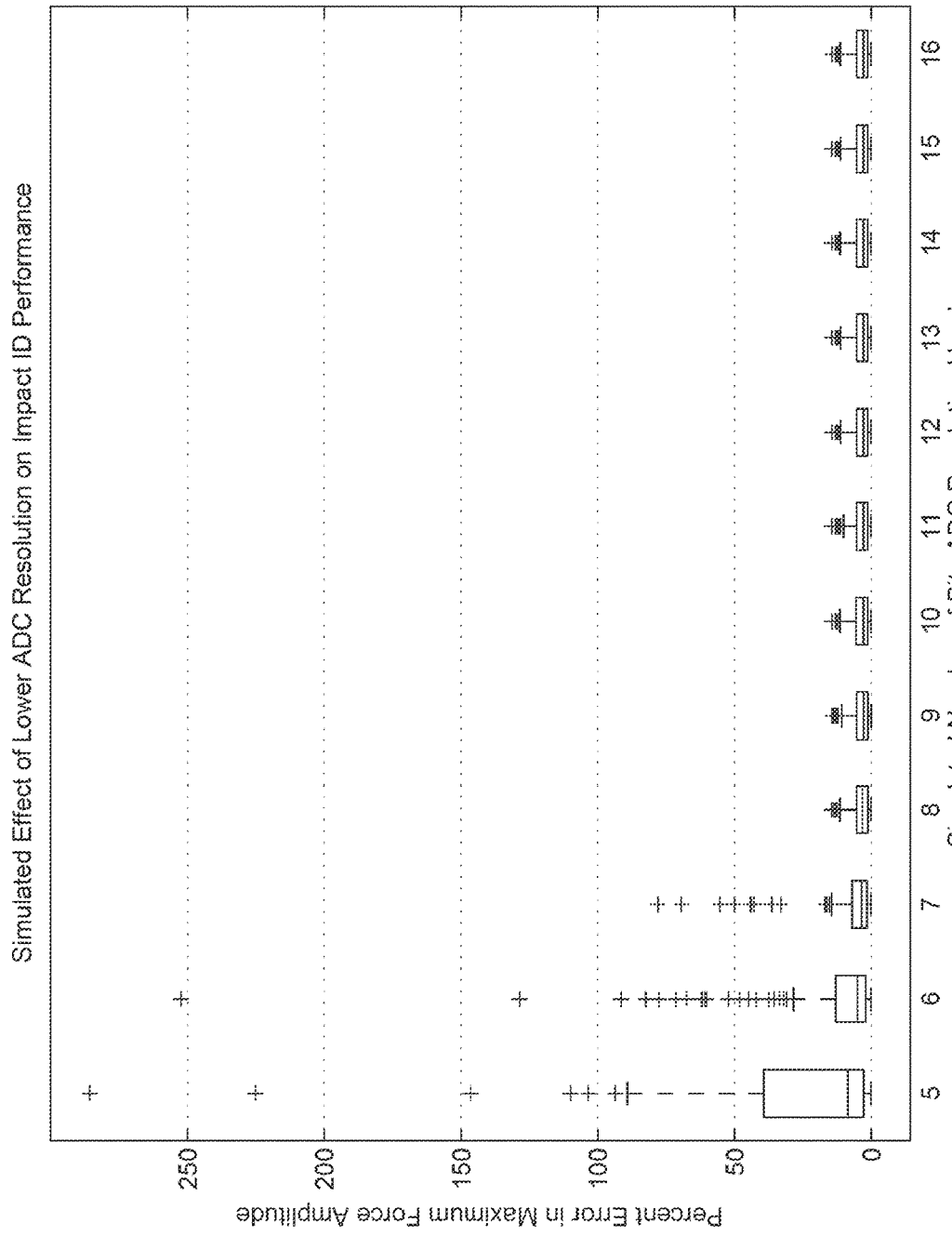
FIG. 15.2

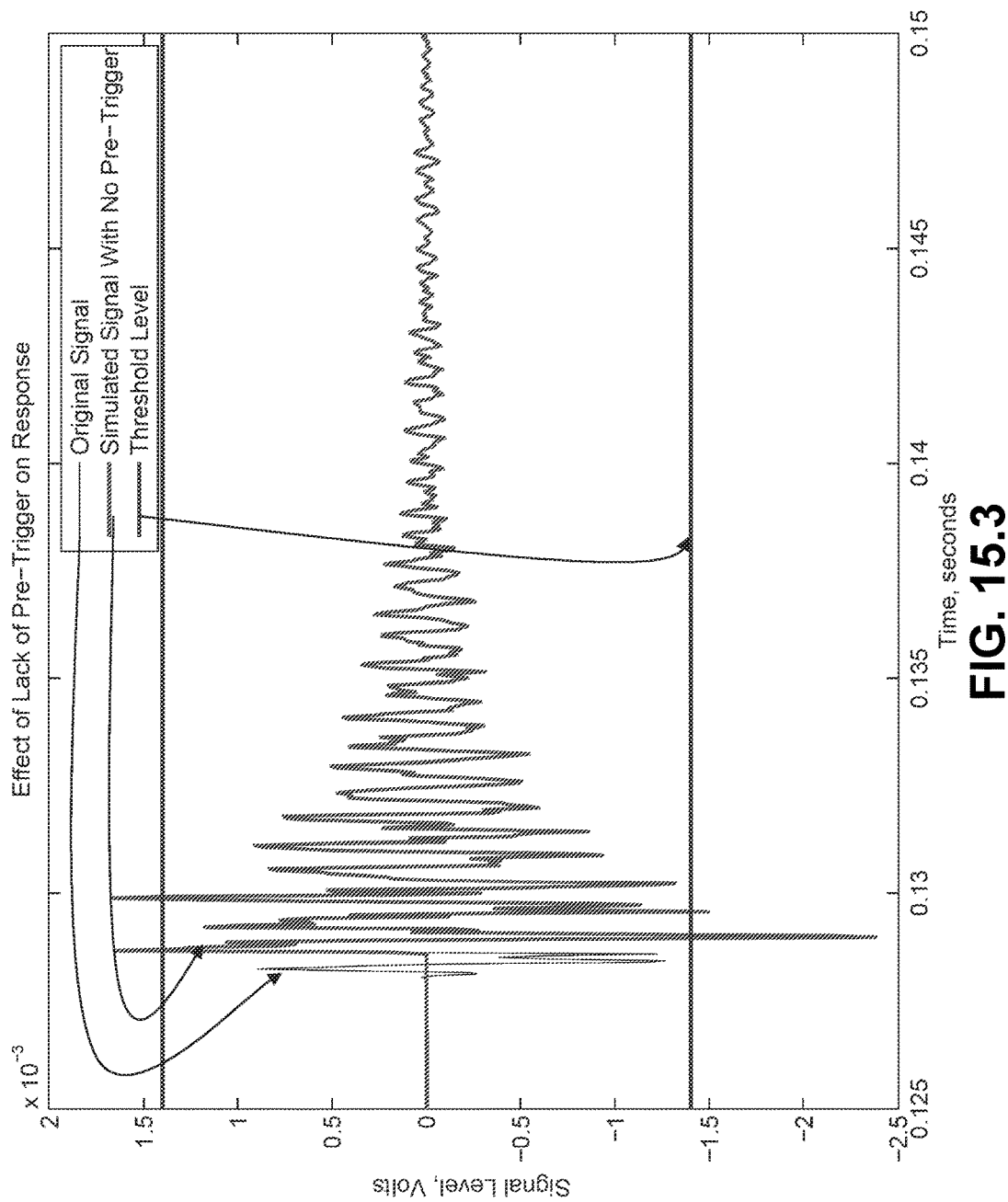
FIG. 15.3

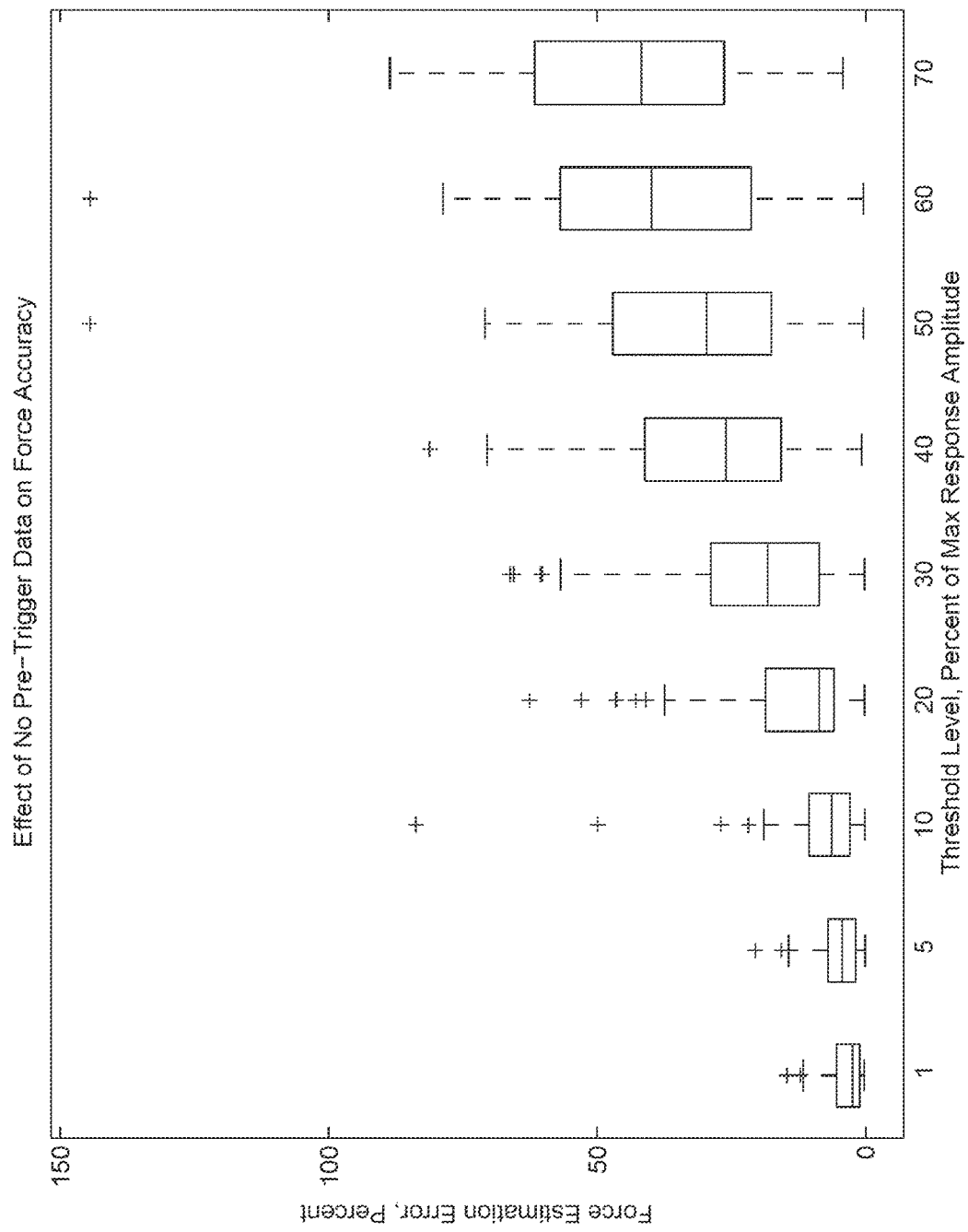
FIG. 15.4

ENTROPY-BASED IMPACT LOAD IDENTIFICATION

CROSS REFERENCE TO RELATED APPLICATIONS

This application is a 371 application of PCT/US2011/058841, filed Nov. 1, 2011, which claims the benefit of priority to U.S. Provisional Patent Application Ser. No. 61/408,915, filed Nov. 1, 2010, entitled IMPACT IDENTIFICATION WITH MINIMAL SENSING, both of which are incorporated herein by reference.

GOVERNMENT RIGHTS

This invention was made with government support under Grant 104371 of Fund 41040000 of Order 8000034263 awarded by the Naval Air Systems Command of the United States Navy. The government has certain rights in the invention.

FIELD OF THE INVENTION

Various embodiments of the present invention pertain to methods and apparatus for detecting damage in structures, and in some embodiments more particularly to sensing damage in composite material structures subjected to impacts.

BACKGROUND OF THE INVENTION

The increasing prevalence of laminated composite materials in aircraft construction has spawned a need for a method that can be implemented in real-time and is not prohibitively time consuming. Impacts to composite structures may cause subsurface damages, not visible to the naked eye, in the form of ply delamination, core crushing and matrix debonding. Current methods of inspection include labor intensive x-ray examinations and subjective coin tap tests, neither of which can be performed while in flight.

Identification methods have been proposed and demonstrated to detect impact magnitudes and locations. However, these methods are restrictive in that they use an accurate first principles-based model of the structure being monitored, large sensor arrays, carefully controlled boundary conditions or a combination of the above.

The heterogeneous nature of the helicopter introduces difficulties with applying the frequency domain location identification methods developed on relatively homogeneous composite specimens. The exterior of the helicopter used as a test specimen has surfaces including retrofitted carbon fiber-reinforced composite honeycomb panels, plastic windows, doors, aluminum skin with rib stiffening, and repaired sections. This wide range of outer panel stiffnesses means impacts' pulse widths, and therefore frequency bandwidths, may vary between impacts at different locations. The widely varying frequency excitation bandwidth of impacts to this heterogeneous structure makes defining a small frequency range of interest to use for comparison difficult.

Various embodiments of the present invention provide novel and nonobvious ways of detecting impact magnitudes and locations.

A critical challenge in fielding composite aerospace structures is the need to locate impact damage that often offers little to no visual indication. The inspection of large composite aircraft using existing methodologies is labor-intensive and costly, but by identifying the severity of impacts through position and force identification of these impacts, inspections could be more focused and potentially more frequent, allowing for a reduction of inspection cost and an increase in safety. To this end, impact identification methods attempt to determine impact force locations and magnitudes. Strategies for using a sparse sensor array allows such a system to be implemented with little hardware, in order to minimize the cost and space requirements of such a system. New entropy-based and randomness-based methods of impact identification are presented, and the effects of several sources of error are addressed. By simulating some of the limitations and challenges of the field environment, the relevant sources of error can be identified and compensated for. Strategies for addressing these issues are presented with two case studies: a composite filament-wound rocket motor casing and a heavy lift helicopter. The randomness-based impact identification method was shown to locate more than 96% of impacts to a helicopter fuselage to either the correct impact point or an adjacent point. Methods for identifying multiple impacts were developed, and impacts acting in rapid succession were located within two grid points of the actual location in 87.6% of cases, with similar average force estimation error to when only one impact acts.

SUMMARY OF THE INVENTION

One aspect of the present invention pertains to a method for estimating a load acting on an object. Some embodiments include measuring a plurality of responses of the object to the unknown load. Other embodiments include calculating a plurality of hypothetical loads each associated with a different one of the plurality of responses. Yet other embodiments include calculating the randomness associated with each of the hypothetical loads.

Another aspect of the present invention pertains to a method of estimating an unknown load acting on an object. Some embodiments include calculating a plurality of hypothetical loads associated with the response of the object to the unknown load, and selecting one or more of the hypothetical loads. Yet other embodiments include calculating a first factor corresponding to the energy of the one hypothetical load. Still others include restricting or filtering the one hypothetical load, calculating a second factor corresponding to the energy of the restricted hypothetical load, and preparing a corrected hypothetical load based on the first factor and the second factor.

Yet another aspect of the present invention pertains to a method for identifying damage to an object. Some embodiments include providing a plurality of time-domain data corresponding to responses of the object to an event. Other embodiments include quantifying the randomness associated with each of the plurality of responses. Yet other embodiments include identifying regions of the object with possible damage based on the quantifying.

Still another aspect of the present invention pertains to a method of estimating an unknown load acting on an object. Some embodiments include determining that the unknown load includes a plurality of separate loads to the object. Yet other embodiments include determining a plurality of time windows, each of the time windows corresponding to a different one of the separate impacts. Still further embodiments include applying the plurality of time windows to the signal to produce a plurality of separated signals, each separated signal corresponding to a different one of the separate loads.

Yet another aspect of the present invention pertains to deriving an empirical model of a structure. Some embodiments include recording the response of the structure to an impact. Other embodiments include using the model to predict a plurality of hypothetical responses. Yet other embodiments include assessing the likelihood of occurrence of each of the hypothetical responses. Still other embodiments include selecting at least one of the hypothetical responses to predict the location of the impact based on the likelihood of occurrence of the one hypothetical response.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

FIG. 2A: On-board data acquisition is implemented with minimal hardware.

FIG. 2B: On-board data acquisition is implemented with minimal hardware.

FIG. 12.1 The first test article considered was a carbon-fiber filament wound rocket motor casing, as seen here.

FIG. 12.2 The rocket motor casing was instrumented with a custom low sensitivity tri-axial shock accelerometer (lower left), as well as a higher sensitivity tri-axial accelerometer (upper right).

FIG. 12.3 A PCB 086C01 modal impact hammer, as illustrated here, was used to apply a measured impulsive force to the test specimen.

FIG. 12.4A Frequency response function estimates for an example impact location on a canister show lightly damped resonances with reasonably good coherence values.

FIG. 12.4B Frequency response function estimates for an example impact location on a canister show lightly damped resonances with reasonably good coherence values.

FIG. 12.5 Average force auto power spectra for impacts to each grid point on an example canister show consistently broadband excitation.

FIG. 12.6 The fuselage of a retired heavy lift helicopter is used as a test article.

FIG. 12.7 The modal grid of 1122 impact locations is superimposed on an illustration of the port side of the fuselage.

FIG. 12.8A Numerous materials of widely varying properties were used in the construction of this helicopter, including aluminum with riveted stiffening ridges.

FIG. 12.8B Numerous materials of widely varying properties were used in the construction of this helicopter, including aluminum with retrofitted carbon-fiber reinforced composite panels 85.

FIG. 12.8C Numerous materials of widely varying properties were used in the construction of this helicopter, including aluminum with plastic windows.

FIG. 12.8D Numerous materials of widely varying properties were used in the construction of this helicopter, including aluminum with fiberglass portions.

FIG. 12.9 Impacts to different points on the fuselage excite a widely varying frequency bandwidth, as shown from these example force auto-power spectra.

FIG. 12.10A These example FRF estimates and coherence plots show the fairly low coherence values that were typical of measurements on the helicopter.

FIG. 12.10B These example FRF estimates and coherence plots show the fairly low coherence values that were typical of measurements on the helicopter.

FIG. 12.11 The port side sponson is shown here with the re-fuelling door open.

FIG. 12.12 This aluminum plate was tested so that modal parameters representative of a metal plate could be used in an analytical model.

FIG. 13.1 An impact identification process is illustrated here, according to one embodiment of the present invention.

FIG. 13.2 A cantilevered beam, as illustrated here, is used to explain the discretization process of a continuous structure.

FIG. 13.3 This discrete representation of the example cantilevered beam is in a form that can be characterized by measurements alone.

FIG. 13.4 The example beam structure is shown in a configuration representative of an impact identification setup.

FIG. 13.5 Entropy for a set of unfair coin tosses as a function of the probability of heads is a shown as a simple example for explaining entropy.

FIG. 13.6 This consistency diagram shows the consistency of modal parameter estimates for the square plate with increasing model order.

FIG. 13.7 Measured and synthesized frequency response functions for the test plate: (-) measured and ( - - - ) synthesized.

FIG. 13.8A Estimated forces in the time domain and the magnitudes of the corresponding spectra in the frequency domain for several example locations, along with the actual force input.

FIG. 13.8B Estimated forces in the time domain and the magnitudes of the corresponding spectra in the frequency domain for several example locations, along with the actual force input.

FIG. 13.8C Estimated forces in the time domain and the magnitudes of the corresponding spectra in the frequency domain for several example locations, along with the actual force input.

FIG. 13.8D Estimated forces in the time domain and the magnitudes of the corresponding spectra in the frequency domain for several example locations, along with the actual force input.

FIG. 13.8E Estimated forces in the time domain and the magnitudes of the corresponding spectra in the frequency domain for several example locations, along with the actual force input.

FIG. 13.8F Estimated forces in the time domain and the magnitudes of the corresponding spectra in the frequency domain for several example locations, along with the actual force input.

FIG. 13.8G Estimated forces in the time domain and the magnitudes of the corresponding spectra in the frequency domain for several example locations, along with the actual force input.

FIG. 13.8H Estimated forces in the time domain and the magnitudes of the corresponding spectra in the frequency domain for several example locations, along with the actual force input.

FIG. 13.9A shows the entropy values resulting from the recreation of various time histories according to one embodiment of the present invention.

FIG. 13.9B shows the entropy values from FIG. 13.9A shown in a box plot.

FIG. 14.1 The estimated force spectrum for an impact to the starboard sponson ( - - - ) is compared to the measured value (-).

FIG. 14.2A The measured (-) and estimated ( - - - ) frequency response functions for an impact to the starboard sponson are compared for the correct location, using the transverse direction of the middle accelerometer as a reference.

FIG. 14.2B The measured (-) and estimated ( - - - ) frequency response functions for an impact to the starboard sponson are compared for the correct location, using the transverse direction of the middle accelerometer as a reference.

FIG. 14.3 The entropy of each estimated force time history, which is used to decide the correct location, is shown for each location, plotted against the distance from the actual impact location.

FIG. 14.4 Impact location identification error for the port side of the fuselage is illustrated here, with dot size proportional to position identification error.

FIG. 14.5A shows a data processing algorithm according to one embodiment of the present invention.

FIG. 14.5B Each aspect of one envelope extraction process is shown: the original signal (blue), the calculated envelope (green), and the low-pass filtered envelope (red).

FIG. 14.6 The window selection process is illustrated here for an example response due to four impacts.

FIG. 14.7 This example response is due to five impacts to the fuselage in quick succession.

FIG. 14.8 Force estimates according to one embodiment of the present invention for the five identified impacts are compared to the measured force value here.

FIG. 15.1 The effect of lower sampling frequency on peak force estimation is illustrated with this box plot, according to one embodiment of the present invention.

FIG. 15.2 Peak force identification error is shown vs. number of effective bits ADC resolution, for 5-16 bits, according to one embodiment of the present invention.

FIG. 15.3 The simulated signal without a pre-trigger is shown here with the original signal. Red—threshold level, green—simulated signal with no pretrigger, and blue—the original signal, according to one embodiment of the present invention.

FIG. 15.4 Effect of increasing trigger threshold level is simulated for data acquisition without a pre-trigger, according to one embodiment of the present invention.

Figure 1A:
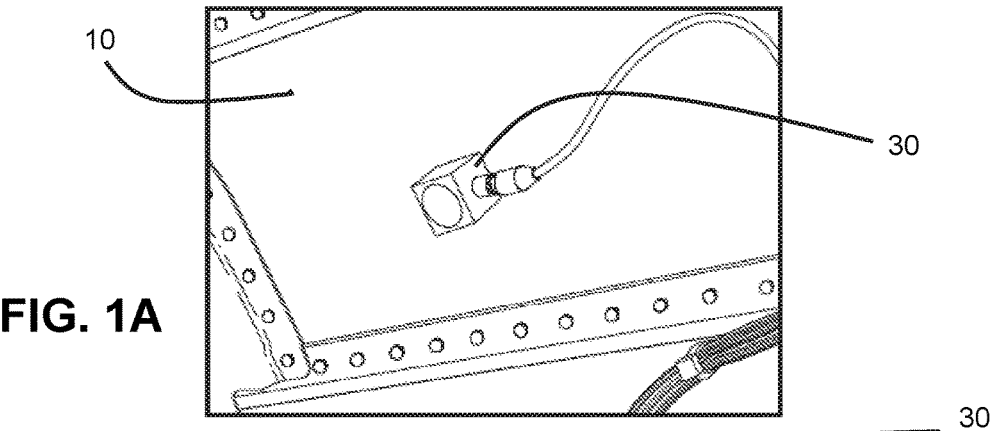
FIG. 1A shows an Accelerometer-mounting detail on the tail of a structure.

| SYMBOLS | |
|---|---|
| $a(t)$ | Acceleration in Time Domain |
| $A(\omega)$ | Acceleration Spectrum |
| $A_{pqr}$ | Residue |
| $A^+$ | Pseudoinverse of Matrix A |
| $\gamma^2_{\overline{pq}}$ | Ordinary Coherence |
| $D_f$ | Frequency Step |
| $D_t$ | Sampling Time Stop |
| $f$ | Frequency, Hz |
| $f_n$ | $n^{th}$ Frequency Step |
| $f_s$ | Sampling Frequency |
| $f_d$ | Damped Natural Frequency (Hz) |
| $f(t)$ | Force in Time Domain |
| $F(\omega)$ | force Spectrum |
| $\hat{F}$ | Estimated Force Spectrum |
| $h(t)$ | Impulse Response |
| $H_{pq}(j\omega)$ | Frequency Response Function for Output p, Input q |
| $H$ | Entropy |
| $I$ | Information |
| $N_i$ | Number of Input Measurement Degrees-of-Freedom |
| $N_o$ | Number of Output Measurement Degrees-of-Freedom |
| $N_f$ | Number of Discrete Spectral Lines |
| $\omega$ | Frequency, rad/s |
| $\omega_d$ | Damped Natural Frequency (rad/s) |
| $p_i$ | Probability of Event i |
| $\{\psi_r\}$ | Modal Vector |
| $t$ | Time |
| $t_n$ | $n^{th}$ Time Step |
| $\zeta$ | Damping Ratio |

ABBREVIATIONS

ADC Analog to Digital Converter
CFRP Carbon-Fiber Reinforced Polymer
CMIF Complex Mode Indicator Function
DAQ Data Acquisition
DFT Discrete Fourier Transform
DOF Degree-of-Freedom
FFT Fast Fourier Transform
FIR Finite Impulse Response
FRF Frequency Response Function
IDFT Inverse Discrete Fourier Transform
IFFT Inverse Fast Fourier Transform
IIR Infinite Impulse Response
IRF Impulse Response Function
MAC Modal Assurance Critereon
MIMO Multiple Inputs, Multiple Outputs
NDE Non-Destructive Evaluation
PTD Poly-Reference Time Domain
SIMO Single Inputs, Multiple Outputs
SVD Singular Value Decomposition

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims.

The use of an N-series prefix for an element number (NXX.XX) refers to an element that is the same as the non-prefixed element (XX.XX), except as shown and described thereafter The usage of words indicating preference, such as "preferably," refers to features and aspects that are present in at least one embodiment, but which are optional for some embodiments. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. This description convention also applies to the use of prime ('), double prime ("), and triple prime ('") suffixed element numbers. Therefore, it is not necessary to describe the features of 20.1, 20.1', 20.1", and 20.1'" that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

Some portions of this documents will refer to the "helicopter" or the "casing" or the "plate." It is to be understood that all such statements pertaining to the use of a specific structure are by way of example only, and are not to be construed as limiting. The methods and apparatus disclosed herein are applicable to any object, and preferably to complex structures 10, including by way of example aircraft, vehicles of any type, buildings, and the like.

This application incorporates in entirety by reference PCT patent application No. PCT/US2010/029660, filed Apr. 1, 2010, titled IDENTIFICATION OF LOADS ACTING ON AN OBJECT, filed in the name of the Purdue Research Foundation.

Composite materials, particularly fiber reinforced polymers, are increasingly used for aerospace structures 10 because these materials offer significant advantages over traditional metallic components. Specifically, composite materials such as carbon fiber reinforced polymers (CFRP's) have improved specific strength and stiffness compared to other materials, and have desirable corrosion and fatigue properties as compared to metals such as aluminum and steel. Furthermore, advances in composite fabrication have made the manufacturing of components from composites cost competitive with manufacturing using metals.

One aspect of composites in aircraft structures is the susceptibility to impact damage, and the difficulty in evaluating the damage sustained due to impacts. Damaging low-velocity impacts can be sustained from sources varying from debris during takeoff and landing to tool drops during maintenance. As compared to metals, composites have complex and often difficult to detect failure modes, and impact damage to composite structures results in a much more pronounced effect on the load carrying capacity of the structure. Impact damage to composites can result in sub-surface damage that significantly compromises the structure without being visually apparent. Sub-surface damage in sandwich composite materials such as ply interlaminar delamination, face sheet debonding, and core crushing can significantly reduce the residual strength of the material, particularly in compression. For example, some tests have shown that low velocity impact damage can result in a reduction in compressive strength of up to 50% due to inter-ply delamination, a damage mechanism that is not evident from the surface.

Therefore, the prevention and mitigation of impact damage in composite materials is a critical need in order to fully realize the benefits that these materials offer. Extensive work has been done to improve the impact resistance of composites, but in spite of these improvements, it is still necessary to mitigate the effects of this damage when it occurs. Much of the damage to composites is attributed to impacts. For example, a study of composite elevator damage on a commercial aircraft indicated that over half of the problems found were due to impact damage. Various methods of inspection and non-destructive evaluation of composite components can identify damaged regions, but most inspection methods are labor intensive and subjective. The cost of implementing these methods for wide-area inspections of composite aircraft is high, and when subjective inspection methods are used, human factors including fatigue and loss of alertness during tedious inspections when damage is rare can compromise the effectiveness of inspection methods.

A system according to one embodiment of the present invention can identify the location of potentially damaging impacts and can reduce the need for wide area inspections, because locations of interest could be considered as needed, rather than considering the entire aircraft at once. More focused inspections also have the potential to reduce the human errors associated with wide-area inspections, because the operator would know that damage in a certain location was likely. One study estimated that an autonomous impact sensing system on a composite fighter aircraft could reduce inspection time by as much as 50%. Furthermore, a survey of potential end users of aircraft structural health monitoring systems identified impact damage detection as the top inspection target in composite structures that would benefit from structural health monitoring solutions.

In a validation simulation, 93% of impacts to the port side of the aircraft are correctly located using response data from three impacts per grid point. Force and location accuracy are shown to be somewhat independent of distance from the sensors. A real-time implementation of this system shows the ability to locate impacts with approximately 0.5 seconds of processing time.

Yet another embodiment of the present invention pertains to a method to compensate for multiple impacts that occur in relatively quick succession, such as a plurality of separate impacts, wherein the measured response from each impact overlaps (i.e., does not die out) with the onset of the next impact. The procedure developed mitigates the effects of quickly occurring impacts based on identifying the portions of the response signal that are a result of particular impacts, and then using those identified time ranges to isolate the response due to each impact, and consider those responses separately. In some embodiments, when a response due to multiple impacts is detected, the envelope of the response signal is extracted and low-pass filtered, and then intervals for each impact are identified based on this filtered envelope. By isolating the response to each impact in this manner, the magnitude and location of impacts that act at different locations on the structure in quick succession can be effectively identified.

One embodiment of the present invention shows that inversion based minimal sensing techniques can be implemented on a large scale without a substantial increase in the sensor density. A novel time domain location identification technique is implemented to address the problems that come from a large scale model. Using three sensors, 93% of validation impacts on the port side of a heavy lift helicopter are correctly identified, and 90% of impacts on the starboard side are correctly located.

In one embodiment of the present invention there is an algorithm applied to a helicopter fuselage 10, with 3 reference tri-axial accelerometers 30, and modal grid established on both sides of helicopter with 6" spacing. On one side of the helicopter, 93% point identification accuracy of impulsive loads applied with hammer in validation simulation was achieved. Some embodiments of the present invention include real time monitoring system 20 and graphical user interface 40 developed for a structure, which notifies users of impacts, magnitude of impacts, and location of impacts on a schematic of helicopter. Although reference will be made to apparatus and methods used on a helicopter, it is appreciated that the various embodiments described herein pertain to any type of vehicle, and further apply to non-vehicle structures.

The impact identification algorithm in one embodiment includes indirect force estimation by inversion of information calculated from training data. A set of assumptions is applied to formulate an overdetermined inverse problem suitable for inversion with a pseudoinverse to solve for the best fit estimate of the forcing function. With no assumptions or constraints applied, the inverse problem is underdetermined. An infinite number of forces act at infinitely many locations, which when multiplied by a frequency response function that is continuous in frequency and position, a continuous acceleration signal in frequency is obtained. Equation (1) shows this initial problem, and the following equations show the development of the overdetermined inverse problem from this initially infinitely underdetermined problem. This example shows the approach for $N_{ch}$ acceleration response channels.

$$A_n(f) = \int_{z_{min}}^{z_{max}} \int_{y_{min}}^{y_{max}} \int_{x_{min}}^{x_{max}} H_n(f,x,y,z) F(f,x,y,z) dx\, dy\, dz$$
where $n$ is output acceleration measurement, $f$
for $n = 0, 1, \ldots N_{ch}$ (1)

Limiting the frequency band to $\{0, f_{max}\}$ with $N_f$ frequency points giving a frequency resolution $\Delta_f$, and defining M discrete points where a force can be applied, this infinitely underdetermined system can be reduced to $N_f$ systems of equations, shown in (2).

$$\begin{bmatrix} A_1(n\Delta_f) \\ A_2(n\Delta_f) \\ \vdots \\ A_{N_{ch}}(n\Delta_f) \end{bmatrix}_{N_{ch} \times 1} = \qquad (2)$$

$$\begin{bmatrix} H_{11}(n\Delta_f) & H_{12}(n\Delta_f) & \ldots & H_{1M}(n\Delta_f) \\ H_{21}(n\Delta_f) & H_{22}(n\Delta_f) & \ldots & H_{2M}(n\Delta_f) \\ \vdots & \vdots & \vdots & \vdots \\ H_{N_{ch}1}(n\Delta_f) & H_{N_{ch}2}(n\Delta_f) & \ldots & H_{N_{ch}N}(n\Delta_f) \end{bmatrix}_{N_{ch} \times M} \begin{bmatrix} F_1(n\Delta_f) \\ F_2(n\Delta_f) \\ \vdots \\ F_M(n\Delta_f) \end{bmatrix}_{M \times 1}$$

for $n = 0, 1, 2, \ldots N_f$

As stated, equation (2) represents a set of $N_f$ systems of equations, which are underdetermined for $M > N_{ch}$, that is when there are more input degrees of freedom than there are output degrees of freedom. If this set of systems of equations was not underdetermined, it would solve for the frequency spectrum of forces applied at each discrete input point. For an impact at one location, all but one of these force spectrums should be close to zero. Rather than trying to calculate M forces, M−1 of which should be small for the single impact situation considered, another estimate can be found by assuming there is one force input point. Assuming that a forcing function acts at single point allows for a set of overdetermined systems of equations to be formulated, which is suitable for using a pseudoinverse to minimize the error between the estimates from each acceleration channel. Equation (3) shows this set of equations.

$$\begin{bmatrix} A_1(0) & A_1(\Delta_f) & \ldots & A_1(n\Delta_f) \\ A_2(0) & A_2(\Delta_f) & \ldots & A_2(n\Delta_f) \\ \vdots & \vdots & \ldots & \vdots \\ \vdots & \vdots & \ldots & \vdots \\ \vdots & \vdots & \ldots & \vdots \\ A_{N_{ch}}(0) & A_{N_{ch}}(\Delta_f) & \ldots & A_{N_{ch}}(n\Delta_f) \end{bmatrix}_{(N_{ch} \times N_f)} = \quad (3)$$

$$\begin{bmatrix} H_{1k}(0) & H_{1k}(\Delta_f) & \ldots & H_{1k}(n\Delta_f) \\ H_{2k}(0) & H_{2k}(\Delta_f) & \ldots & H_{2k}(n\Delta_f) \\ \vdots & \vdots & \vdots & \vdots \\ \vdots & \vdots & \vdots & \vdots \\ \vdots & \vdots & \vdots & \vdots \\ H_{N_{ch}k}(0) & H_{N_{ch}k}(\Delta_f) & \ldots & H_{N_{ch}k}(n\Delta_f) \end{bmatrix}_{(N_{ch} \times N_f)}$$

$$\begin{bmatrix} F_k(0) & 0 & \ldots & \ldots & \ldots & 0 \\ 0 & F_k(\Delta_f) & 0 & \ldots & \ldots & 0 \\ \vdots & 0 & \ddots & & & \vdots \\ \vdots & \vdots & & \ddots & & \vdots \\ \vdots & \vdots & & & \ddots & \vdots \\ 0 & 0 & \ldots & \ldots & \ldots & F_k(n\Delta_f) \end{bmatrix}_{(N_f \times N_f)}$$

for $k = 1, 2, \ldots, M$

Equation (3) is abbreviated $[A]=[H_k][F_k]$. The pseudoinverse of $[H_k]$ is found for input points k, denoted $[H_k]^+$. The pseudoinverse computation can be done in advance of monitoring the helicopter, making the estimation of force spectrums from a measured acceleration signal a simple matrix product, which is quickly calculated. This matrix product is shown in equation (4).

$$[\hat{F}_k]=[H_k]^+[A], \text{ for } k=1,2,\ldots,M \quad (4)$$

Applying equation (4) to a measured acceleration signal yields M estimates of the force spectrum, each being the one-sided force spectrum that minimizes the error in (3) assuming that the force happened at each spatial point. The location that the force actually acted on is now estimated by analyzing these force estimates. The force spectrum estimate is the diagonal of the $\hat{F}_k$ matrix shown above, and the inverse discrete Fourier transform of the two-sided force spectrum brings the force estimate into the time domain, as shown in equation (5).

$$\{\hat{F}_k(t)\}=IDFT(\text{diag}([\hat{F}_k])), \text{ for } k=1,2,\ldots,Mm \quad (5)$$

With M estimated force-time histories, one for each possible input location, a method according to one embodiment is determined for finding which force-time history most likely corresponds to the actual input location. Following the assumption of an impulsive force, the actual force-time history should be nearly zero for a majority of the time period, with one or more sharp concentrated bursts of energy. When the force is estimated for the correct input location, the estimated force matches this assumption relatively well. When the force is estimated at an incorrect location, the recreated force-time history estimate does not show one sharp isolated pulse, but a more diffuse signal with energy from the actual excitation spread out in time in a disorganized pattern around the time of the actual impulse. A calculation of how ordered or random each of the hypothetical force estimates is reveals which location the force most likely occurred at. One calculation for signal entropy is shown in (6) and (7).

$$H(x) = -\sum_{i=1}^{N} p(x_i)\log_{10}(p(x_i)) \quad (6)$$

where x is a set of random phenomena $\{x_1, x_2, \ldots, x_N\}$, and $p(x_i)$ is a probability of random phenomenon $x_i$ $$p(x_i)=(x_i)^2/\Sigma_{i=1}^{N}(x_i)^2 \quad (7)$$

In some embodiments of the present invention this principle is applied for identifying the signal that actually corresponds to an impulsive forcing function rather than the incorrect force signals. Although equations (6) and (7) refer to calculation of entropy in a signal, various embodiments of the present invention are not so constrained, and include any method for calculating the randomness of the various hypothetical responses.

Force-time history estimates for the input degrees of freedom that the force was not applied at contain a large amount of energy leakage in time and noise as a result of finding a solution to an equation that does not represent the physical situation that generated the measured acceleration measurements. Therefore, for an impulsive forcing function, the force-time history that has the lowest calculated signal entropy corresponds to at least one likely location of impact. In other words, the estimate for the correct location generates an ordered, least random recreated force-time history. This signal entropy of each of the recreated force-time histories is calculated, and the input degree of freedom with the least force signal entropy is identified as the location of impact. It is also appreciated that in various embodiments it is useful to identify those locations having calculated entropies (or calculated randomness factors) that are in excess of a predetermined number, such that a plurality of locations can be excluded from further consideration.

Once the location of impact and estimated force-time history corresponding to that location are identified, the force estimate is refined by applying assumptions related to an impulsive forcing function. The estimated force signal for the correct location may still have some noise and energy leakage due to noise on the signal, numerical error, and error from the force being applied at a point other than the discrete grid points considered. To compensate for these errors, the force signal is windowed around the impulse, and the energy of the windowed force signal is equalized to that of the un-windowed signal by applying a scale factor.

The experimental implementation of some embodiments of one method includes collecting frequency response information for each of a set of possible input locations, then uses that information to indirectly measure the forces during real time monitoring. In terms of the analytical development, $[H_k]$ for each input degree of freedom k is measured and inverted in advance of monitoring, and then to monitor the helicopter, acceleration data, [A], is measured when an impact is detected.

Modal impact testing is used to determine the frequency response function matrices. Three reference accelerometers 30 are mounted to the inside of the helicopter fuselage, and a modal grid is established on the exterior of the fuselage and sponsons. A modal grid with 6" spacing is chosen, giving approximately 1100 impact locations per side of the helicopter. The reference accelerometers chosen are tri-axial accelerometers, meaning that each gives three channels of acceleration data 50, which helps to minimize the error in the force estimate between channels of response data. Relating back to the analytical development, this setup has $N_{ch}=9$ possible acceleration channels, and $M=2316$ input degrees of freedom. FIG. 12.6 shows the Sikorsky CH-53A tested, and indicates the location of the three reference accelerometers.

Figure 1B:
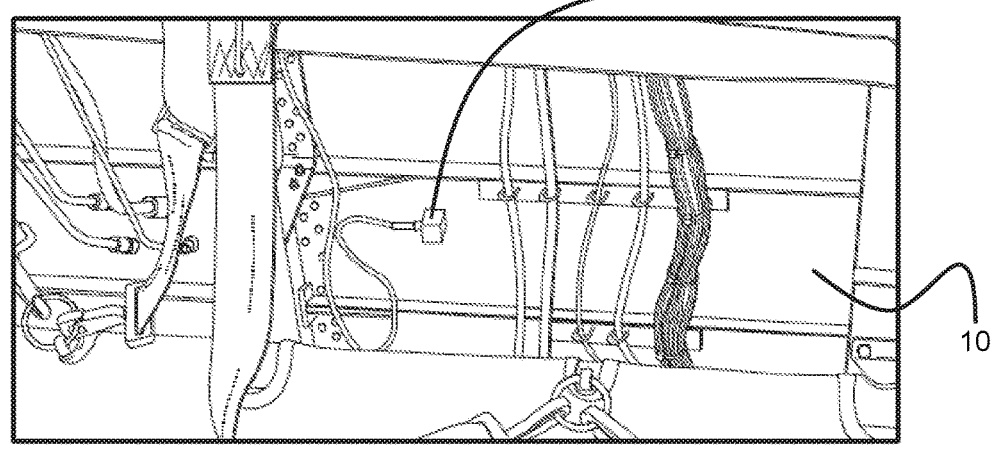
FIG. 1B shows an accelerator mounting detail on the middle of a structure.
Figure 1C:
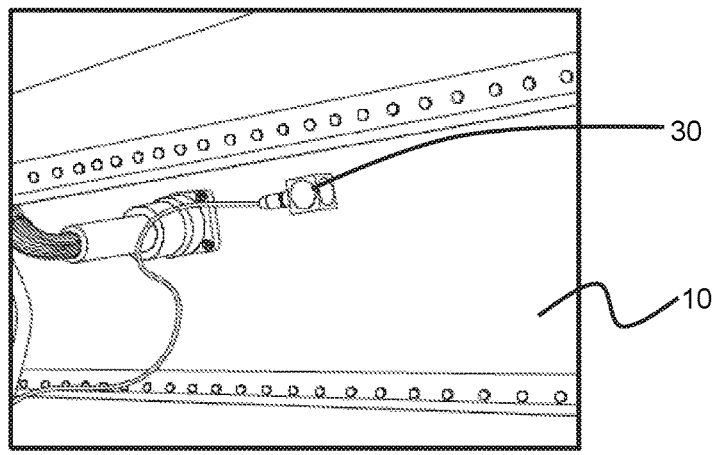
FIG. 1C shows an accelerator mounting detail on the front of a structure.

High sensitivity (1000 mV/g) accelerometers are chosen to maintain an adequately high signal to noise ratio from impacts that occur far away from the measurement points. The high sensitivity introduces an over-ranging situation when impacts are too close to the sensor, however. The large dynamic range in this situation results in using one sensitivity of accelerometer in some embodiments of the present invention, whereas other embodiments include the use of accelerometers having multiple sensitivities, One accelerometer is a PCB T356B18, a tri-axial 1V/g ICP piezoelectric accelerometer with a specified frequency range of 0.5-3000 Hz. The accelerometers are mounted with Loctite® 454 instant adhesive to the inside of the fuselage. The accelerometers mounted are shown in FIGS. 1A, 1B and 1C.

A modal impact test is carried out on the grid with a PCB 086C01 impact hammer used to measure and deliver three impacts at each grid point. A nylon tip is chosen for the majority of the impact points, but a rubber tip is also used at some points to avoid damaging windows or over-loading the accelerometers for impacts close to the accelerometer locations. The modal grid of the port side of the aircraft is shown overlaid on a drawing in FIG. 3B. The grid also covers the top of the sponsons and the starboard side of the aircraft.

Data 50 is acquired with an HP Agilent VXI chassis 20 with an E1432A data acquisition card sampling at 12.8 kS/sec for 1.28 seconds. The three sets of impact and response data per point are averaged with the $H_2$ FRF estimator, which minimizes error assuming that at least some of the noise occurs on the input measurement. The $H_2$ estimator is used rather than the more common $H_1$ because the former has been shown to be more effective for averaging data to be used for inversion and passive force estimation, although various embodiments anticipate using either of these estimators, or their equivalents. To evaluate the performance of the impact identification algorithm, validation input and response data is also acquired for each of the grid points.

With FRF's acquired for each impact point, the pseudo-inverse of the training FRF matrices can be calculated and used to monitor the helicopter immediately, or be saved to disk for future use. One aspect of inversion-based indirect force sensing is that most of the computation time is in calculating the pseudoinverses of training data FRF matrices, which can be before the health monitoring system goes online and the results saved to disk. When the monitoring system starts, inverse matrices are simply loaded into memory, making processing impact data relatively fast, approximately 0.5 seconds in one embodiment of the present invention.

The algorithm and acquired training data are implemented into a real-time monitoring system 20. Data acquisition is done with a National Instruments compact-DAQ chassis with three NI-9233 cards acquiring data from accelerometers at 10 kSa/s. The small form factor of the data acquisition further shows aspects of this minimal sensing approach; other methods would use a substantial data acquisition system to acquire a large number of channels at sample rates of 100 kSa/s, but as FIGS. 2A and 2B show, this data acquisition has minimal space, power and cooling requirements.

Figure 3A:
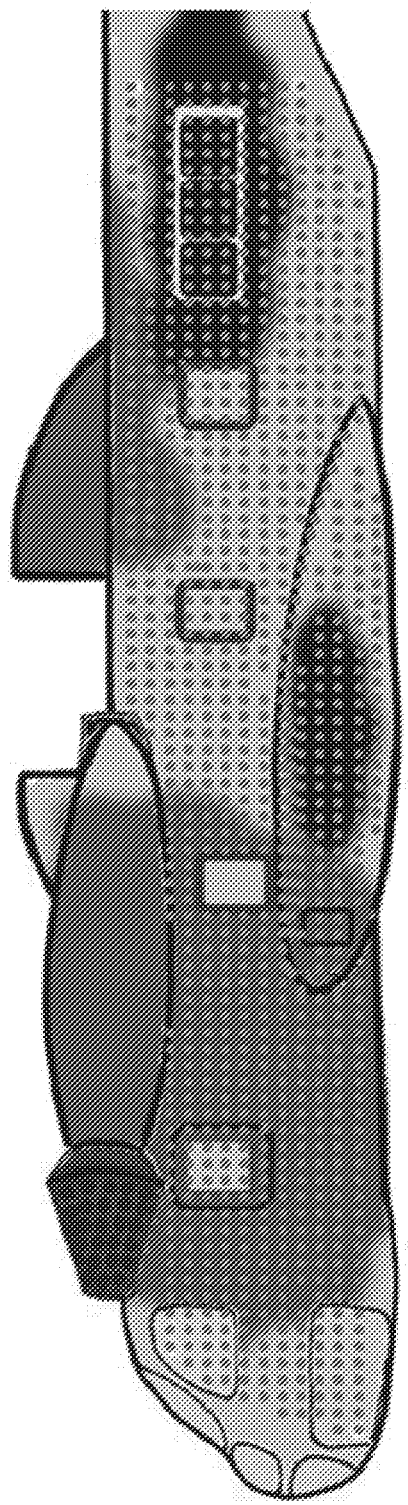
FIG. 3A: Drawing of helicopter (port side) with modal impact locations indicated.
Figure 3B:
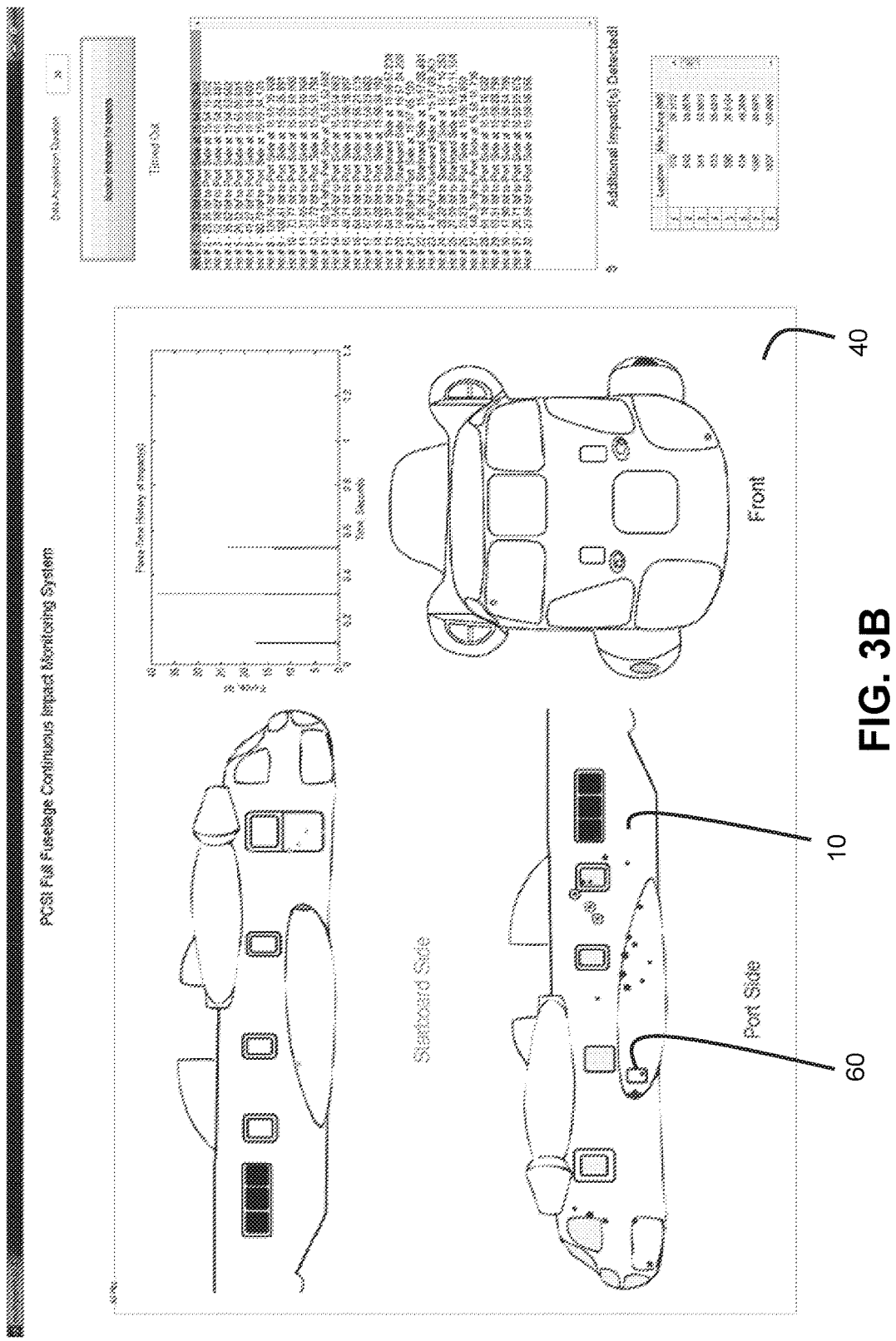
FIG. 3B: Helicopter impact monitoring system GUI showing results of impact to starboard sponson.

A graphical user interface (GUI) 40 is developed to allow for intuitive user interaction and the ability to quickly and qualitatively test the performance of the system to various impacts. A range of projectiles can be thrown at the helicopter, and various other loading situations, such as a mechanic jumping down onto the sponson can be quickly tested. In addition, the aircraft can be hit with an instrumented impact hammer, and the recreated force can be directly compared with the actual measured force. FIG. 3B shows the GUI displaying the results of an impact 60 to the port side electronics door.

Figure 4A:
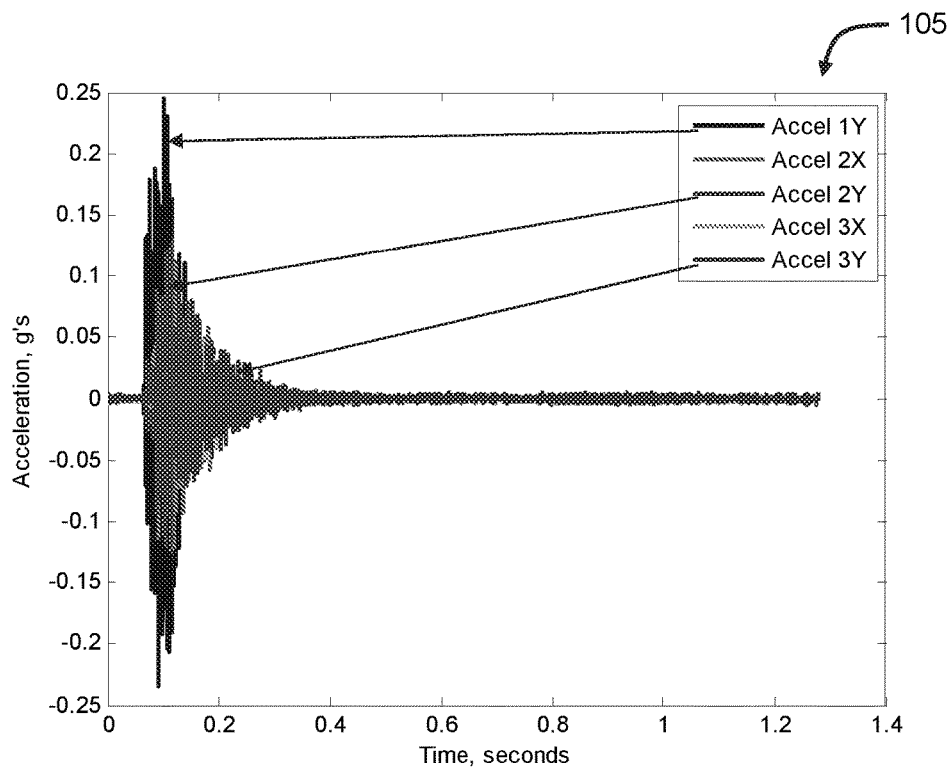
FIG. 4A shows measured acceleration data 105 in the time domain.
Figure 4B:
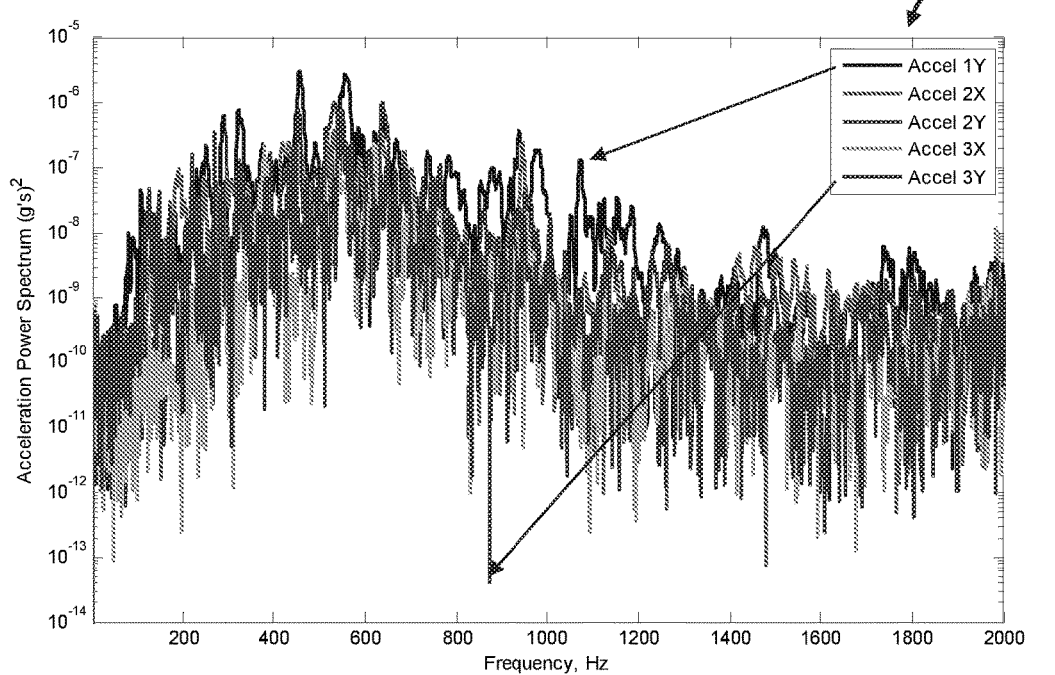
FIG. 4B shows measured acceleration data 106 in the frequency domain.
Figures 5A, 5B, 5C, 5D:
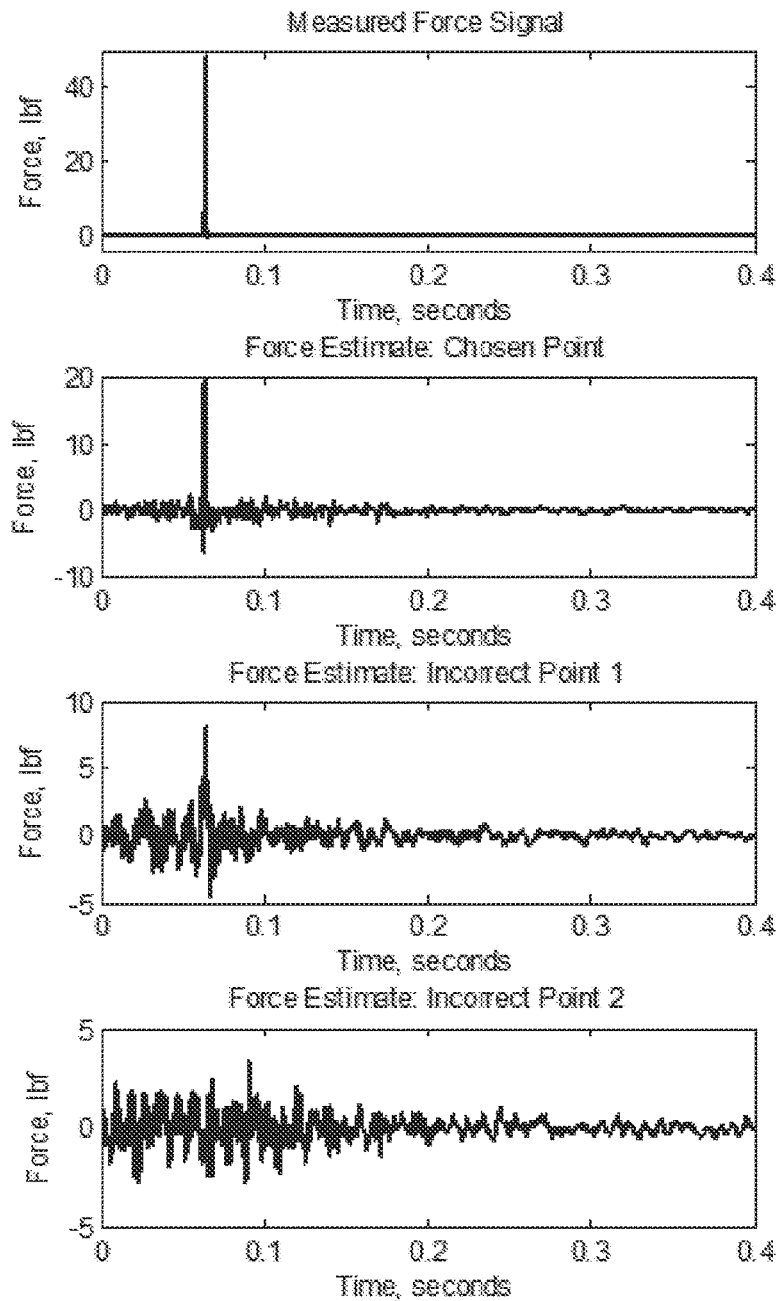
FIG. 5A: Examples of recreated force signals for chosen input location and two incorrect points according to another embodiment of the present invention.
FIG. 5B: Examples of recreated force signals for chosen input location and two incorrect points according to another embodiment of the present invention.
FIG. 5C: Examples of recreated force signals for chosen input location and two incorrect points according to another embodiment of the present invention.
FIG. 5D: Examples of recreated force signals for chosen input location and two incorrect points according to another embodiment of the present invention.
Figures 5E, 5F, 5G, 5H:
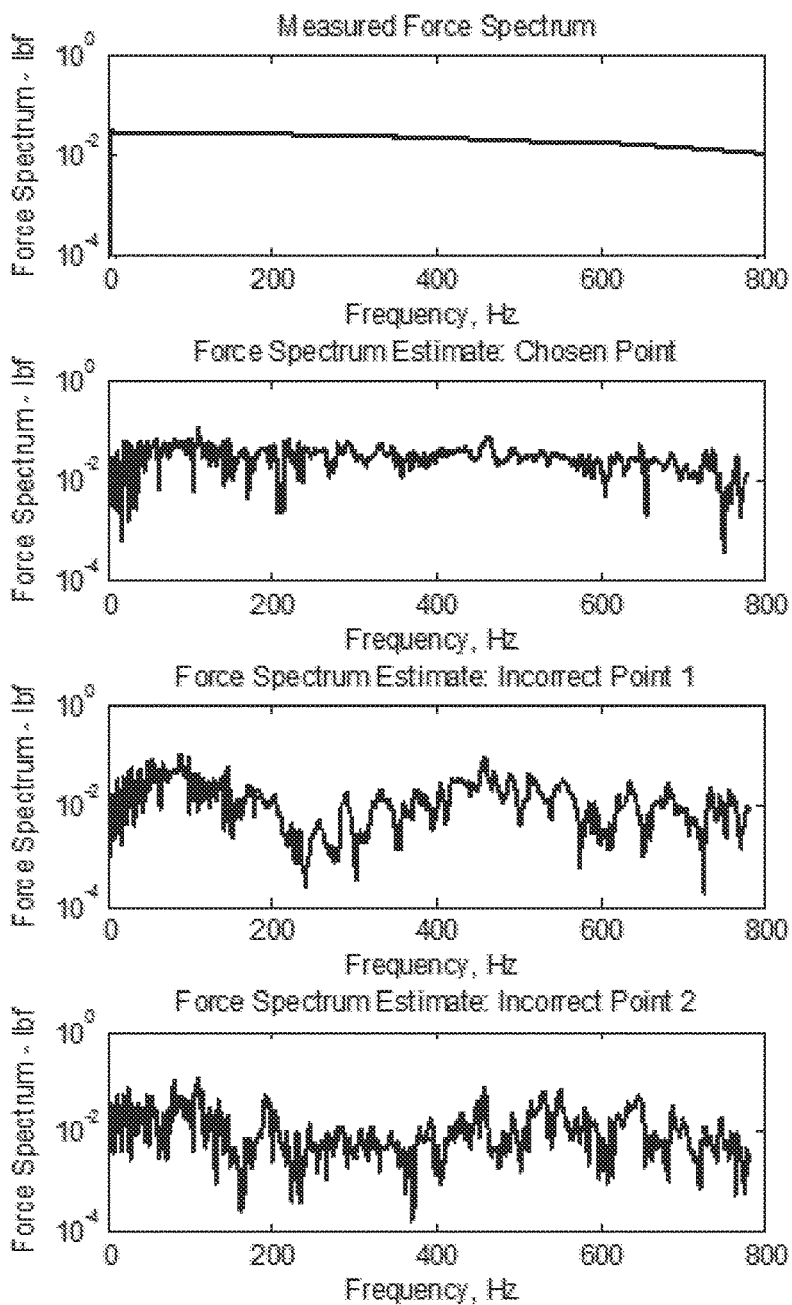
FIG. 5E: Examples of recreated force signals for chosen input location and two incorrect points according to another embodiment of the present invention.
FIG. 5F: Examples of recreated force signals for chosen input location and two incorrect points according to another embodiment of the present invention.
FIG. 5G: Examples of recreated force signals for chosen input location and two incorrect points according to another embodiment of the present invention.
FIG. 5H: Examples of recreated force signals for chosen input location and two incorrect points according to another embodiment of the present invention.

In order to show the process of the algorithm in detail, the results of the algorithm step-by-step for a representative validation data point will be shown. The impact considered is in the upper middle section of the starboard side of the fuselage. The response data from the accelerometers are measured, and shown in FIGS. 4A and 4B.

With data collected, force estimates are generated for each possible impact location. To show the difference in force estimates between the correct location and other locations, FIGS. 5A, 5B, 5C, 5D, 5E, 5F, 5G and 5H show three representative recreated force estimates are shown in both the time and frequency domain, along with the measured force input for comparison. This figure shows that the correct input location best matches the actual input to the system, but the force domain estimation does not match the actual force spectrum well. Once the correct location is selected, the force estimate is refined and matches the actual signal better than the initial estimation.

Figure 6:
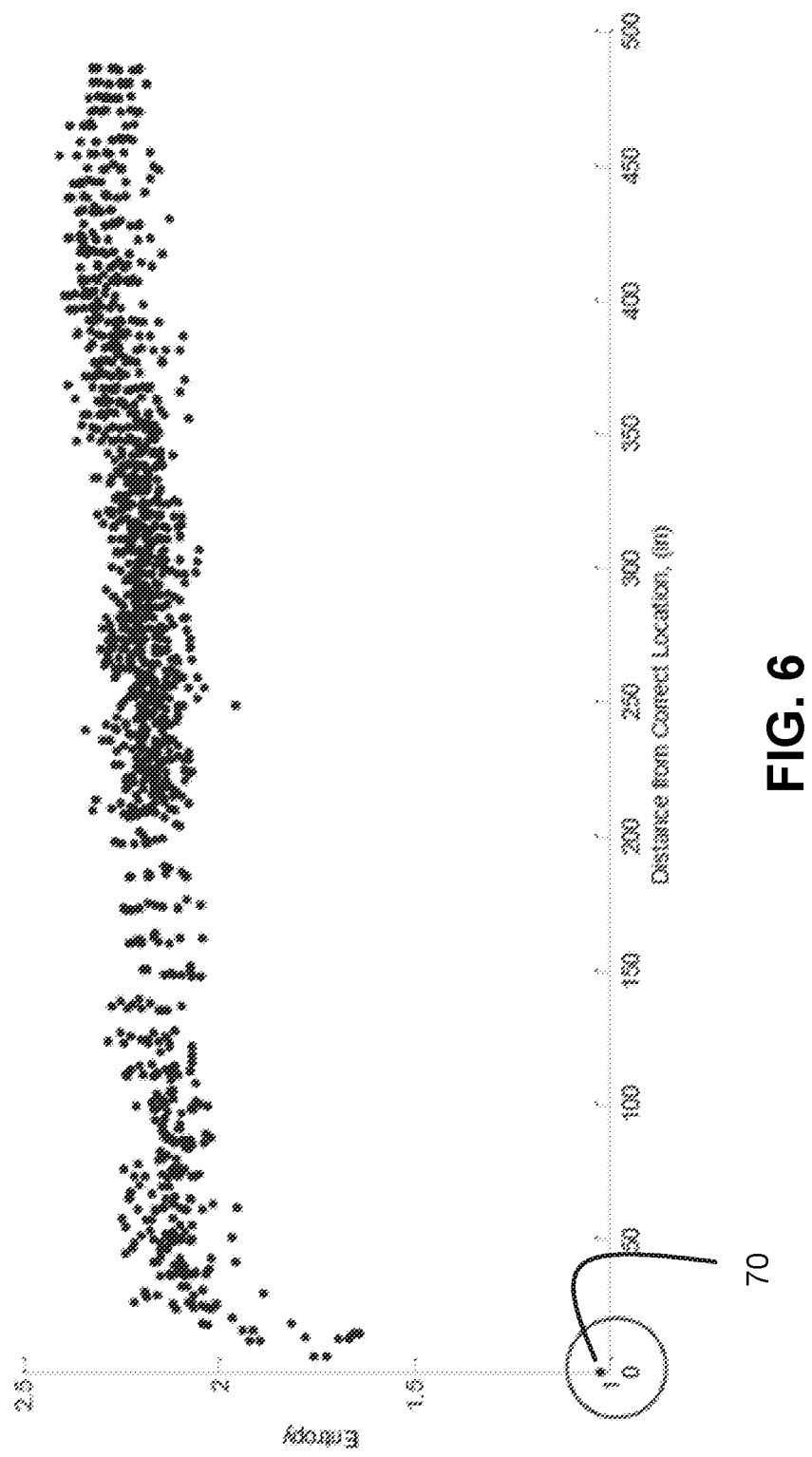
FIG. 6: Calculated entropy value vs. distance from actual impact location according to another embodiment of the present invention.

The signal entropy or randomness is calculated for each of the force estimates between 0 and 0.5 seconds. FIG. 6 is a plot of the calculated entropy value against distance from the correct location shows the ability to discriminate between grid input points with this calculation. For this example grid point, the second lowest entropy value is 60% larger than the entropy value 70 for the actual location.

Figures 7A, 7B:
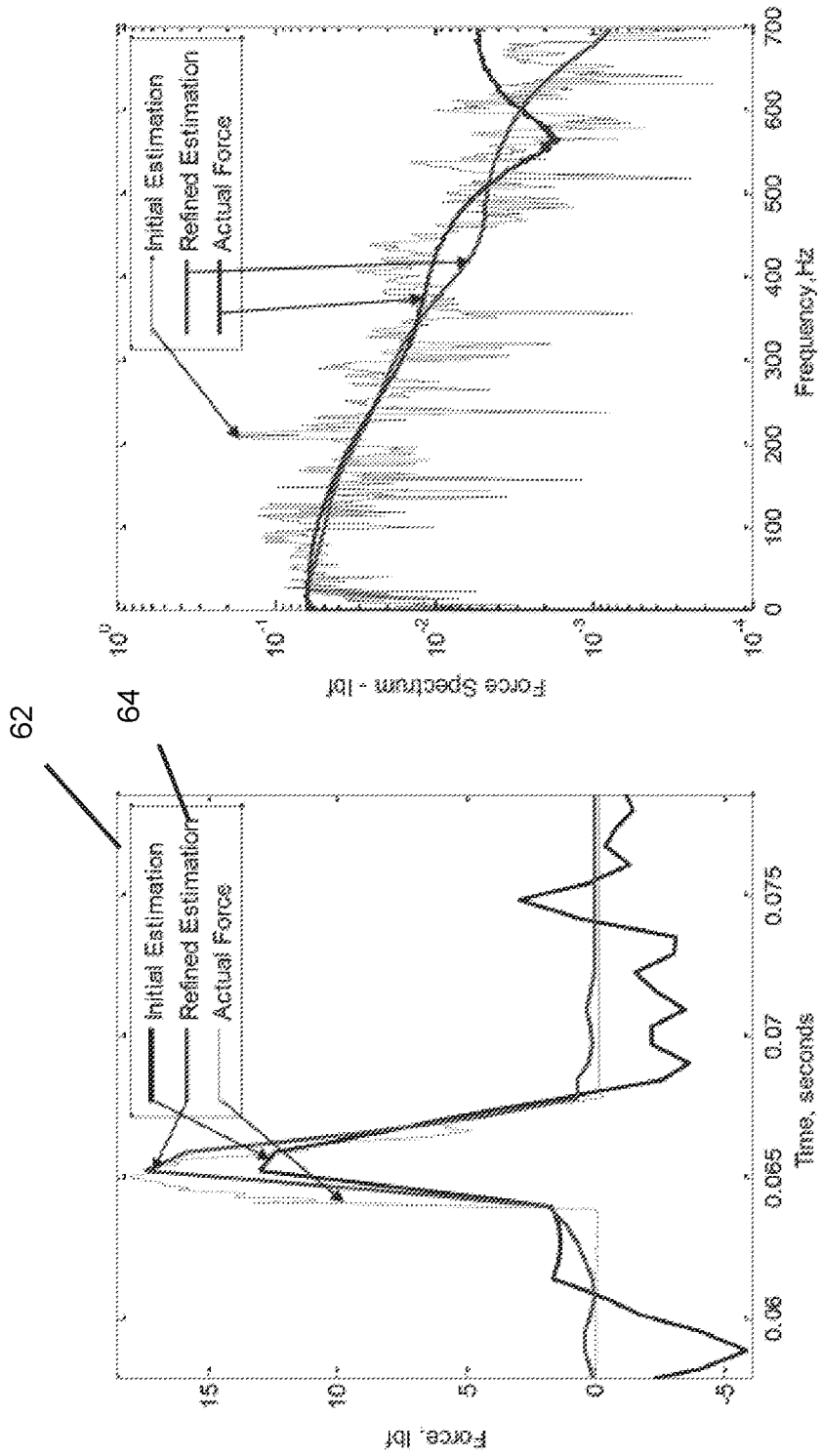
FIG. 7A: Force windowing results in the time domain for impact to sponson according to another embodiment of the present invention.
FIG. 7B: Force windowing results in the frequency domain for impact to sponson corresponding to FIG. 7A.

With the location of impact identified, the force estimation is refined by applying a window around the main pulse, then equalizing the signal power between the windowed signal and the original estimation. This method has the effect of making the force spectrum estimate follow the actual profile of the impact's force spectrum, and better estimate the peak force. The windowing process is shown in FIGS. 7A and 7B for an impact to the starboard sponson showing estimations 62 and 64 (initial and refined, respectively) of an impact load.

A validation simulation was carried out with two impacts per grid point to the starboard side of the helicopter and three impacts per point to the port side of the helicopter. Results show that 93% of impacts to the port side of the helicopter are located to the nearest point, and 98.5% of impacts are located within 6 inches. The starboard simulation showed that 90.0% of impacts on the starboard side are located at the correct grid point, and 99.0% of the validation points are located within 18 inches of the correct location. The results of this validation simulation are summarized in Table 1.

TABLE 1

Results of Validation Simulation

| Distance Error (inches) | 0 | 6 | 9 | 12 | 15 | 18 |
|---|---|---|---|---|---|---|
| Port Percent Located Within | 92.7% | 96.3% | 97.4% | 97.9% | 98.0 | 98.5% |

TABLE 1-continued

Results of Validation Simulation

| Distance Error (inches) | 0 | 6 | 9 | 12 | 15 | 18 |
|---|---|---|---|---|---|---|
| Starboard Percent Located Within | 90.0% | 95.8% | 97.3% | 98.3% | 98.9% | 99.0% |

Figure 8:
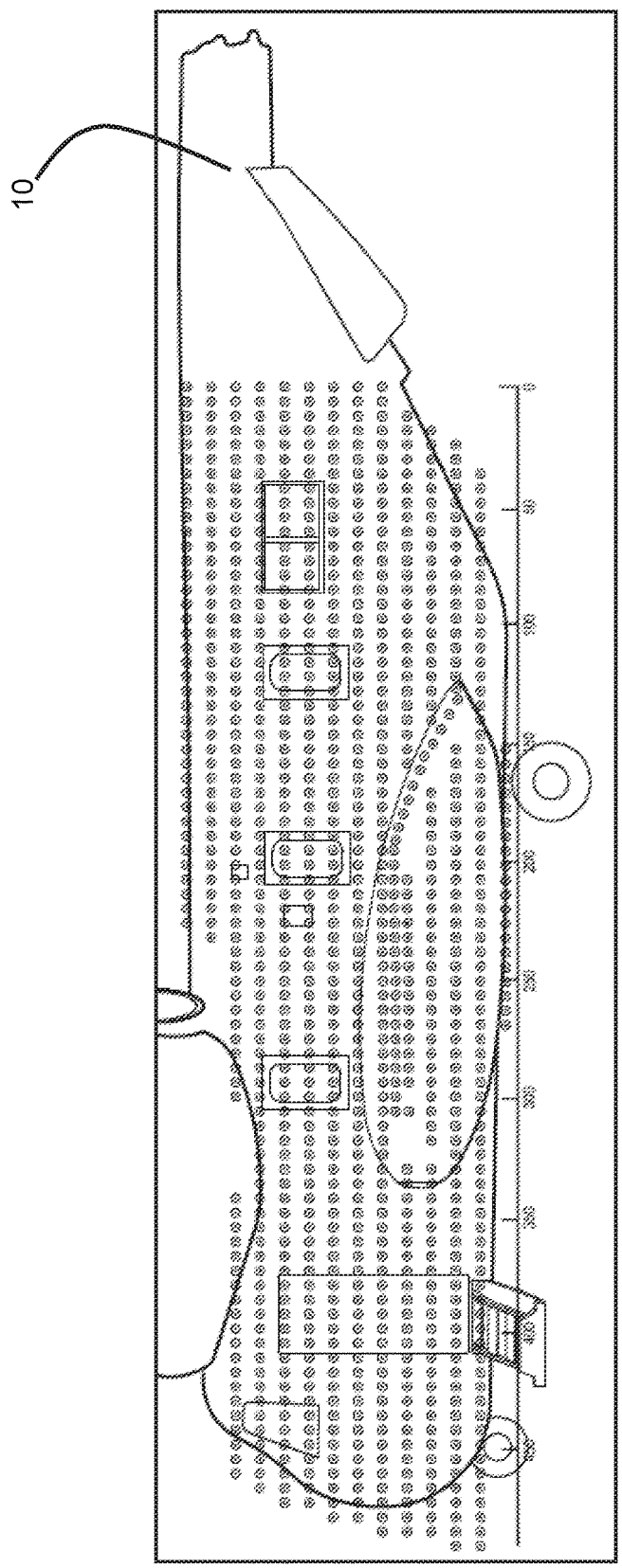
FIG. 8: Error indicated on grid-dot size is proportional to position error.

Another result from the validation simulations is that the error in location accuracy is not found to increase with distance from the sensor. In fact, the worst errors in location accuracy are found to be when impacts are close to the sensors where clipping distorts the response measurement. FIG. 8 shows the position identification error on the grid, with dot size proportional to the position identification error. The worst area is at the top of the aircraft's tail section, where the rearmost accelerometer is mounted, and another problem area is found towards the front of the aircraft near the engine nacelle, where the front sensor is mounted. The independence of error and distance from the sensors is one aspect of implementing large scale impact identification systems.

Figure 9:
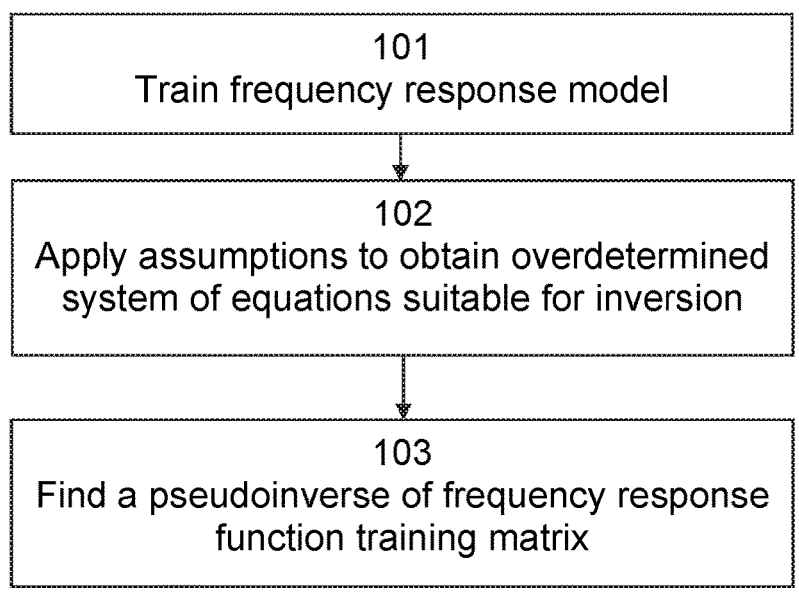
FIG. 9 is a block diagram of a method according to another embodiment of the present invention.

In one embodiment of the present invention (also as shown in FIG. 9), there is one method for preparing a dataset that includes the following: Train the frequency response model 101 using modal impact hammer and reference accelerometer(s) (multiple accelerometers or multiple directions in one accelerometer (tri-axial), such that more than one channel of response is measured), with modal impact hammer applying impulsive load to each point on a grid established on the test specimen. Yet another embodiment includes interpolating frequency response functions spatially to increase resolution for load identification. Apply assumptions 102 to obtain overdetermined system of equations suitable for inversion. Limiting the frequency bandwidth to the range well excited in (101). Assuming that the force was applied at one point. Find a pseudoinverse of the frequency response function training matrix 103 that will determine an adequate solution to the force applied at each point given a set of measured responses from channels of reference accelerometers.

Figure 10:
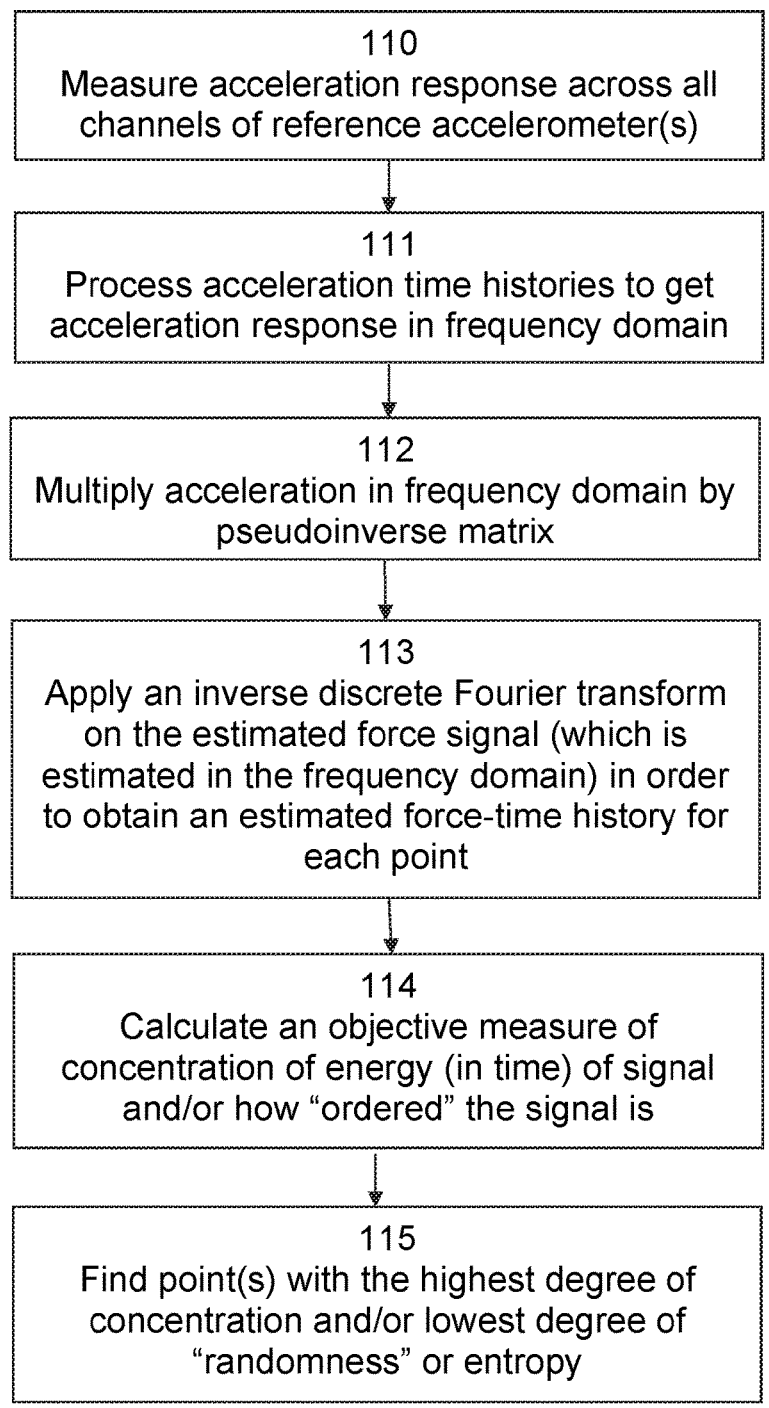
FIG. 10 is a block diagram of a method according to another embodiment of the present invention.
Figure 11:
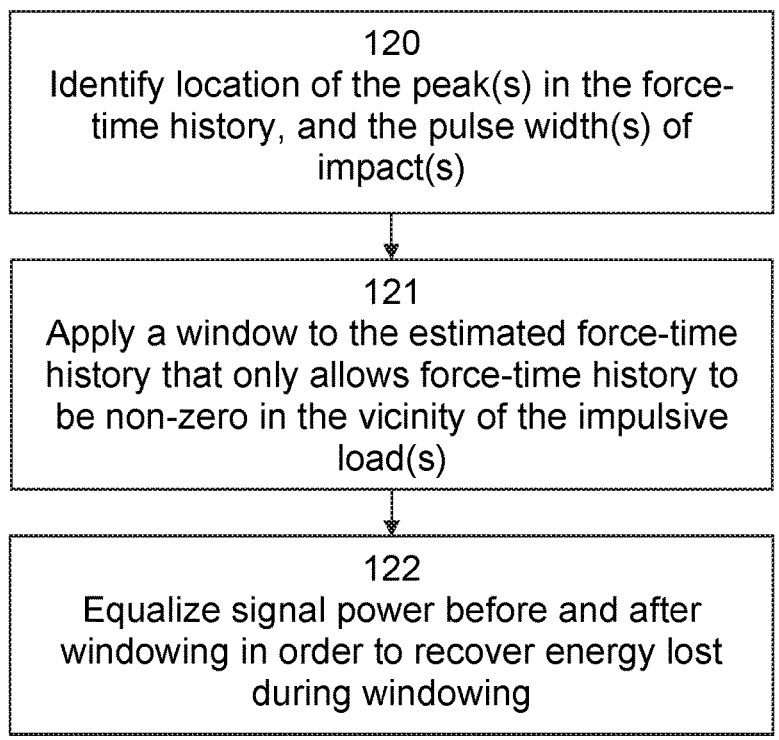
FIG. 11 is a block diagram of a method according to another embodiment of the present invention.

Yet other embodiments of the present invention include an algorithm for real time monitoring of a structural system (also as shown in FIG. 10) that includes the following: When the acceleration signal satisfies triggering criteria, measure acceleration responses 110 across many channels of reference accelerometer(s). Apply a discrete Fourier transform to acceleration time histories 111 to get acceleration response in frequency domain. For each spatial point (physical point on modal grid or interpolated point), multiply acceleration in the frequency domain 112 by pseudoinverse matrix found in (3) to find estimated force as if it was applied at that point. Apply an inverse discrete Fourier transform 113 on the estimated force signal (which is estimated in the frequency domain) in order to obtain an estimated force-time history for each point. With the force-time histories in 113, calculate an objective measure of concentration of energy (in time) of signal and/or how "ordered" the signal is 114 ("ordered" being the opposite of random). For example, calculate signal entropy of a portion (or all of) the force time histories. Find point(s) with the highest degree of concentration and/or lowest degree of "randomness" 115 and identify the location corresponding to the point(s) as most likely to be the location of impact. (plural is specified because there may the case where several points are difficult to distinguish between, in which case all or many of these points can be identified as possible locations of impact) Some embodiments of the present invention include an algorithm (as also shown in FIG. 11) for estimating the location and impact of an impulsive load on a structure.

In order to find a better estimate of the unknown force, apply the following signal processing techniques to the force-time history(ies) corresponding to the most likely point(s) of impact: identify location of the peak(s) 120 in the force-time history, and the pulse width(s) of impact(s), based upon 9(a), apply a window 121 to the estimated force-time history that allows force-time history to be non-zero in the vicinity of the impulsive load(s); and equalize signal power before and after windowing 122 in order to recover energy lost during windowing.

Impact identification according to some embodiments of the present invention was implemented on two test specimens in this work in order to evaluate both a small, relatively uniform structure and a large, non-homogeneous structure. The small structure tested was a carbon-fiber filament wound missile rocket motor casing 10, and the large structure was the fuselage 10 from a heavy-lift helicopter. In addition, testing of a small plate was used to form the basis of a theoretical model that was later used for simulation.

The first test specimen considered was a carbon-fiber filament wound rocket motor casing, which is designed to house propellant for a helicopter-launched missile. Composite pressure vessels such as this one have a significant weight advantage over metallic components of similar strength, but can suffer material damage due to impacts without offering any clear visual indication. With a knowledge of the location and magnitudes of impacts sustained to these canisters, detailed inspections and maintenance could be performed to identify and repair impact damage. In addition to the potential advantages of impact identification in this application, the canisters provided a good example of a relatively small structure with uniform construction, which could be used as a starting point to evaluate impact identification algorithms before testing their effectiveness on a large, complex structure such as the helicopter fuselage 10 that was also considered.

FIG. 12.1 shows one of the canisters that was tested. Each canister measured 24 inches long, had a 7 inch outside diameter throughout most of the length, and tapered out at the open end. A grid of 64 impact locations was drawn on the test canister, with grid points spaced approximately 4 inches apart. Every impact identification method that was considered required a set of potential impact locations to be chosen in advance and frequency response functions between impacts at each location and the response measurements to be estimated, so modal testing was first used to train the model. The canister was suspending using a bungee cord during testing to simulate a free-free boundary condition.

Acceleration response measurements were provided by a PCB 356A13 tri-axial accelerometer, with a nominal sensitivity of 5 mV/g, which was attached to the canister with Loctite 454 instant adhesive. In addition, another tri-axial accelerometer was created by fastening three PCB U350B02 single axis shock accelerometers with nominal sensitivities of 0.1 mV/g to an aluminum cube, which was strapped to the canister by means of a large hose clamp. The accelerometers used are shown at the time of testing in FIG. 12.2.

To create the frequency response function model that was used in impact identification, modal impact testing was performed using a PCB 086C01 modal impact hammer, as illustrated in FIG. 12.3. A brass impact tip was used with the modal impact hammer in order to excite a broad range of frequencies.

Data acquisition settings were chosen in order to provide good training data for estimating frequency response functions, and, in some instances, provide more information than necessary, in order to determine the effect of having more or less information about the signal. The sampling frequency, for instance, was chosen to be much higher than twice the highest frequency of interest so that the effects of lower sampling frequencies could be investigated using post-processing. To ensure that leakage error did not significantly affect frequency response function estimates, the data acquisition duration was chosen such that the response signal was completely observed, that is, such that the response amplitude had decayed to the noise floor by the end of the acquisition duration. A pre-trigger of consistent length was used to ensure that the beginning of the response signal was captured and the data could be synchronously averaged. Auto- and cross-power spectra were averaged between sets of input and response measurements from five impacts per point, and the frequency response functions were estimated using the H1 FRF estimate in order to minimize the effect of output noise on the FRF estimate. A summary of relevant data acquisition and testing parameters is included in Table 2.1.

TABLE 2.1

Testing parameters for the rocket motor casing are summarized here.

| | |
|---|---|
| Sampling Frequency | 25.6 kSa/sec |
| Time Duration | 1.28 sec |
| Response Window | Rectangular |
| Pre-Trigger | 5% |
| Number of Impacts Averaged per Point | 5 |
| Data Acquisition Equipment | Agilent E1432A in VXI Chassis |

In order to test the performance of impact identification algorithms, both a set of training data and validation data were collected. The training data was used to estimate the frequency response functions for the underlying impact identification model, then the response from the validation impacts was passed through the impact identification algorithm, and the estimated forces and locations were compared to known values to quantify performance. While five impacts per point were used for training data, the validation data included only two impacts per point, because the validation data was not used for averaging.

Frequency response function estimates for the canister showed mostly lightly damped resonances, and good signal to noise ratio's on measurement, which lead to relatively good coherence relative to measurements on the helicopter fuselage. FIGS. 12.4A and 12.4B show representative frequency response functions between an impact point on the canister and a tri-axial accelerometer mounted on the canister. Another feature of impacts to this test specimen was that impacts excited a fairly consistent frequency bandwidth. In FIG. 12.5, the average force auto power spectra for each impact point is shown. Impacts to the tapered bottom section of the canister tended to excite a slightly wider frequency range, but all impacts to the canisters consistently excited up to at least 1500 Hz.

The second structure tested was the fuselage of a retired heavy-lift helicopter. This structure was the focus of the work, because while impact identification algorithms have been proven on small structures, none had been implemented on a structure of this magnitude. This aircraft differs from an operational helicopter of this type in several ways, but the airframe is largely the same as it would be while this helicopter was in service. The key differences are that the swash plate, rotors, tail section and some windows have been removed, and the airframe has been modified to incorporate three carbon-fiber reinforced composite sandwich panels on each side towards the tail of the fuselage. This addition of composite panels 85 allows for testing panels more representative of what future aircraft will feature, along with the aluminum fuselage skin that is used on most existing aircraft in service.

Both sides of the fuselage and both sponsons of the helicopter were tested. Although both sides of the fuselage were considered, sensors were only attached to the port side of the aircraft. Three high sensitivity tri-axial accelerometers were mounted to the aircraft in the positions shown in FIG. 12.6. The accelerometers used were PCB 356B18 accelerometers, with nominal sensitivities of 1000 mV/g, and a frequency range±10% of 0.5-5000 Hz. The accelerometers were attached to the fuselage using Loctite 454 instant adhesive and shown in FIGS. 1A, 1B and 1C.

The modal grid spanned the majority of the length of the fuselage, with a grid spacing of 6 inches. This grid spacing resulted in 1122 impact points on the port side of the fuselage, and 1194 impact points on the starboard side of the fuselage. The port side grid is superimposed on an illustration of the aircraft in FIG. 12.7. Each point was impacted with a PCB 086C01 modal impact hammer, with a nylon tip for most impact points. For testing of the windows and a few other especially compliant or fragile areas of the aircraft, the nylon impact tip was replaced with a rubber impact tip. A summary of data acquisition settings used for the training data is shown in Table 2.2.

TABLE 2.2

Data acquisition settings for the fuselage modal impact testing is summarized here.

| | |
|---|---|
| Sampling Frequency | 12.8 kSa/sec |
| Time Duration | 1.28 sec |
| Response Window | Rectangular |
| Pre-Trigger | 5% |
| Number of Impacts Averaged per Point | 3 |
| Data Acquisition Equipment | Agilent E1432A in VXI Chassis |

One difference between the fuselage and test specimens that had been used previously is that this aircraft was constructed with a wide variety of materials, and complex joints were present throughout the structure, making developing a sufficiently accurate first-principles based models of the structure impractical. Some examples of the materials used on the structure included the retrofitted carbon fiber sandwich panels, fiberglass sections, aluminum skin reinforced with riveted stiffening ridges, and plastic windows, as shown in FIGS. 12.8A, 12.8B, 12.8C and 12.8D. One of the effects of the non-homogeneous construction of this structure is that impacts to different locations excite a widely varying bandwidth. When an object impacts a compliant area of the structure, only a narrow bandwidth is excited, but the force is more broadband when a stiff portion of the structure is impacted by the same type of object. The average force auto-power spectra are plotted for several example points on the structure in FIG. 12.9, showing that while some impacts excited a bandwidth of over 1500 Hz, many did not excite more than a 400 Hz bandwidth before the magnitude of the force spectrum dropped more than an order of magnitude.

The characteristics of this large, complex structure presented additional challenges for applying impact identification. The frequency response function estimates, compared to those for the rocket motor casing, were relatively heavily damped and modally dense, with considerably worse coherence values for most impact locations on the aircraft. A typical frequency response function estimate with coherence values is shown in FIGS. 12.10A and 12.10B. Low coherence values for the frequency response function estimates complicate the impact identification process.

The main cause of low coherence values for measurements on the helicopter as compared to the missile canister was hypothesized to be the large dynamic range of response measurements at different sensor locations. While an impact may have excited one or two of the accelerometers well, often at least one sensor observed a low amplitude vibration signal, leading to a low signal-to-noise ratio, which manifested itself in low coherence values. The low coherence values above 400 Hz for the example in FIGS. 12.10A and 12.10B were likely due to the narrow force excitation bandwidth. For this measurement, the force excitation had fallen more than an order of magnitude by 400 Hz, which would result in low amplitude response and low signal-to-noise ratio across all channels in the frequency range above 400 Hz.

Another variation that would occur between the aircraft when the training data was taken and during operation is the static and quasi-static loading condition of the airframe. In addition, the boundary condition of the portions of the aircraft in contact with the fuel tank would change between when the fuel tank was at different fill levels. To examine the effect of both of these variations, the fuel tanks, which were housed in the sponsons of the helicopter, as shown in FIG. 12.11, were filled with water. Initial testing was done with the fuel tanks empty, so the tests with the fuel tanks full could be used to show the effects of an additional load and boundary condition change at once. The capacity of the fuel tanks was 638 US Gallons, so assuming a temperature of 72° F., the additional water added a static load of approximately 5300 lbf. After the fuel tanks were filled, both the starboard and port side of the helicopter were tested with three impacts per grid point, using the same settings as used for collecting the baseline training data.

In order to generate a representative analytical model of a thin plate for simulations, modal impact testing was carried out on a roughly square aluminum plate, and modal parameters of the structure were estimated and used to create the model. While modal properties representative of an aluminum plate could be generated through closed form solutions, an experimental method for estimating these properties was done in this work to show an example of how models for use in simulating impact identification could be built for more complex materials, were closed form solutions are not available.

The plate was instrumented with three single-axis accelerometers mounted on the underside of the plate, which was supported by foam blocks at each corner. FIG. 12.12 shows the experimental setup with the modal impact grid. The grid consists of 49 impact points, which were impacted with a PCB 086C01 modal impact hammer with a nylon impact tip. Force and response data was acquired for five impacts per grid point, with a sampling duration of 1.28 seconds and a sampling frequency of 25.6 kSa/sec. Frequency response functions were estimated using the H1 estimator.

A process for identifying the location of magnitude of impact loads acting on a non-homogeneous structure according to one embodiment of the present invention is illustrated in FIG. 13.1. First, modal impact testing 201 is used to characterize the forced response of the discretized underlying model of the structure. Several sets of impact force and acceleration response data are averaged for each possible impact point to estimate the frequency response function 202 between that impact location and the response measurement locations/directions. After estimating the frequency response functions, a set of assumptions along with the FRF model, which is constructed from the training data, are used to solve an overdetermined inverse problem 203. The pseudoinverse to solve the systems of equations of interest is calculated in advance of monitoring for impacts, and the results are saved into memory.

When an impact is detected 210, the impact response measurements are pre-processed 211 and the response spectra due to a single impact 212 are passed to the force spectrum estimation algorithm 213. By combining the measured responses and the pseudoinverse formed using the FRF model based on the training data, the impact force is estimated 214 assuming that it acted at each of the possible input measurement degrees of freedom. Having calculated these force estimates, the algorithm then determines which force estimate most likely corresponds to the actual impact location 215. The estimated force for the selected location is then further post-processed to refine the force estimate. A method according to one embodiment of the present invention predicts one or more impact locations 220, as well as providing an estimate 230 of the magnitude.

In order to explain the technical details of the indirect force identification methods, a simple example of a cantilevered beam is used for illustration, as depicted in FIG. 13.2. This beam is a continuous structure, which can be excited by a forcing function that varies with both time and position along the beam. The response of the structure changes with position along the beam. Because there are infinitely many degrees of freedom, there are infinitely many modes of vibration.

The model used in some embodiments of the present invention is a data-driven model determined generally from measurements, rather than a first-principles model of the physics of the structure. However, the present invention also contemplates those embodiments in which a data driven model is augmented with an analytical model, and further those embodiments that generally use analytical models of the structure. The data-driven model of the structure is in a form with which the response (or forcing function) can be estimated based on measurements. The continuous representation of the structure should be discretized both temporally and spatially in order to create this data-driven model, as illustrated in FIG. 13.3. Spatially, the model should be reduced to a finite number of measurement degrees of freedom. In the case of the present example, six degrees of freedom are used at which a force acts and the system responds at each time point. The time histories are discretized temporally by replacing the continuous time variable t with $t_n$, where $t_n = nD_t, n=0,1,\ldots,N$ and $Dt=1/f_s$, where $f_s$ is the sampling frequency.

This discrete form of the model should now also be limited in terms of the number of measurements available. The measurement degrees of freedom are defined by the number of output sensor channels that are available and the number of grid points that are impacted when modal impact testing is conducted to gather the training data. The number of output measurement degrees of freedom will be represented by $N_o$, and the number of input measurement degrees of freedom will be called $N_i$.

The example beam structure in the final configuration that is representative of an impact identification configuration is shown in FIG. 13.4. Some differences between the discretized model that will be used in the impact identification technique and the original discretized model are that (a) the beam structure is limited to $N_o=2$ output measurement degrees of freedom, and (b) the acceleration response is measured in the beam, as it will be in the actual test setup using accelerometers, rather than the displacement response. Although the output measurement degrees of freedom are a subset of the input degrees of freedom in this case, that is not generally the case when tri-axial accelerometers are used to record the response. When tri-axial accelerometers are used, the forced degrees of freedom can be limited to the normal direction whereas some response degrees of freedom will be measured in directions perpendicular to the normal direction. Although what is shown and described herein refers to measurement of acceleration, it is appreciated that various embodiments of the present invention are not so constrained, and contemplate the measurement of any spatial parameter, including acceleration, velocity, or displacement, and including both linear and rotational forms thereof.

Although what has been shown and described is the preparation of a model that is predictive of displacement, it is further appreciated that the models could also be in terms of velocity or acceleration. Further, it is appreciated that both the measured response and the predicted responses can be one-dimensional (uniaxial), two-dimensional (biaxial), or three-dimensional (triaxial). In a preferred embodiment, the measurements are taken using triaxial accelerometers, but other embodiments are not so constrained.

Various embodiments of the present invention pertain to the use of a structural model, either analytical, empirical, or a combination of both, in which the number of predicted responses is substantially greater than the number of measurements. In so doing, it is possible in some embodiments to devise an algorithm in which a small number of sensors can be used to predict responses over a large, non-homogeneous object. In certain embodiments, the degrees of freedom of the measured responses is less than about one-tenth of the degrees of freedom of the predicted responses (these predicted responses being the hypothetical calculated force inputs). In yet other embodiments, the number of measurement DOF is about one-twentieth of the response DOF. In still further embodiments, the ratio exceeds one to one hundred.

A set of assumptions should be applied to formulate an overdetermined inverse problem that is suitable for inversion with a pseudoinverse to solve for an estimate of the forcing function. With no assumptions or constraints applied, the inverse problem is underdetermined. This example presents the approach assuming $N_o$ acceleration response measurements are available. The frequency band is limited to $\{0, f_{max}\}$ and the number of frequency points is reduced to $N_f$, yielding a frequency resolution of $D_f$. $N_i$ discrete points are defined where a force can be applied. This underdetermined system can be reduced to $N_f$ systems of equations as follows:

$$\begin{Bmatrix} A_1(n\Delta_f) \\ A_2(n\Delta_f) \\ \vdots \\ A_{N_o}(n\Delta_f) \end{Bmatrix} = \qquad (3.1)$$

$$\begin{bmatrix} H_{11}(n\Delta_f) & H_{12}(n\Delta_f) & \ldots & H_{1N_i}(n\Delta_f) \\ H_{21}(n\Delta_f) & H_{22}(n\Delta_f) & \ldots & H_{2MN_i}(n\Delta_f) \\ \vdots & \vdots & \vdots & \vdots \\ H_{N_o1}(n\Delta_f) & H_{N_o2}(\Delta_f) & \ldots & H_{N_oN_i}(n\Delta_f) \end{bmatrix} \begin{Bmatrix} F_1(n\Delta_f) \\ F_2(n\Delta_f) \\ \vdots \\ F_{N_i}(n\Delta_f) \end{Bmatrix},$$

Equation (3.1) represents a set of $N_f$ system of equations, which are underdetermined for $N_i > N_o$, that is, when there are more input degrees of freedom than there are output degrees of freedom. An estimate of the one force of interest can be found in some embodiments (but not other embodiments) by assuming there is only one force input point. This assumption that a forcing function acts at a single point allows for a set of overdetermined system of equations to be formulated, provided that more than one acceleration response signal is available. If it is known (or assumed) that a force acts at degree of freedom k, the system of equations in (3.1) becomes:

$$\begin{bmatrix} A_1(0) & A_1(\Delta_f) & A_1(2\Delta_f) & \ldots & A_1(N_f\Delta_f) \\ A_2(0) & A_2(\Delta_f) & A_2(2\Delta_f) & \ldots & A_2(N_f\Delta_f) \\ \vdots & \vdots & \vdots & \ddots & \vdots \\ A_{N_o}(0) & A_{N_o}(\Delta_f) & A_{N_o}(2\Delta_f) & \ldots & A_{N_o}(N_f\Delta_f) \end{bmatrix} = \qquad (3.2)$$

$$\begin{bmatrix} H_{1k}(0) & H_{1k}(\Delta_f) & H_{1k}(2\Delta_f) & \ldots & H_{1k}(N_f\Delta_f) \\ H_{2k}(0) & H_{2k}(\Delta_f) & H_{2k}(2\Delta_f) & \ldots & H_{2k}(N_f\Delta_f) \\ \vdots & \vdots & \vdots & \ddots & \vdots \\ H_{N_ok}(0) & H_{N_ok}(\Delta_f) & H_{N_ok}(2\Delta_f) & \ldots & H_{N_ok}(N_f\Delta_f) \end{bmatrix}$$

$$\begin{bmatrix} F_k(0) & 0 & 0 & \ldots & 0 \\ 0 & F_k(\Delta_f) & 0 & \ldots & 0 \\ 0 & 0 & F_k(2\Delta_f) & \ddots & 0 \\ \vdots & \ddots & 0 & \ddots & 0 \\ 0 & 0 & 0 & \ldots & F_k(N_f\Delta_f) \end{bmatrix}.$$

This overdetermined inverse problem in equation (3.2) is suitable for solving using least squares methods to minimize the error in the estimates that are derived from each acceleration channel. The linear least squares best fit of the force estimate can be computed by way of the Moore-Penrose pseudoinverse. However, the present invention contemplates any method for calculating the error in the estimates. Abbreviating equation (3.2) as $[A]=[H_k][F_k]$, the best fit estimate of the diagonal force matrix is given by $[\hat{F}_k]=[H_k]^+[A]$, where $[H_k]^+$ is the pseudoinverse of $[H_k]$.

While the form in equation (3.2) is one representation of the inverse problem, a form used in one embodiment differs slightly, and allows the estimated force spectrum to be represented by a vector, rather than a large diagonal matrix. This modified form is obtained by considering equation (3.1) at one spectral line assuming that only one force is non-zero, as follows:

$$\begin{Bmatrix} A_1(n\Delta_f) \\ A_2(n\Delta_f) \\ \vdots \\ A_{N_o}(n\Delta_f) \end{Bmatrix}_{(N_f \times 1)} = \begin{Bmatrix} H_{1k}(n\Delta_f) \\ H_{2k}(n\Delta_f) \\ \vdots \\ H_{N_ok}(n\Delta_f) \end{Bmatrix}_{(N_f \times 1)} F_k(n\Delta_f). \qquad (3.3)$$

Abbreviating equation (3.3) as $\{A(nD_f)\}=\{H_k(nD_f)\}F_k(nD_f)$, the best fit estimate of the force at the nth spectral line is written as:

$$\hat{F}_k(n\Delta_f)=\{H_k(n\Delta_f)\}^+\{A(n\Delta_f)\}. \quad (3.4)$$

Combining all equations in the form of equation (3.4) for $n=0, 1, 2, \ldots, N_f$ into one equation yields the form that is used in the actual implementation of this algorithm:

$$\begin{Bmatrix} \hat{F}_k(0) \\ \hat{F}_k(\Delta_f) \\ \hat{F}_k(2\Delta_f) \\ \vdots \\ \hat{F}_k(N_f\Delta_f) \end{Bmatrix} = \begin{Bmatrix} \{H_k(0)\}^+\{A(0)\} \\ \{H_k(\Delta_f)\}^+\{A(\Delta_f)\} \\ \{H_k(2\Delta_f)\}^+\{A(2\Delta_f)\} \\ \vdots \\ \{H(N_f\Delta_f)\}^+\{A(N_f\Delta_f)\} \end{Bmatrix}. \quad (3.5)$$

The new method presented according to some embodiments of the present invention here includes an algorithm for estimating the location of the unknown force. The algorithms considered begin with the first step: to calculate the estimated force spectra assuming that the force acted at each of the possible input locations. After this step, $N_i$ force spectra have been estimated, all but one of which is a numerical solution to an inverse problem that does not correspond to the actual physical event that occurred.

A method according to one embodiment of the present invention analyzes the time-histories of the force estimates, which are generated by taking the inverse discrete Fourier transforms of the estimated force spectra. The time domain representation of the signal combines many frequency components together; therefore, a bandwidth of the measurement is considered at once. Realistic force histories are identified by characterizing how well force time histories correspond to the assumption of an impulsive forcing function. Although some embodiments pertain to analysis of the hypothetical forces in the time, yet other embodiments of the present invention pertain to analysis of the hypothetical forces in the frequency domain.

Entropy in information theory is used in some embodiments as a discriminant between force histories that correspond to impact events and those that are the numerical solution to a non-physical problem. Information is generally regarded as an abstract idea and is evaluated qualitatively, but to serve a practical purpose in calculations, it should be quantified. In this sense, information is quantified by the number of bits that are required to describe that information. For example, consider a series of coin tosses. One coin toss can be directly represented by one bit, by representing heads by a 1, and tails as a 0, for example. So for one coin toss, the outcome of one trial, which has 2 possibilities, can be represented by one bit. Similarly, if there were three coin tosses, there would be $2^3=8$ possible outcomes, and three bits would fully describe the particular sequence, so there would be three bits of information in three coin tosses. In a general sense, if there are N possible outcomes of a set of trials, the amount of information given by those trials, I, in bits, is:

$$I=\log_2(N). \quad (3.6)$$

This definition matches the expectation from the coin toss example, as the number of possibilities in n coin tosses is $2^n$, so the amount of information in n coin tosses is $\log_2 2^n = n$ bits. Rather than considering the total amount of information in a set of data, the average amount of information per element in that set, defined as H, could be considered:

$$H = \frac{1}{n} \quad (3.7)$$

This measure of information per sample is defined as entropy. In the case of the fair coin toss, the entropy of that process would be 1 bit, which is consistent with expectations, because 1 bit is used to represent each toss. Entropy in this sense is the means of identifying the force-time history that best corresponds to an impulsive force. To explain the way that entropy is calculated in the case of evaluating recreated force-time histories, a useful example is a set of n tosses of an unfair coin, which has a probability p1 of heads and a probability $p_2=1-p_1$ of tails, where in general $p_1 \neq 0.5$. Assuming a suitably large number of coin tosses, n, the number of occurrences of heads will be given by $m=p_1 n$. While there were $N=2^n$ possible outcomes of n tosses of a fair coin, the number of possible outcomes of n tosses of this unfair coin is given by:

$$N = \binom{n}{m} = \frac{n!}{m!(n-m)!} \quad (3.8)$$

From the previous definition of information, the amount of information in this set of trials is given by:

$$I = \log_2(N) = \log_2\binom{n}{m} = \log_2 \frac{n!}{m!(n-m)!} \quad (3.9)$$

Writing this expression for information in terms of the base e rather than 2 and re-arranging, equation (3.9) can be written as:

$$I = \frac{1}{\ln(2)}(\ln(n!) - \ln(m!) - \ln((n-m)!)) \quad (3.10)$$

Using Sterling's approximation for the natural logarithm of a factorial, $\ln(n!) \approx n\ln(n)-n$ for n ( ) large, equation (3.10) becomes:

$$I = \frac{1}{\ln(2)}(n\ln(n) - m\ln(m) - (n-m)\ln(n-m)) \quad (3.11)$$

After straightforward algebra, which is omitted for brevity, and returning to logarithms of the base 2, equation (3.11) is written as:

$$I = m\log_2\left(\frac{m}{n}\right) - (n-m)\log_2\left(\frac{n-m}{n}\right) \quad (3.12)$$

Equation (3.12) is now written in terms of probabilities p1 and p2, giving the final expression for information:

$$I=np_1 \log_2(p_1)-np_2 \log_2(p_2) \quad (3.13)$$

Finding the average information per toss gives the entropy of the process as follows:

$$H=-p_1 \log_2 p_1-p_2 \log_2 p_2 \quad (3.14)$$

Plotting the entropy as a function of probability heads, as in FIG. 13.5, helps to explain how entropy changes based on the characteristics of the underlying process. The entropy is maximized when both events are equally likely, where the entropy is 1 bit, as expected from the previous discussion of a fair coin toss. When there is less uncertainty in the outcome, that is, either heads or tails is more likely to occur, the entropy is less. At the extremes, if the probability of heads approached 100% or 0%, the entropy would be zero. This result makes sense, because in either of these cases, with a knowledge of the probability beforehand, no information is gained by each toss of the coin; the outcome of every trial was already known.

Two characteristics of entropy in general can be drawn from this example of two possible outcomes. The entropy is maximized when each k possible outcomes is equally likely, where entropy approaches a maximum value of $H_{max} = \log_2(k)$. Second, the minimum entropy approaches zero as the probability of one possible outcome approaches 1.

In more practical cases, there exist more than two possible outcomes. The form of entropy in the case of two outcomes, as in equation (3.14), extends to the case with k possible outcomes, each of which has a probability of pi, as follows:

$$H = \sum_{i=1}^{k} -p_1 \log_2 p_i \qquad (3.15)$$

In this application, equation (3.15) is implemented to find the entropy of a recreated force signal by dividing the signal into a set number of equally spaced bins, and then finding the number of samples that fall into each bin. These frequencies of occurrence are divided by the total number of samples to give probabilities that the signal falls into each bin range. The entropy is then calculated according to equation (3.15). To illustrate the process, two example signals are considered that each consist of ten samples that range in value from 0 to 1. These signals are intended to be a simple example of how a signal that consists of just one pulse has a lower entropy than one that is more random. Five bins will be used to find the entropy of each of the signals, which are given in Table 3.1. Table 3.2 shows the results at each step of the entropy process as well as the final value. The probability of the signal falling into each bin is calculated, and then the contribution to the entropy total is listed for each bin. Finally, the values are summed to find the total entropy of each signal. In this example, the simple pulse signal has an entropy of 0.47 bits, while the random signal has an entropy of 2.32 bits.

Although what has been shown and described is the use of entropy to categorize the various hypothetically calculated forces, yet other embodiments are not so constrained. It is to be understood that in general, various methods described herein pertain to the quantification of the randomness of the predictions made by the model. Although the calculation of signal entropy is included in one method, yet other embodiments are not so constrained. For example, the loads predicted by the model can be analyzed in any manner to statically determine the likelihood of one hypothetical load in comparison to another hypothetical load, and thereafter categorizing the results as less likely to have happened (i.e., higher levels of randomness), or more likely to have happened (i.e., lower levels of randomness).

In addition, the predicted hypothetical loads can be sorted in terms of their likelihood of having occurred (i.e., randomness) based on observations pertaining to the hypothetical forces, and categorizing the hypothetical forces based on those observations. As one example, in one embodiment, the hypothetical forces are predicted in the time domain, and these hypothetical forces are assessed as to their relative amounts of higher frequency content occurring before or after the hypothetical impact (especially with those force identification systems in which the unknown load is characterized as an impact). As yet another example, in some embodiments the hypothetical loads are examined in the frequency domain, and those hypothetical loads having higher frequency content are considered to be less likely than those hypothetical loads having a reduced amount of high frequency content.

In yet other embodiments, the randomness of the predictions are quantified based on the total information content of the signal, quantified in bits, which is calculated. Although entropy is the rate of change of information per sample, in one embodiment the total information could be calculated directly as well. This quantity would be the minimum lossless compression size (i.e., how few bits the signal could be represented with without losing any information about the signal).

In yet other embodiments, the signature of each hypothetical force (either time-based or in the frequency domain) can be compressed with any compression algorithm. The file size of each compressed hypothetical force could be considered a measure of randomness (i.e., larger files would be more random).

In yet other embodiments, the concentration of energy in the time domain is representative of the randomness of the signal (i.e., less concentrated energy represents a more random signal). This concentration can be calculated first by finding the signal energy in several segments of the signal, and then the ratio of the average signal energy to each segment. The inverse of the relative energy of the segments with the larger relative energies is representative of increasing randomness of the signal.

In yet other embodiments, the randomness of the signal can be quantified in the time domain. The number of oscillations above a certain threshold can be representative of how random the signal was. To quantify this in one embodiment, a threshold value is subtracted from the signal, and the number of times this difference crosses zero is representative of how random the signal is (how many oscillations above that threshold are present).

TABLE 3.1

Two simple example signals are used to represent a signal with a single pulse and one that is more random.

| | Values | | | | | | | | | |
|---|---|---|---|---|---|---|---|---|---|---|
| Signal 1 | 0.0 | 0.0 | 0.0 | 0.0 | 1.0 | 0.0 | 0.0 | 0.0 | 0.0 | 0.0 |
| Signal 2 | 0.75 | 0.17 | 0.3 | 0.54 | 0.37 | 1.0 | 0.7 | 0.9 | 0.0 | 0.58 |

TABLE 3.2

The entropy calculation process is demonstrated for two simple example signals.

| | Signal 1 | | | Signal 2 | | |
|---|---|---|---|---|---|---|
| Bin | Count | $p_i$ | $-p_i \log_2 p_i$ | Count | $p_i$ | $-p_i \log_2 p_i$ |
| 0.00–0.19 | 9 | 0.9 | 0.137 | 2 | 0.2 | 0.4644 |
| 0.20–0.39 | 0 | 0 | 0 | 2 | 0.2 | 0.4644 |

TABLE 3.2-continued

The entropy calculation process is demonstrated for two simple example signals.

| Bin | Signal 1 | | | Signal 2 | | |
|---|---|---|---|---|---|---|
| | Count | $p_i$ | $-p_i \log_2 p_i$ | Count | $p_i$ | $-p_i \log_2 p_i$ |
| 0.40-0.59 | 0 | 0 | 0 | 2 | 0.2 | 0.4644 |
| 0.60-0.79 | 0 | 0 | 0 | 2 | 0.2 | 0.4644 |
| 0.80-1.00 | 1 | 0.1 | 0.3322 | 2 | 0.2 | 0.4644 |
| Total | 10 | 1 | 0.469 | 10 | 1 | 2.322 |

In order to study the impact identification process separate from the effects of noise and other measurement error, an analytical model was created for use in simulations. This model is based on the modal properties of the aluminum square plate that was tested. Modal parameter estimation algorithms were used to extract the modal properties from the experimental test data. With a model that accurately simulates the behavior of a thin plate, each step of the impact identification process is studied in detail.

In order to create a model that has properties representative of an actual test specimen, the modal parameters from a set of modal impact data is used to create the model. A 12 DOF model is used with 49 input measurement degrees of freedom and 3 output degrees of freedom by using the modal frequencies, vectors and participation factors from the first 12 modes of the plate. Denoting the modal frequencies as $k_r$, the matrix of modal vectors as $[\Psi]$, and the modal participation matrix as $[L]$, the modal decomposition for a system of model order m is given by:

$$[H(j\omega)]_{(N_i \times N_o)} = [\Psi]_{N_i \times m} \begin{bmatrix} \ddots & \cdots & 0 \\ \vdots & \frac{1}{j\omega - \lambda_r} & \vdots \\ 0 & \cdots & \ddots \end{bmatrix}_{(m \times m)} [L]^T_{m \times N_o}. \quad (3.16)$$

Equation (3.16) is used first to decompose the measured frequency response function into the modal properties of the system, then to recreate analytical frequency response functions based on the estimated modal parameters. A two stage solution procedure is used to solve for the parameters, where each of the two stages is linear. A high order time domain modal parameter estimation algorithm called Poly-Reference Time Domain (PTD) is used first to solve for the modal frequencies and modal participation factors, and then the modal vectors are found using a high order time domain multiple reference residue estimation algorithm.

Polyreference Time Domain (PTD) is a high order time domain algorithm that is based on a polynomial characteristic equation with matrix coefficients. A system with Ne effective degrees of freedom has equations of motion defined by the following matrix polynomial in the Z-domain with matrix coefficients of dimension $N_e \times N_e$, for reference p:

$$[z^2[I]+z[\alpha_1]+[\alpha_0]]\{H_p(z)\}=\{0\} \quad (3.17)$$

The frequency response function can be reduced from Ne effective degrees of freedom to a smaller number, NS degrees of freedom by using a higher order, N>2. This change exchanges a lack of spatial information for more temporal information, which is what makes this algorithm a "high order" estimation algorithm. After this reduction of matrix coefficient size, the equations of motion, with matrix coefficients size $N_S \times N_S$ are given as follows:

$$[z^N[I]+z^{N-1}[\alpha_{m-1}]+ \ldots +[\alpha_0]]\{H_p(z)\}=\{0\} \quad (3.18)$$

Moving the highest order term to the right side, an equation for each reference p can be written, where $\{H_p(z)\}$ is size $1 \times N_S$, the transpose of $\{H_p(z)\}$ in the previous equation, and as a result, the $[\alpha]$ matrices are transposed accordingly, as follows:

$$[z^{2N-1}\{H_p(z)\} \quad z^{2N-2}\{H_p(z)\} \quad \ldots \quad z\{H_p(z)\} \quad z^0\{H_p(z)\}] \quad (3.19)$$

$$\begin{bmatrix} [\alpha_{2N-1}]^T \\ [\alpha_{2N-2}]^T \\ \vdots \\ [\alpha_1]^T \\ [\alpha_0]^T \end{bmatrix} = -z^{2N}\{H_p(z)\}_{1 \times N_S}.$$

Repeating this equation for each reference, the entire discrete frequency response function matrix H(z) is used, meaning that all of the spatial data available are contributing to the estimates of the matrix coefficients. The following equation forms the basis for PTD:

$$[z^{2N-1}[H(z)] \quad z^{2N-2}[H(z)] \quad \ldots \quad z[H(z)] \quad z^0[H(z)]] \quad (3.20)$$

$$\begin{bmatrix} [\alpha_{2N-1}]^T \\ [\alpha_{2N-2}]^T \\ \vdots \\ [\alpha_1]^T \\ [\alpha_0]^T \end{bmatrix} = -z^{2N}[H(z)]_{N_L \times N_S}.$$

The time shift property of the Z-domain, which states $Z^{-1}(z^k X(z))=x(n+k)$, is now employed to return to the discrete time domain, and then the preceding equation is repeated $N_t$ times, with a time shift between each redundant equation in order to form an overdetermined problem in terms of the sampled impulse response function matrices:

$$\begin{bmatrix} [h(n_0+2N-1)] & [h(n_0+2N-2)] & \ldots & [h(n_0)] \\ [h(n_0+2N)] & [h(n_0+2N-1)] & \ldots & [h(n_0+1)] \\ [h(n_0+2N+1)] & [h(n_0+2N)] & \ldots & [h(n_0+2)] \\ \vdots & \vdots & \ddots & \vdots \\ [h(n_0+2N+N_t-1)] & [h(n_0+2N+N_t-2)] & \ldots & [h(n_0+N_t)] \end{bmatrix} \quad (3.21)$$

$$\begin{bmatrix} [\alpha_{2N-1}]^T \\ [\alpha_{2N-2}]^T \\ \vdots \\ [\alpha_1]^T \\ [\alpha_0]^T \end{bmatrix} = \begin{bmatrix} -[h(n_0+2N)] \\ -[h(n_0+2N+2)] \\ -[h(n_0+2N+3)] \\ \vdots \\ -[h(n_0+2N+N_t)] \end{bmatrix}.$$

This equation is now solved by premultiplying both sides by the pseudo-inverse of the left impulse response matrix. With estimates for the matrix coefficients of the characteristic equations, the modal frequencies and modal participation factors are found through a companion matrix solution approach. The estimated matrix coefficients are substituted into a matrix of the following form:

$$[C] = \begin{bmatrix} -[\alpha_{N-1}] & -[\alpha_{N-2}] & \cdots & -[\alpha_1] & -[\alpha_0] \\ [I] & [0] & \cdots & \cdots & [0] \\ [0] & [I] & \ddots & \cdots & [0] \\ \vdots & \ddots & \ddots & \ddots & \vdots \\ [0] & \cdots & \cdots & [I] & [0] \end{bmatrix}_{((N*N_L)\times(N*N_L))} \quad (3.22)$$

where $[I]$, $[0]$, and $[\alpha_i]$ are matrices of dimension ($N_L \times N_L$). The eigenvectors, $\{\phi_r\}$, and eigenvalues, $z_r$, of this companion matrix yield the modal frequencies, $\lambda_r$, and modal participation vectors, $\{L_r\}$, through the following relationships:

$$z_r = e^{\lambda_r \Delta_t}, \quad (3.23)$$

$$\{\phi_r\} = \begin{Bmatrix} z_r^{(N-1)}\{L_r\} \\ z_r^{(N-2)}\{L_r\} \\ \vdots \\ \{L_r\} \end{Bmatrix}. \quad (3.24)$$

After the first stage, using PTD, both the modal frequencies and the modal participation factors are known. Using this information, the last piece of information in the modal decomposition can be found: the modal vectors. The basic equation for this method is as follows:

$$\{h_p(n)\} = \begin{bmatrix} L_{11} & L_{12} & \cdots & L_{1(2N)} \\ L_{21} & L_{22} & \cdots & L_{2(2N)} \\ \vdots & \vdots & \ddots & \cdots \\ L_{N_S 1} & L_{N_S 1} & \cdots & L_{N_S(2N)} \end{bmatrix} \begin{bmatrix} z_1 & 0 & \cdots & 0 \\ 0 & z_2 & 0 & \vdots \\ \vdots & 0 & \ddots & 0 \\ 0 & \cdots & 0 & z_{2N} \end{bmatrix}^n \begin{Bmatrix} \psi_{p1} \\ \psi_{p2} \\ \vdots \\ \psi_{p2N} \end{Bmatrix}, \quad (3.25)$$

where $z_r \equiv e^{\lambda \Delta_t}$, thus $z_r^n = e^{\lambda_r n \Delta_t}$.

To create an overdetermined system of equations, this equation must be repeated for $N_t$ time steps, which leads to the final equation to be solved for the modal vectors. For convenience, the modal participation matrix will be abbreviated $[L]$, and the diagonal matrix of $z_r$ values will be denoted $[Z]$. The overdetermined matrix equation that is solved with standard pseudoinverse methods to find the modal vectors is as follows:

$$\begin{Bmatrix} \{h_p(n_0)\} \\ \{h_p(n_0+1)\} \\ \vdots \\ \{h_p(n_0+N_t)\} \end{Bmatrix}_{N_t(N_S)\times 1} = \begin{bmatrix} [L][Z]^1 \\ [L][Z]^2 \\ \vdots \\ [L][Z]^{N_t} \end{bmatrix}_{N_t N_S \times 2N} \begin{Bmatrix} \psi_{p1} \\ \psi_{p2} \\ \vdots \\ \psi_{p2N} \end{Bmatrix}. \quad (3.26)$$

The impulse response data from the modal impact test on the square plate is first decimated by a factor of 5 in order to limit the frequency range considered to 0-1250 Hz. The modal properties of the system are estimated as described above for model orders between 20 and 46, in increments of two. Although one model order is only 12, a higher order is generally required for experimental data. The real modes of the system are distinguished from computational estimates that do not correspond to physical dynamics by using several increasing model orders and examining which modes have parameters that are consistently estimated.

These results are visualized using a consistency diagram, as in FIG. 13.6. In this figure, the Complex Mode Indicator Function (CMIF) of the frequency response function matrix is shown in the background in black for reference. The CMIF is the plot of the singular values of the FRF matrix at each spectral line. The CMIF indicates frequencies that likely correspond to modes, and indicates the presence of closely spaced or repeated roots at locations where more than one singular value reaches a local maximum. The frequency of an estimate is considered stable if the imaginary portion of the modal frequency is within 1 rad/s of the estimate from the previous iteration, the pole is considered stable if the difference between both the real and imaginary portion of the modal frequencies is less than the same threshold, and the vector is considered stable if the Modal Assurance Criterion (MAC) between successive estimates has a value greater than 0.85. The consistency diagram shows that at the final model order, each of the modes identified by the indicator function is estimated consistently. Table 3.3 shows the modal frequencies that were identified.

With the modal parameters estimated, the frequency response functions for the model are evaluated with (3.16). A comparison of an example measured frequency response function and the synthesized frequency response function between the same measurement degrees of freedom, shown in FIG. 13.7, verifies that the model effectively simulates the response of the plate. The discrepancy between the measured and synthesized frequency response functions at the high end of the frequency range can be explained by two main reasons: (1) the residual stiffness from higher frequency modes of vibration, and (2) the low-pass anti-aliasing filter used when decimating the impulse response function. Decimation of the impulse response function involves low pass filtering the impulse response function with a digital filter that has a cut-off frequency of $0.8*f_s/(2*R)$, where R is the ratio that the signal is decimated by. In this instance, the cut-off frequency of the anti-aliasing filter is 1000 Hz, so the frequency response function above 1000 Hz is significantly attenuated.

TABLE 3.3

The modal frequencies for the plate model are shown as identified through experimental modal analysis.

| | Modal Frequency Estimates | |
|---|---|---|
| Mode Number | $f_d$(Hz) | $\zeta$(%) |
| 1 | 21.12 | 9.459 |
| 2 | 30.00 | 10.701 |
| 3 | 31.27 | 8.262 |
| 4 | 229.72 | 0.991 |
| 5 | 329.26 | 0.158 |
| 6 | 420.96 | 1.013 |
| 7 | 585.23 | 0.565 |
| 8 | 593.35 | 0.517 |
| 9 | 1031.24 | 0.297 |
| 10 | 1050.02 | 0.280 |
| 11 | 1080.61 | 0.282 |
| 12 | 1159.52 | 0.126 |

To simulate the effects of windowing and sampling on the frequency response functions used for inversion, the impulse response function is sampled and windowed, at a sampling frequency of 10 kSa/sec, and a rectangular window 2.56 seconds in duration, and then the discrete Fourier transform of that impulse response function is used to find the FRF, rather than simply sampling the continuous frequency response function. The sampling frequency is chosen such that the highest modal frequency is much less than the Nyquist frequency to limit the effects of aliasing, but if a sampling frequency closer to the highest frequency in the impulse response was desired, the impulse response function could be evaluated at a high sampling frequency, and then decimated to obtain an impulse response function without significant aliasing error.

With the impulse and frequency response function matrices determined, the response of the system to an impact at each location is simulated for use in evaluating the impact identification algorithm. The force pulse is chosen as a squared Hann window function, with a 4.1 ms duration and unity amplitude. The force signal is zero other than during the pulse. The response is found by convolving a simulated force signal with the impulse responses corresponding to each location. This convolution is computed by zero-padding the impulse response and force signals to twice their lengths, multiplying the DFT's of the two signals, calculating the inverse DFT of that product, and truncating the resulting signal to the appropriate length. With response signals due to impacts at points in the structure simulated, responses can be passed to the impact identification algorithm.

In order to show the progression of the impact identification algorithm, the simulated response from an impact to a representative point was used as a test case. With the pseudoinverse matrix calculated as described in Section 3.2.2, the force spectrum is estimated assuming that the force acted at each of the possible impact points, and the estimated force time histories are found by the IDFT of the estimated spectra. FIGS. 13.8A, 13.8B, 13.8C, 13.8D, 13.8E, 13.8F, 13.8G and 13.8H show the estimated forces from three locations along with the actual force input. For the incorrect locations, differences are evident in both the frequency and time domain. While the estimated force time history for the correct location is a single pulse, the estimated forces for the incorrect locations are more spread out, particularly for the second example incorrect location. In the frequency domain, differences are also evident, although the overall trend of the force spectrum shape is preserved. With force estimates generated for each possible impact location, these recreated forces are analyzed to identify the most likely point of impact.

An entropy-based method according to one embodiment of the present invention is evaluated for the response data. With the recreated time histories estimated, the entropy of each is calculated for the first 0.3 seconds of the signal, and the resulting entropy values are plotted in FIGS. 13.9A and 13.9B. The entropy-based method also identifies the correct location, but with better discrimination between the correct location and the incorrect locations. The entropy value 70 for the correct location is calculated to be 0.12, and the second lowest entropy value is 1.64. As shown in the box plot in FIG. 13.9B, the value for the correct location is an outlier.

The example presented here is for an impact force applied to the starboard side sponson. This impact force is correctly located with the entropy-based impact identification algorithm. The first aspect of one impact identification algorithm is to estimate the force spectrum assuming that the impact occurred at each of the possible impact locations. The estimated force spectrum for the actual impact location is plotted in FIG. 14.1, along with the actual force of the impact, as measured by the impact hammer used. Although the overall shape of the force spectrum is mostly preserved for some frequency ranges, the fit is noisy, and the fit is poor for the low frequencies, up to approximately 200 Hz.

The same data is used to calculate recreated frequency response functions for each response channel using the estimated force spectrum. The frequency response function between the point on the starboard sponson that is impacted and the middle accelerometer in the direction normal to the skin is chosen for comparison. The measured frequency response function is compared to the recreated frequency response function in FIGS. 14.2A and 14.2B. The errors in the force estimation result in poor agreement with known magnitude values for the low and high frequency ranges, with some ranges in the middle of the excitation bandwidth that agree well. Much like the shape-based method, however, a frequency range that agrees well for impacts to all areas of the aircraft cannot be found because the bandwidth of impacts to the structure is highly variable.

A method that combines the phase and magnitude information across many possible impact locations is needed to compensate for the challenges with a large structure. The consideration of the estimated force signal in the time domain helps to accomplish this task. By considering the time-history of the estimated force, many components in the frequency bandwidth of the impact are combined. The phase information establishes at what point in time the impact occurs, and has a significant effect on the shape of the force signal. In order for the force signal to appear as a single pulse in the time domain, the relative phase of each frequency component should be correct. The entropy of the force-time history is calculated for possible impact locations, and the points that best match the form of a single pulse will have the lowest associated entropy values. In FIG. 14.3 is shown the entropy value corresponding to each point on the aircraft plotted against the distance from the actual impact point for this example. The trend of increasing entropy with distance from the correct location remains, and the correct location has the lowest associated entropy value. It is appreciated that in some embodiments, it is not necessary or even desirable to locate the lowest entropy value, but rather to separate areas of relatively low entropy from areas of relatively high entropy. In so doing, the task of identification of the location (and its subsequent repair) is established over the region of the structure having generally lower entropy values. Further, it may be possible to generally ignore those areas having higher entropy values. In so doing, the point of impact is not identified. Rather, regions are identified where impact is more likely, and regions are identified where impact was less likely.

TABLE 4.2

The location identification accuracy of the entropy-based method on the helicopter fuselage is summarized here.

| Distance Error | 0 | ≤6 in | ≤9 in | ≤12 in | ≤15 in | ≤18 in |
| --- | --- | --- | --- | --- | --- | --- |
| Port Side | 92.7% | 96.3% | 97.4% | 97.9% | 98.0% | 98.5% |
| Starboard Side | 89.8% | 96.7% | 97.4% | 98.5% | 98.7% | 99.0% |

The overall performance of the entropy-based method for identifying impacts to the helicopter fuselage is quantified by testing the response from two impacts to each point on the port side of the aircraft, and three impacts to each point on the starboard side. The location identification accuracy is summarized in Table 4.2. Results show that 93% of impacts to the port side of the helicopter are located to the nearest point, and 97.4% of impacts are located within 9 inches. The starboard simulation showed that 89.8% of impacts on the starboard side are located at the correct grid point, and 97.4% of the validation points are located within 9 inches of the correct location.

One result from the validation simulations is that the error in location accuracy is not found to increase with distance from the sensor. In fact, the largest errors in location accuracy are obtained when impacts are close to the sensors. Over-ranging of the accelerometer is observed to distort the response measurement in this instance. In FIG. 14.4 is shown the position identification error on the grid, with dot size proportional to the position identification error. The largest error is above the retrofitted carbon fiber panels, where the rearmost accelerometer is mounted, and another problem area is found towards the front of the aircraft near the engine nacelle, which is close to where the front sensor is mounted. The independence of error from distance to the sensors is useful for applying impact identification to large structures. The problem area near the front is likely a result of a worn latch mechanism on the front window, which fails to preload the window against the fuselage. The lack of preload on this interface allows the window to alternate from being in and out of contact with the fuselage when the window is struck, resulting in a non-linearity that is observed qualitatively as "rattling." This rattling behavior is dependent on the magnitude of impact force, which cannot be controlled in an impact identification scenario.

In the time domain, errors in force estimation can manifest themselves in energy from the main pulse that "leaks" into adjacent portions of the time history. This spread of signal energy reduces the magnitude of the main pulse, which leads to underestimation of the impact force amplitude. To return the energy back into the main pulse, the width of the main pulse is identified, and a window is applied to the force time history around that pulse, which results in a restricted hypothetical load. The energy of the windowed signal will be less than the original signal, because some portions of the signal have been removed by the window. To return that lost energy to that restricted hypothetical load, the windowed force time history is scaled to equalize the signal power before and after windowing. In FIGS. 13.9A and 13.9B are shown the results of applying this method to the force estimate for an impact to the starboard sponson 10.

Although what has been shown and described herein are equalization methods in which either the signal power or the signal energy is used as a factor in correcting the hypothetical load, yet other embodiments are not so constrained. In some embodiments, the chosen hypothetical load (or loads) are restricted by eliminating their high frequency content (in the frequency domain), and applying the inverse Fourier transform to that restricted frequency content.

Yet other embodiments of the present invention pertain to a method that allows for the detection of several impacts acting within the sampling window. The method is broken down into the following: extract the envelope 201 of the response signal. Use the response envelope to identify the time duration 202 for which the response resulting from one particular impact dominates. Split the response signal 203 into as many signals as there are impacts, and window the response accordingly for the impacts. Apply an impact identification method to estimate the location and magnitude 204 of the separate impacts.

The application of these additional aspects during pre-processing provides the ability to identify impacts acting in quick succession. Before the method for separating multiple impacts is applied, a decision is made on whether a response signal is in fact the result of more than one impact. To make this decision, an algorithm for finding extrema in noisy data is used, with a threshold of ⅙th the signal's range. If more than one distinct maximum in the response signal is found to exceed this threshold, then the multiple impact detection algorithm is used.

One aspect in determining the portions of the response time history pertaining to a particular impact is extracting the envelope 201 of the response signal. The envelope of the signal is found in some embodiments using the Hilbert transform, and then that envelope is filtered with a low-pass filter in order to capture the shape of the envelope that is relevant to the task of identifying response windows. It is understood that the present invention is not constrained to use of the Hilbert transform, and contemplates any method of establishing the shape of a response envelope.

The Hilbert transform is an all-pass filter that imparts a 90° phase shift on the signal. The frequency response of the Hilbert transform is defined as:

$$H_{Hilbert}(j2\pi f) = \begin{cases} -j & f > 0 \\ 0 & f = 0 \\ +j & f < 0 \end{cases} \quad (4.1)$$

Denoting the Hilbert transform of a signal x(t) as x̂(t), the envelope of the signal can be related to the analytic signal, which is defined as:

$$a_x(t) = x(t) + j\hat{x}(t) \quad (4.2)$$

Then the envelope of the signal, A, is found by taking the magnitude of the analytic signal as follows:

$$A = \sqrt{x(t)^2 + \hat{x}(t)^2} \quad (4.3)$$

The Hilbert transform of the signal is found by way of a finite impulse response filter. The Hilbert transformer filter is designed by sampling and windowing the analytical expression for band limited Hilbert transform. The Hilbert transformer filter is applied to the response, and the result is used to estimate the analytic signal. The analytic signal is used to calculate the envelope of the response signal.

In some embodiments, the Hilbert transform (or approximations thereof) can be used to extract an approximate envelope, but other methods are used in other embodiments. In those embodiments in which that envelope will be low-pass filtered, the quality of the envelope is not as critical. One example of a method that can be used to approximate the envelope includes taking the absolute values of the time-based signals. After low pass filtering the absolute values, it is possible to extract an estimate of the envelope of the response that would be satisfactory. Yet another example includes fitting a polynomial or other smooth interpolation function to peaks in the response signal, from which can be extracted a reasonable estimate of the envelope.

The envelope of the signal is then passed through a low pass filter to isolate the low frequency trends in the envelope, which are indicative of the response from each impact. The low pass filter is implemented as a zero-phase FIR filter in order to accurately identify the times at which the impacts occur. The filter in some embodiments is designed by using the Parks-McClellan algorithm for optimization. To reduce oscillations in the low pass filter's frequency response, the impulse response of the filter is windowed with a Hann window. The pass band is selected as 0-10 Hz, and the stop band is set to 15 Hz–$f_s/2$ Hz. The period of the minimum frequency of the passband is $1/10$ Hz=0.1 seconds, so impacts occurring at least this far apart can be distinguished.

In order to demonstrate the process of extracting a usable envelope of a response signal from multiple impacts, a simulated response is generated by adding a time-delayed response signal to the original signal, shown as the thin blue line in FIGS. 14.5A and 14.5B. Then, the envelope calculated from the Hilbert transform based method is also plotted in green, along with the low-pass filtered envelope in red, which is the signal that is used to determine the time intervals of each impact.

To identify the portions of the response due to a particular impact, in one embodiment the local minima in the filtered envelope between the peaks are found, and then the range extremes are set at a point in time that corresponds to the filtered envelope rising above a certain threshold. This sets the range for each impact wider than if the minima were used as the limits, without allowing the signals before and after to have too much of an effect. Once the ranges for the response due to each impact are determined, windows are generated for each impact that are zero outside of the identified range, and a Tukey window with 15% taper is applied within the identified range. To illustrate the window range selection process and window choice, a simulated response to four impacts is shown in FIG. 14.6 with the intermediate steps and the window for each impact, which are scaled for display purposes. The response signal is windowed by each of these windows separately, and for each impact, the signal with the appropriate window applied is passed to the impact identification algorithm as normal. This process changes one response that is caused by several impacts to several response signals, each primarily a result of one impact, and the correct time duration is obtained for the impact identification algorithm. Although what has been shown and described is a specific method for identifying responses that are the result of multiple impacts to a structure, it is understood that yet other embodiments of the present invention are not so constrained, and contemplate other methods for detecting local minima; for detecting separation between impacts based on criteria other than local minima; applying windows other than a Tukey window; and applying windows with different amounts of taper, including no taper, as examples.

Although what has been shown and described is a method of identifying and placing windows based on a low pass filtering of the Hilbert transform, yet other embodiments are not so constrained. For example, in one embodiment, a Fourier transform of the multiple impact signal includes (again, referring to FIG. 14.6) some frequency content in the region of three to four Hertz. Assuming that this frequency content is less than the fundamental frequency of the portion of the structure where the hypothetical loads are calculated, then such a low frequency can be used to approximate the number of windows to be used. In the example shown in FIG. 14.6, the frequency component in the DFT from the separate impacts would yield an estimate of the number of windows to be provided as three or four (i.e., the value of the low frequency component is converted to an integer or range of integers since the impacts are discrete events).

In order to test the effectiveness of this algorithm for identifying multiple impacts, data from 45 groups of impacts in rapid succession applied at multiple locations on the port side of the fuselage were recorded. Fifteen groups each of impacts with three, four, or five impacts within the sampling window were recorded, and these groups of impacts were each repeated three times. The location identification accuracy from these tests is summarized in Table 4.4. Over 90% of impacts were located within 15 inches of the actual location. As the number of impacts within the time window increased, less impacts were correctly located, but the performance within 12 inches of the correct location is similar between the sets of data from three, four, and five impacts per sampling window.

TABLE 4.4

The location identification performance of the multiple impact detection algorithm is summarized here.

| Distance Error | 0 | ≤6 in | ≤9 in | ≤12 in | ≤15 in | ≤18 in | Missed |
|---|---|---|---|---|---|---|---|
| 3 Impacts/Time Window | 66.9% | 81.2% | 85.7% | 88.7% | 91.0% | 93.2% | 1.5% |
| 4 Impacts/Time Window | 66.3% | 79.1% | 83.1% | 87.8% | 91.3% | 91.9% | 4.4% |
| 5 Impacts/Time Window | 52.6% | 77.5% | 83.6% | 86.9% | 90.1% | 91.6% | 5.3% |

An example time history from one accelerometer channel in response to five impacts is shown in FIG. 14.7, showing the overlap between the responses due to separate impacts. The force time history along with the estimated forces from each impact are shown for the same dataset in FIG. 14.8.

Yet other embodiments of the present invention pertain to the simplication of signal processing when identifying the location and/or magnitude of loads on a structure, especially a non-homogeneous structure. The effects of three potential sources of error are investigated: (1) Lower Sampling Frequency, (2) Lower Analog-to-Digital Converter (ADC) Resolution and (3) Lack of Pre-Trigger Response Data. In order to investigate the effects of these sources of error, the response data from the modal impact tests used to train the canister FRF model are passed through the impact identification algorithm, and the recreated forces and estimated impact location are compared to the actual measured values to quantify error.

All simulations are based on modal impact test data taken from a grid of 64 points on a healthy test canister. The data was taken with a sampling rate of 25.6 kHz, and the frequency response for five impacts per point are averaged together with the H1 frequency response function (FRF) estimator in order to minimize the effects of noise on the response data. The average FRF at each point is used to build a pseudoinverse matrix to be used in impact identification. The entropy-based impact identification method is used to test accuracy, and the raw force estimate, rather than one refined with additional post-processing, is used for amplitude error testing.

For impacts to the canister with a brass tip, which excites a broad frequency range, force estimation errors are found to increase with a lower sampling frequency, because an increasing portion of the force energy is in the frequency range beyond half of the lowered sampling frequency as the sampling frequency decreases. To simulate the effect of this lowered sampling frequency, a low-pass filter is used to recreate the effect of the anti-aliasing filter that would be used for a lower sampling frequency. An eighth order Chebyshev Type I IIR filter is used with a cut-off frequency of 8/10ths the simulated sampling frequency to simulate an anti-aliasing filter. In order to correct for the phase error introduced by filtering, the signal is sent through the filter both forwards and backwards to cancel out the phase distortion. The original data is sampled at 25.6 kSa/sec, and several sampling frequencies ranging from the original to one-tenth the original are tested. The position identification accuracy and average percent error in maximum force amplitude for a variety of sampling frequencies are summarized in Table 5.1, and the peak force amplitude error is depicted graphically in FIG. 15.1. It can be seen that in some embodiments, reasonably accurate impact location is achieved for sampling frequencies slower than about three thousand samples per second. Further, it can be seen that about ten percent accuracy in force magnitude is achieved if the sampling frequency is greater than about six thousand samples per second (in terms of the mean error). Each of the rows in Table 5.1 represent ranges of preference for sampling frequency in some embodiments of the present invention. As one example, in some embodiments, reasonable accuracy in predicting the both the location and magnitude of the force can be achieved with sampling frequencies less than about ten thousand samples per second. In yet other embodiments, reasonable accuracy in predicting the location and magnitude of the peak force can be obtained with sampling frequencies less than about four thousand samples per second.

TABLE 5.1

The effect of lowered sampling frequency on impact identification performance is evaluated using simulations.

| Simulated | Impacts | Peak Force Error Statistics | | | | |
|---|---|---|---|---|---|---|
| Sampling Frequency | Correctly Located (%) | Mean (%) | Std. Dev. | Median (%) | Min (%) | Max (%) |
| Original | 100 | 3.85 | 3.44 | 2.84 | 0.06 | 14.34 |
| 12.8 kSa/sec | 100 | 4.05 | 3.46 | 3.26 | 0.07 | 14.13 |
| 8.53 kSa/sec | 100 | 5.47 | 5.20 | 3.64 | 0.03 | 26.25 |
| 6.4k kSa/sec | 98.4 | 9.90 | 13.45 | 4.20 | 0.08 | 87.80 |
| 5.12 kSa/sec | 100 | 16.97 | 13.64 | 6.61 | 0.08 | 52.61 |
| 4.27 kSa/sec | 98.4 | 19.29 | 15.50 | 12.91 | 0.35 | 60.54 |
| 3.66 kSa/sec | 100 | 25.90 | 15.74 | 20.50 | 0.62 | 64.04 |
| 3.20 kSa/sec | 99.2 | 32.09 | 15.52 | 26.73 | 3.96 | 68.65 |
| 2.84 kSa/sec | 98.4 | 37.39 | 15.09 | 32.25 | 10.26 | 72.14 |
| 2.56 kSa/sec | 95.3 | 42.05 | 14.97 | 37.26 | 5.63 | 75.19 |

To simulate the effect of acquiring response data with a data acquisition system that has less ADC resolution than the laboratory grade systems used thus far, responses from the modal impact tests used to train the frequency response function model are modified to simulate acquisition with fewer bits of ADC resolution. Two factors influence the resolution of the DAQ system: the number of bits used to encode the signal and the range that the ADC encodes those values over. The effect of both of these factors should be considered, because the number of bits ADC resolution is only sufficient for comparison if the signal of interest is the same amplitude relative to the range of the acquisition. For example, a 1 mV-level signal acquired with a 16 bit DAQ with a range of +/−10V would introduce more quantization error than the same signal acquired with a 15 bit DAQ with a range of +/−2 mV.

In order to simplify this issue into terms of one variable, initial simulations are carried out with a range set so that the signal fills the range of the ADC, and then the number of bits of resolution used is changed. The term "effective bits of resolution" is used to indicate the number of bits of resolution spread out over the range of the signal. To simulate a signal x(i) encoded with n bits of resolution spread out over the range of the signal, the value of the signal is mapped to an integer from 0 to 2n, then that integer code is converted back to signal units. The ADC code for the $i^{th}$ sample is given by:

$$ADCCode(i) = \text{round}\left[\frac{2^n}{\max(x) - \min(x)}(x(i) - \min(x))\right]. \quad (5.1)$$

Using this code, the simulated signal with the new ADC resolution, $x_{sim}$ is found by:

$$x_{sim}(i) = \frac{ADCCode(i)}{2^n}\{\max(x) - \min(x)\} + \min(x). \quad (5.2)$$

Therefore, if, for example, 8 effective bits of resolution are required for adequate force accuracy, and forces of interest excite a 12 dB dynamic range, the ADC selected should have 10 bits of resolution in order to use a minimum of 8 bits for the lowest signal level of interest.

The test data 50 is sampled with 16-bit Agilent E1432A data acquisition cards 20 in a VXI chassis, with the range set low to acquire response data without encountering clipping. Table 5.2 summarizes the effect of the lower ADC resolution on impact identification force and location accuracy. The results show that the performance of the impact identification algorithm quickly decreases once the effective bits of resolution falls past 8 bits. FIG. 15.2 shows the trend graphically with box plots showing the peak force amplitude estimation error vs ADC resolution. Table 5.2 shows the relationship between simulated bits of resolution and impact location estimation accuracy. It is understood that Table 5.2 represents various ranges of ADC resolution in various embodiments of the present invention. As one example, reasonable estimations of both the impact location and magnitude can be achieved with fewer than sixteen bits of resolution. In yet other embodiments, reasonable accuracy can be achieved with eight bits of ADC resolution.

TABLE 5.2

The effect of decreased ADC resolution on impact identification performance is summarized here.

| Simulated | Impacts | Peak Force Error Statistics | | | | |
|---|---|---|---|---|---|---|
| Bits of Resolution | Correctly Located (%) | Mean (%) | Std. Dev. | Median (%) | Min (%) | Max (%) |
| 16 | 100 | 3.85 | 3.44 | 2.84 | 0.07 | 14.34 |
| 15 | 100 | 3.85 | 3.43 | 2.84 | 0.07 | 14.34 |
| 14 | 100 | 3.86 | 3.44 | 2.85 | 0.06 | 14.33 |
| 13 | 100 | 3.86 | 3.43 | 2.85 | 0.07 | 14.34 |
| 12 | 100 | 3.86 | 3.43 | 2.85 | 0.07 | 14.34 |
| 11 | 100 | 3.85 | 3.44 | 2.87 | 0.06 | 14.35 |
| 10 | 100 | 3.88 | 3.43 | 2.87 | 0.05 | 14.32 |
| 9 | 100 | 3.83 | 3.53 | 2.77 | 0.00 | 14.28 |

TABLE 5.2-continued

The effect of decreased ADC resolution on impact identification performance is summarized here.

| Simulated Impacts | | Peak Force Error Statistics | | | | |
|---|---|---|---|---|---|---|
| Bits of Resolution | Correctly Located (%) | Mean (%) | Std. Dev. | Median (%) | Min (%) | Max (%) |
| 8 | 99.22 | 3.92 | 3.37 | 3.07 | 0.13 | 14.34 |
| 7 | 89.06 | 7.56 | 12.95 | 3.47 | 0.08 | 77.94 |
| 6 | 74.22 | 15.32 | 30.18 | 5.00 | 0.03 | 252.44 |
| 5 | 52.34 | 27.80 | 41.86 | 8.54 | 0.07 | 285.69 |
| 4 | 23.44 | 75.74 | 112.53 | 43.66 | 0.12 | 721.74 |

Because the simulations for the missile canister are limited by the original ADC used for data acquisition, the simulated plate model is used to simulate higher resolution input signals and verify the findings from analyzing the missile canister. The response measurements of the theoretical model are limited to several numbers of bits, from 24 to 4. Much like the simulation on the data from the canister, there is a certain threshold below which large errors are introduced. In this case, the threshold is around 11 bits of resolution. While the trend matches the data, the one resolution cut off for the simulation rises from 8 bits to 12 bits in some embodiments.

TABLE 5.3

Results of simulations of an aluminum plate illustrates the effect of quantization error on impact identification.

| Simulated Impacts | | Peak Force Error Statistics | | | | |
|---|---|---|---|---|---|---|
| Bits of Resolution | Correctly Located (%) | Mean (%) | Std. Dev. | Median (%) | Min (%) | Max (%) |
| 24 | 100 | 0.06 | 0.003 | 0.06 | 0.00 | 0.06 |
| 20 | 100 | 0.06 | 0.003 | 0.06 | 0.00 | 0.06 |
| 16 | 100 | 0.06 | 0.026 | 0.06 | 0.00 | 0.13 |
| 15 | 100 | 0.06 | 0.048 | 0.05 | 0.00 | 0.16 |
| 14 | 100 | 0.04 | 0.091 | 0.04 | 0.00 | 0.25 |
| 13 | 100 | 0.09 | 0.177 | 0.08 | 0.00 | 0.59 |
| 12 | 98.0 | 0.26 | 1.726 | 0.06 | 0.35 | 0.59 |
| 11 | 85.71 | 11.96 | 52.61 | 0.00 | 0.17 | 0.56 |
| 10 | 67.35 | 6.96 | 36.17 | 0.48 | 0.29 | 48.47 |
| 9 | 51.02 | 4.48 | 52.56 | 0.38 | 0.30 | 60.24 |
| 8 | 44.90 | 8.41 | 63.97 | 1.03 | 0.29 | 59.77 |
| 7 | 46.90 | 15.25 | 62.83 | 5.56 | 0.30 | 58.26 |
| 6 | 67.35 | 31.7 | 62.04 | 26.21 | 0.30 | 52.65 |
| 5 | 73.17 | 68.9 | 81.94 | 49.37 | 0.41 | 35.35 |
| 4 | 59.18 | 223.6 | 254.21 | 150.39 | 1.45 | 33.12 |

A pre-trigger is useful for ensuring that the initial rise/fall of a response, before the response crosses the triggering threshold, is not missed. The downside to having a pre-trigger on an integrated system is power consumption. To ensure a pre-trigger is recorded, the data acquisition system would always be acquiring data, and use a software trigger to decide which sections of acquired data should be saved. In contrast, a DAQ system without a pre-trigger could stay in a sleep mode until a triggering criterion is met, and then wake up to record the response signal. Because the difference in power consumption between these two cases, the effects of a system without a pre-trigger are investigated.

The wake-up time of the data acquisition system is assumed to be small enough that the sample directly after the trigger criteria is met is recorded, and in the simulation, samples before that point are simply set to zero. The variable controlling how much of the response is missed is the threshold level. If the threshold level is set low, many sets of response data corresponding to inconsequential impacts will be recorded, but little of the response to an impact will be missed. With a high threshold level, power consumption would be less because the number of sets of data recorded would be smaller, but a larger portion of the response signal would occur before the triggering condition is met, so more data would be lost in impacts of interest. FIG. 15.3 shows the effect of no pre-trigger information and a relatively high threshold. The blue signal is the original signal, and the green signal is what would be recorded if the threshold was set at the levels set by the red lines. The beginning portion of the signal is missed, because the value does not cross the threshold until a portion of the response signal has already occurred.

In order to test the effect of changing the threshold level in a standard way, the simulated threshold level is set to a fixed percentage of the response's max amplitude. In order to set a threshold in the real system, the minimum peak amplitude level of is identified, then the threshold could be set as a certain percent of that amplitude. The ratio of the threshold to maximum response amplitude is increased from 1% to 70%, and each simulated response signal is passed through the impact identification algorithm. The force and location accuracy for each threshold level are calculated, and summarized in Table 5.5, and plotted in FIG. 15.4.

The results show that for an increasing trigger threshold level, both the mean error and the variance of the peak force estimate increase. As a result, force estimations would be less accurate, and this error could not be eliminated by simply scaling by a mean expected force error, because the variance of the errors also increases. Fortunately, however, these simulations show that, especially for relatively sensitive trigger levels, the impact identification algorithm's performance holds up to response signals that are not entirely observed due to lack of pre-trigger information. Table 5.5 represents various embodiments of the present invention. For example, in one embodiment it is possible to achieve reasonable accuracy in the prediction of both the location and magnitude of the force in which the threshold is set to five percent of the maximum response. In yet another embodiment, the threshold can be set to about twenty percent of the maximum response, and reasonable accuracy can be achieved in the prediction of both the location and magnitude of the force.

TABLE 5.5

Effects of threshold level on impact identification performance without a pre-trigger are summarized here.

| Threshold | Impacts | | Max Force Error Statistics | | | | |
|---|---|---|---|---|---|---|---|
| (% Max Response) | Correctly Located (%) | Mean (%) | Std. Dev. | Median (%) | Min (%) | Max (%) |
| 1% | 100 | 3.8 | 3.3 | 2.5 | 0.33 | 14.7 |
| 5% | 100 | 5.1 | 4.2 | 4.4 | 0.18 | 20.6 |
| 10% | 98.4 | 8.8 | 12.2 | 6.4 | 0.23 | 83.8 |
| 20% | 98.4 | 14.4 | 13.5 | 8.7 | 0.29 | 62.6 |
| 30% | 92.2 | 21.3 | 16.2 | 18.3 | 0.29 | 66.2 |
| 40% | 90.6 | 30.2 | 20.2 | 26.2 | 0.83 | 81.3 |
| 50% | 82.8 | 34.3 | 23.2 | 29.7 | 0.58 | 144.4 |
| 60% | 75.0 | 40.3 | 24.0 | 40.0 | 0.58 | 144.4 |
| 70% | 64.1 | 43.8 | 20.7 | 41.8 | 4.24 | 88.6 |
| 80% | 56.3 | 55.9 | 38.4 | 54.6 | 2.87 | 255 |

Some embodiments of the present invention pertain to an impact identification method on a large aircraft using a small number of sensors. An entropy-based impact identification method developed was shown to locate more than 96% of the impacts applied to a fuselage within six inches of the actual impact location. Rapid successions of impacts were identified with similar average force estimation error to the single impact scenario, and located within twelve inches of the actual location in 87.6% of cases. In some embodiments, useful accuracy in predicting the location and/or magnitude of the load is achieved even when lowering the sampling frequency, increasing quantization error, and raising the threshold levels for detection while not using a pre-trigger.

Various aspects of different embodiments of the present invention are expressed in paragraphs X1, X2, X3, and X4, as follows.

X1. One aspect of the present invention pertains to a method for estimating an unknown load acting on an object. The method preferably includes measuring a plurality of responses of the object to the unknown load. The method preferably includes calculating a plurality of hypothetical loads each associated with a different one of the plurality of responses. The method preferably includes calculating the randomness or lack of order associated with each of the hypothetical loads.

X2. Another aspect of the present invention pertains to a method of estimating a load acting on an object. The method preferably includes calculating a plurality of hypothetical loads associated with the response of the object to the unknown load. The method preferably includes filtering or limiting or restricting one of the hypothetical loads. The method preferably includes calculating a first factor corresponding to the energy of the one hypothetical load. The method preferably includes restricting the one hypothetical load. The method preferably includes calculating a second factor corresponding to the energy of the restricted hypothetical load. The method preferably includes preparing a corrected hypothetical load based on the difference between the first factor and the second factor.

X3. Another aspect of the present invention pertains to a method for identifying damage to an object. The method preferably includes providing a plurality of time-domain data corresponding to responses of the object to an event. The method preferably includes quantifying the randomness associated with each of the plurality of responses. The method preferably includes identifying regions of the object with possible damage based on said quantifying.

X4. Another aspect of the present invention pertains to a method of estimating an unknown load acting on an object. The method preferably includes providing a signal corresponding to the response of the object to the unknown load. The method preferably includes determining that the unknown load includes a plurality of separate loads to the object. The method preferably includes processing the signal and determining a plurality of time windows, each of the time windows corresponding to a different one of the separate impacts. The method preferably includes applying the plurality of time windows to the time base of the signal to produce a plurality of separated signals, each separated signal corresponding to a different one of the separate loads.

Yet other embodiments pertain to any of the previous statements X1, X2, X3, or X4 which are combined with one or more of the following other aspects:

Which further comprises identifying the hypothetical loads having an entropy less than a predetermined value; and estimating the unknown load from the range of identified hypothetical loads.

Which further comprises selecting the unknown load from the identified hypothetical loads.

Wherein the unknown load is a hypothetical load with low entropy.

Wherein said calculating hypothetical loads is in the time domain.

Wherein said measuring is measuring a plurality of spatial responses.

Wherein said spatial responses correspond to displacement of a portion of the object.

Wherein said spatial responses correspond to velocity of a portion of the object.

Wherein said spatial responses correspond to acceleration of a portion of the object.

Wherein said measuring is measuring uniaxial, biaxial, or triaxial responses.

Which further comprises calculating the frequency characteristics of each of the plurality of responses.

Which further comprises using the calculated frequency characteristics for said calculating hypothetical loads.

Which further comprises preparing a structural mathematical model of the object wherein the degrees of freedom of said plurality of responses is substantially less than the degrees of freedom of the hypothetical loads, and said calculating is with the model.

Wherein the degrees of freedom of said plurality of responses is less than one one-tenth of the degrees of freedom of the hypothetical loads.

Wherein said calculating the entropy is in the time domain.

Wherein said preparing includes calculating the energy of the restricted hypothetical load and multiplying the energy by the ratio of the first factor to the second factor.

Wherein said preparing provides a corrected hypothetical load with substantially the same energy as the one hypothetical load.

Wherein said restricting is by eliminating some of the frequency content of the one hypothetical load.

Wherein said restricting is by placing a window on the time response of the one hypothetical load.

Wherein said calculating hypothetical loads includes the assumption that the unknown load is an impact load.

Wherein said selecting includes quantifying the randomness of the hypothetical loads in one of the time domain or frequency domain.

Which further comprises converting the time domain data to a plurality of hypothetical forcing functions, and the responses are the plurality of hypothetical forcing functions.

Wherein each of the forcing functions are substantially approximated as impact events.

Wherein said quantifying is by calculating an entropy associated with each of the plurality of responses.

Wherein said quantifying includes calculating the statistical likelihood of the responses in the time domain.

Wherein the event is a single impact load.

Wherein the event is a plurality of impact loads, the time-based response of the object to each of the impact loads overlapping in time with the onset of the next of the impact loads.

Wherein the event is an impact load.

Wherein said quantifying includes calculating the statistical likelihood of the responses in the frequency domain.

Wherein said determining is by preparing an envelope of the signal.

Wherein said preparing is in the time domain.

Wherein said preparing is an envelope of the magnitude of the signal in terms of spatial response of the object.

Wherein said preparing is by calculating a Hilbert transform of the signal.

Wherein said processing includes filtering the signal with a low pass filter.

Wherein the low pass filter does not introduce phase shift.

Which further comprises selecting relative minimums in the filtered signal, and wherein said determining is with the relative minimums.

Wherein the signal is a time history of the response.

Wherein the signal is a frequency-domain characterization of the response.

Wherein said determining includes identifying frequency content at a frequency less than about the fundamental frequency of the object structure.

Wherein said quantifying includes calculating the total information for each response, and the identified regions have more information than the non-identified regions.

Wherein said quantifying includes compressing the data into separate data files, and the identified regions have larger data files than the non-identified regions.

Wherein said quantifying includes calculating the energy of the responses.

Wherein said quantifying includes detecting the threshold crossings of the responses and the identified regions have more crossings than the non-identified regions.

While the inventions have been illustrated and described in detail in the drawings and foregoing description, the same is to be considered as illustrative and not restrictive in character, it being understood that certain embodiments have been shown and described and that all changes and modifications that come within the spirit of the invention are desired to be protected.

What is claimed is:

1. A method for estimating an unknown load acting on an aircraft structure, comprising:
   providing an aircraft structure having a plurality of accelerometers mounted thereto, a processor receiving a signal from each of the accelerometers, and a graphical user interface;
   measuring with the processor a plurality of accelerometer responses of the aircraft structure to the unknown load;
   calculating with the processor a plurality of hypothetical loads each associated with a different one of the plurality of accelerometer responses;
   calculating with the processor an entropy associated with each of the hypothetical loads and determining the location on the aircraft structure of the hypothetical load having the lowest entropy; and
   identifying the location on the graphical user interface.

2. The method of claim 1 which further comprises identifying the hypothetical loads having an entropy less than a predetermined value; and estimating the unknown load from the range of identified hypothetical loads.

3. The method of claim 1 wherein said calculating hypothetical loads are time domain impact loads.

4. The method of claim 1 wherein said measuring is measuring triaxial accelerometer responses.

5. The method of claim 1 which further comprises calculating the frequency-domain characteristics of each of the plurality of responses.

6. The method of claim 1 which further comprises preparing a structural mathematical model of the aircraft structure wherein the degrees of freedom of said plurality of responses is substantially less than the degrees of freedom of the hypothetical loads, and said calculating with the processor uses the model.

7. The method of claim 1 wherein said calculating the entropy is in the time domain.

8. The method of claim 1 wherein the aircraft structure is a fuselage including a composite panel.

9. A method of estimating an unknown load acting on an aircraft structure, comprising:
   providing an aircraft structure having a plurality of accelerometers mounted thereto, a processor receiving a signal from each of the accelerometers, and a graphical user interface;
   calculating with the processor a plurality of hypothetical loads associated with the acceleration response of the aircraft structure to the unknown load;
   selecting one of the hypothetical loads;
   calculating with the processor a first factor corresponding to the energy of the one hypothetical load;
   restricting the one hypothetical load;
   calculating with the processor a second factor corresponding to the energy of the restricted hypothetical load;
   preparing a corrected hypothetical load based on the difference between the first factor and the second factor; and
   identifying the location of the selected load on the aircraft structure with the graphical user interface.

10. The method of claim 9 wherein said preparing includes calculating the energy of the restricted hypothetical load and multiplying the energy by the ratio of the first factor to the second factor.

11. The method of claim 9 wherein said restricting is by eliminating some of the frequency content of the one hypothetical load.

12. The method of claim 9 wherein said restricting is by placing a window on the time response of the one hypothetical load.

13. The method of claim 9 wherein said selecting includes quantifying the randomness of the hypothetical loads in one of the time domain or frequency domain.

14. A method for identifying damage to an aircraft structure, comprising:
   providing an aircraft structure having a plurality of accelerometers mounted thereto, and a structural health monitoring system including a processor;
   providing to the processor a plurality of time-domain data corresponding to responses of the aircraft structure to an event;
   quantifying with the processor the randomness associated with each of the plurality of responses;
   identifying with the processor regions of the aircraft structure with possible damage based on said quantifying; and
   notifying a user of the structural health monitoring system of the identified regions of the aircraft structure.

15. The method of claim 14 which further comprises converting the time domain data to a plurality of hypothetical forcing functions, and the responses are the plurality of hypothetical forcing functions.

16. The method of claim 15 wherein the hypothetical forcing functions are impact loads.

17. The method of claim 14 wherein said quantifying is by calculating an entropy associated with each of the plurality of responses.

18. The method of claim 14 wherein said quantifying includes calculating the statistical likelihood of the responses in the frequency domain.

19. The method of claim 14 wherein said quantifying includes compressing the data into separate data files, and the identified regions have larger data files than the non-identified regions.

20. The method of claim 14 wherein said quantifying includes calculating the energy of the responses.

21. The method of claim 14 wherein said quantifying includes detecting the threshold crossings of the responses and the identified regions have more crossings than the non-identified regions.

22. A method of estimating an unknown load acting on an aircraft structure, comprising:
   providing an accelerometer signal corresponding to the acceleration response of the aircraft structure to the unknown load;
   determining with a digital processor that the unknown load includes a plurality of separate impact loads to the aircraft structure;
   digitally processing the signal and determining with the processor a plurality of time windows, each of the time windows corresponding to a different one of the separate impacts;
   applying the plurality of time windows to the time base of the signal to produce a plurality of separated signals, each separated signal corresponding to a different one of the separate loads;
   transmitting the separated signals to a structural health monitoring system; and
   identifying with the structural health monitoring system from the separated signals at least one of the location or magnitude for one of the separated loads acting on the aircraft structure.

23. The method of claim 22 wherein said determining is by preparing an envelope of the signal.

24. The method of claim 23 wherein said preparing is an envelope of the magnitude of the signal in terms of the time-based spatial response of the aircraft structure.

25. The method of claim 23 wherein said preparing is by calculating a Hilbert transform of the signal.

26. The method of claim 22 wherein said processing includes filtering the signal with a low pass filter.

27. The method of claim 26 which further comprises selecting relative minimums in the filtered signal, and wherein said determining is with the relative minimums.

* * * * *